(12) United States Patent
Molyneux et al.

(10) Patent No.: US 11,541,296 B2
(45) Date of Patent: Jan. 3, 2023

(54) ATHLETIC PERFORMANCE MONITORING SYSTEMS AND METHODS IN A TEAM SPORTS ENVIRONMENT

(71) Applicant: NIKE, Inc., Beaverton, OR (US)

(72) Inventors: James Molyneux, Portland, OR (US); Aaron B. Weast, Portland, OR (US); Brandon S. Burroughs, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 16/225,369

(22) Filed: Dec. 19, 2018

(65) Prior Publication Data

US 2019/0118036 A1    Apr. 25, 2019

Related U.S. Application Data

(63) Continuation of application No. 14/845,993, filed on Sep. 4, 2015, now Pat. No. 10,173,101, which is a
(Continued)

(51) Int. Cl.
*A63B 71/06* (2006.01)
*A63B 71/12* (2006.01)
(Continued)

(52) U.S. Cl.
CPC ............ *A63B 71/06* (2013.01); *A43B 1/0054* (2013.01); *A43B 3/34* (2022.01); *A43B 5/00* (2013.01);
(Continued)

(58) Field of Classification Search
CPC ............ A63B 24/0062; A63B 71/0622; A63B 71/1225; A63B 71/081; A63B 24/0021; A63B 71/0605; A63B 2243/0095; A63B 2071/065; A63B 2071/1258; A63B 2102/24; A63B 2102/32; A63B 2102/20;
(Continued)

(56) References Cited

U.S. PATENT DOCUMENTS

| | | |
|---|---|---|
| 4,577,865 A | 3/1986 | Shishido |
| 4,702,475 A | 10/1987 | Elstein et al. |

(Continued)

FOREIGN PATENT DOCUMENTS

| | | |
|---|---|---|
| CN | 1231753 A | 10/1999 |
| CN | 1790235 A | 6/2006 |

(Continued)

OTHER PUBLICATIONS

Apr. 25, 2012—(EP) European Search Report—App. No. 11195591.0.

(Continued)

*Primary Examiner* — Sundhara M Ganesan
*Assistant Examiner* — Shila Jalalzadeh Abyaneh
(74) *Attorney, Agent, or Firm* — Banner & Witcoff, Ltd.

(57) ABSTRACT

Systems and methods for sensing and monitoring various athletic performance metrics, e.g., during the course of a game, a practice, a training session, training drills, and the like, are described. These systems and methods can provide useful metrics for players and coaches relating to athletic performances in various sports, including various team sports.

16 Claims, 60 Drawing Sheets

Related U.S. Application Data continuation of application No. 12/630,737, filed on Dec. 3, 2009, now abandoned.

(60) Provisional application No. 61/186,740, filed on Jun. 12, 2009, provisional application No. 61/200,953, filed on Dec. 5, 2008.

(51) Int. Cl.

| | | |
|---|---|---|
| *A63B 71/08* | (2006.01) | |
| *G16H 20/30* | (2018.01) | |
| *A63B 24/00* | (2006.01) | |
| *A43B 5/02* | (2006.01) | |
| *G01S 13/34* | (2006.01) | |
| *G01S 13/75* | (2006.01) | |
| *G01S 13/82* | (2006.01) | |
| *A43B 3/34* | (2022.01) | |
| *A43B 1/00* | (2006.01) | |
| *A43B 5/00* | (2022.01) | |
| *A63B 43/00* | (2006.01) | |
| *A63B 102/24* | (2015.01) | |
| *A63B 102/32* | (2015.01) | |
| *A63B 102/20* | (2015.01) | |
| *A63B 102/02* | (2015.01) | |
| *A63B 102/14* | (2015.01) | |
| *A63B 102/22* | (2015.01) | |
| *A63B 102/18* | (2015.01) | |
| *G16H 40/67* | (2018.01) | |
| *G16Y 10/65* | (2020.01) | |
| *G16Y 20/10* | (2020.01) | |
| *G16Y 40/10* | (2020.01) | |
| *G16Z 99/00* | (2019.01) | |

(52) U.S. Cl.
CPC .......... *A43B 5/02* (2013.01); *A63B 24/0021* (2013.01); *A63B 71/0605* (2013.01); *A63B 71/0622* (2013.01); *A63B 71/081* (2013.01); *A63B 71/1225* (2013.01); *G01S 13/34* (2013.01); *G01S 13/751* (2013.01); *G01S 13/82* (2013.01); *A63B 24/0062* (2013.01); *A63B 43/00* (2013.01); *A63B 2024/0025* (2013.01); *A63B 2024/0028* (2013.01); *A63B 2024/0071* (2013.01); *A63B 2071/065* (2013.01); *A63B 2071/1258* (2013.01); *A63B 2102/02* (2015.10); *A63B 2102/14* (2015.10); *A63B 2102/18* (2015.10); *A63B 2102/20* (2015.10); *A63B 2102/22* (2015.10); *A63B 2102/24* (2015.10); *A63B 2102/32* (2015.10); *A63B 2220/12* (2013.01); *A63B 2220/13* (2013.01); *A63B 2220/40* (2013.01); *A63B 2220/53* (2013.01); *A63B 2220/56* (2013.01); *A63B 2220/58* (2013.01); *A63B 2220/833* (2013.01); *A63B 2220/836* (2013.01); *A63B 2220/89* (2013.01); *A63B 2225/50* (2013.01); *A63B 2225/54* (2013.01); *A63B 2243/007* (2013.01); *A63B 2243/0025* (2013.01); *A63B 2243/0066* (2013.01); *A63B 2243/0095* (2013.01); *G16H 20/30* (2018.01); *G16H 40/67* (2018.01); *G16Y 10/65* (2020.01); *G16Y 20/10* (2020.01); *G16Y 40/10* (2020.01); *G16Z 99/00* (2019.02); *Y10S 482/901* (2013.01)

(58) Field of Classification Search
CPC .......... A63B 2102/02; A63B 2102/14; A63B 2102/22; A63B 2102/18; A63B 43/00; A63B 2024/0025; A63B 2024/0028; A63B 2024/0071; A63B 2220/12; A63B 2220/13; A63B 2220/40; A63B 2220/53; A63B 2220/56; A63B 2220/58; A63B 2220/833; A63B 2220/836; A63B 2220/89; A63B 2225/50; A63B 2225/54; A63B 2243/0025; A63B 2243/0066; A63B 2243/007; G16H 20/30; G16H 40/67; A43B 5/00; A43B 3/0005; A43B 5/02; A43B 1/0054; G01S 13/34; G01S 13/751; G01S 13/82; G06F 19/00; G06F 19/3481; Y10S 482/901

See application file for complete search history.

(56) References Cited

U.S. PATENT DOCUMENTS

| | | | |
|---|---|---|---|
| 5,225,809 A * | 7/1993 | Bunn | G01S 5/04 |
| | | | 340/574 |
| 5,456,027 A | 10/1995 | Tecchio et al. | |
| 6,002,645 A | 12/1999 | Booth | |
| 6,073,086 A | 6/2000 | Marinelli | |
| 6,157,898 A | 12/2000 | Marinelli | |
| 6,320,173 B1 | 11/2001 | Vock et al. | |
| 6,418,181 B1 | 7/2002 | Nissila | |
| 6,620,057 B1 | 9/2003 | Pirritano et al. | |
| 7,040,998 B2 | 5/2006 | Jolliffe et al. | |
| 7,174,277 B2 | 2/2007 | Vock et al. | |
| 7,200,856 B2 | 4/2007 | Perlman | |
| 7,273,431 B2 | 9/2007 | DeVall | |
| 7,321,330 B2 | 1/2008 | Sajima | |
| 7,487,045 B1 | 2/2009 | Vieira | |
| 7,513,852 B2 | 4/2009 | Wilkins et al. | |
| 7,620,466 B2 | 11/2009 | Neale et al. | |
| 7,627,451 B2 | 12/2009 | Vock et al. | |
| 7,698,830 B2 | 4/2010 | Townsend et al. | |
| 7,791,808 B2 | 9/2010 | French et al. | |
| 8,054,176 B2 | 11/2011 | Karjalainen | |
| 8,070,620 B2 | 12/2011 | Rankin | |
| 8,257,189 B2 | 9/2012 | Koudele et al. | |
| 8,337,212 B2 | 12/2012 | Prstojevich | |
| 8,353,791 B2 | 1/2013 | Holthouse et al. | |
| 8,360,904 B2 * | 1/2013 | Oleson | A61B 5/1118 |
| | | | 482/8 |
| 8,602,949 B2 | 12/2013 | Pelletter | |
| 2002/0030742 A1 | 3/2002 | Aman et al. | |
| 2002/0155925 A1 | 10/2002 | Smith | |
| 2002/0170193 A1 | 11/2002 | Townsend et al. | |
| 2003/0032529 A1* | 2/2003 | Alessandri | A63B 24/00 |
| | | | 482/94 |
| 2003/0049590 A1 | 3/2003 | Feldbau | |
| 2004/0058749 A1 | 3/2004 | Pirritano et al. | |
| 2004/0125013 A1 | 7/2004 | Haselsteiner et al. | |
| 2004/0142766 A1 | 7/2004 | Savarese et al. | |
| 2005/0162257 A1 | 7/2005 | Gonzalez | |
| 2005/0183292 A1 | 8/2005 | DiBenedetto et al. | |
| 2005/0187644 A1 | 8/2005 | Neale et al. | |
| 2005/0270156 A1 | 12/2005 | Ravet | |
| 2006/0128503 A1 | 6/2006 | Savarese et al. | |
| 2006/0148594 A1 | 7/2006 | Saintoyant et al. | |
| 2006/0178235 A1 | 8/2006 | Coughlan et al. | |
| 2007/0006489 A1 | 1/2007 | Case et al. | |
| 2007/0021269 A1* | 1/2007 | Shum | A61B 5/6831 |
| | | | 482/8 |
| 2007/0032748 A1* | 2/2007 | McNeil | A61B 5/1121 |
| | | | 600/595 |
| 2007/0060425 A1* | 3/2007 | Kuenzler | A63B 41/00 |
| | | | 473/570 |
| 2007/0130287 A1 | 6/2007 | Kumar et al. | |
| 2007/0135243 A1 | 6/2007 | LaRue et al. | |
| 2007/0149361 A1 | 6/2007 | Jung et al. | |
| 2007/0178967 A1 | 8/2007 | Rosenberg | |
| 2007/0187266 A1 | 8/2007 | Porter et al. | |
| 2007/0191083 A1 | 8/2007 | Kuenzler et al. | |
| 2008/0045358 A1 | 2/2008 | VanDelden | |
| 2008/0088303 A1* | 4/2008 | Englert | A63B 24/0021 |
| | | | 324/226 |

(56) References Cited

U.S. PATENT DOCUMENTS

| | | | |
|---|---|---|---|
| 2008/0090683 A1 | 4/2008 | Englert et al. | |
| 2008/0207347 A1* | 8/2008 | Rose | A63B 69/3676 473/409 |
| 2008/0214360 A1* | 9/2008 | Stirling | A61B 5/1038 482/9 |
| 2008/0261776 A1 | 10/2008 | Skiba | |
| 2008/0286733 A1* | 11/2008 | Claudel | A63F 13/218 434/251 |
| 2008/0312935 A1* | 12/2008 | Mau, II | G11B 27/105 704/275 |
| 2009/0048039 A1 | 2/2009 | Holthouse et al. | |
| 2009/0048044 A1* | 2/2009 | Oleson | A43B 5/00 473/570 |
| 2009/0048070 A1* | 2/2009 | Vincent | A63B 71/0686 482/8 |
| 2009/0233770 A1 | 9/2009 | Vincent et al. | |
| 2009/0235761 A1 | 9/2009 | Song | |
| 2010/0026809 A1* | 2/2010 | Curry | H04N 5/23238 348/157 |
| 2010/0125028 A1 | 5/2010 | Heppert | |
| 2010/0231410 A1 | 9/2010 | Seisenberger et al. | |
| 2010/0251574 A1 | 10/2010 | Battlogg et al. | |
| 2010/0277617 A1 | 11/2010 | Hollinger | |
| 2010/0279822 A1 | 11/2010 | Ford | |
| 2011/0208444 A1 | 8/2011 | Solinsky | |
| 2011/0304497 A1 | 12/2011 | Molyneux et al. | |
| 2012/0121174 A1 | 5/2012 | Bhagavathy et al. | |
| 2014/0342329 A1 | 11/2014 | Debenedetto et al. | |
| 2015/0062440 A1 | 3/2015 | Baxter et al. | |

FOREIGN PATENT DOCUMENTS

| | | |
|---|---|---|
| CN | 101367013 A | 2/2009 |
| CN | 102341149 A | 2/2012 |
| CN | 102369046 A | 3/2012 |
| DE | 202004006680 U1 | 3/2005 |
| DE | 202005018370 U1 | 1/2006 |
| DE | 102007001820 B3 | 1/2008 |
| EP | 848934 A1 | 6/1998 |
| EP | 1928178 A1 | 6/2008 |
| EP | 2025370 A1 | 2/2009 |
| EP | 2025372 A2 | 2/2009 |
| GB | 2246891 A | 2/1992 |
| JP | S59232562 A | 12/1984 |
| JP | S62-55580 A | 3/1987 |
| JP | H01182782 A | 7/1989 |
| JP | H06214169 A | 8/1994 |
| JP | H07056990 A | 3/1995 |
| JP | H10090396 | 4/1998 |
| JP | H10-216285 A | 8/1998 |
| JP | 2001273500 A | 10/2001 |
| JP | 2003264503 A | 9/2003 |
| JP | 2004024627 A | 1/2004 |
| JP | 2006024717 A | 1/2006 |
| JP | 2006034717 A | 2/2006 |
| JP | 2006055532 A | 3/2006 |
| JP | 2006518247 A | 8/2006 |
| JP | 2008073209 A | 4/2008 |
| JP | 2008073211 A | 4/2008 |
| JP | 2008524589 A | 7/2008 |
| JP | 2009503466 A | 1/2009 |
| JP | 2009045462 A | 3/2009 |
| JP | 2009047583 A | 3/2009 |
| JP | 2010236951 A | 10/2010 |
| JP | 2011501831 A | 1/2011 |
| JP | 2012510876 A | 5/2012 |
| JP | 2012139493 A | 7/2012 |
| KR | 20060066261 A | 6/2006 |
| KR | 20060134119 A | 12/2006 |
| KR | 20120076418 A | 7/2012 |
| WO | 2004066837 A1 | 8/2004 |
| WO | 2005050868 A1 | 6/2005 |
| WO | 2005103863 A2 | 11/2005 |
| WO | 2006097357 A1 | 9/2006 |
| WO | 2007130287 A2 | 11/2007 |
| WO | 2008033338 A2 | 3/2008 |
| WO | WO-2008033338 A2 * | 3/2008 ......... A63B 24/0003 |

OTHER PUBLICATIONS

Jun. 15, 2010—(WO) International Search Report—App. No. PCT/US2009/066745.

Apr. 1, 2014—(EP) Extended ESR—App. No. 13196123.7.

Oliver Birbach et al., "Realtime perception for catching a flying ball with a mobile humanoid", Robotics and Automation (ICRA), 2011 IEEE International Conference ON, IEEE, May 9, 2011 (May 9, 2011), pp. 5955-5962, XP032033950.

Jinchang Ren et al: "Real-Time Modeling of 3-D Soccer Ball Trajectories From Multiple Fixed Cameras", IEEE Transactions on Circuits and Systems for Video Technology, vol. 18, No. 3, Mar. 1, 2008 (Mar. 1, 2008),pp. 350-362, XP055100539.

Stefan Schiffer et al: "Qualitative World Models for Soccer Robots", Qualitative Constraint Calculi,, URL:<http://www-kbsg.informati>k.rwth-aachen.de/sites/kbsg/files/schifferFL06kiqcc.pdf Jun. 14, 2006 (Jun. 14, 2006), pp. 1-12.

Oliver Birbach: "Accuracy Annalysis of Cameral-Interial Sensor-Based Ball Trajectory Prediction", Diploma thesis, Universiry of Bremen, Feb. 13, 2008(Feb. 13, 2008), http://www.informatik.uni-bremen.de/agebv2/downloads/published/birbach_thesis_08.pdf.

Jun. 13, 2014—(WO) ISR and WO—App. No. PCT/US2013/066841.

Plagge et al: "Design and Evaluation of the T-Team of the University of Tuebingen for RoboCup '98" in "Network and Parallel Computing", Jan. 1, 1999 (Jan. 1, 1999), Springer Inernational Publishing, Cham 032548, XP055334016, ISSN: 0302-9743, ISBN: 978-3-642-23677-8, vol. 1604, pp. 464-472, DOI: 40.1007/3-540-48422-1_47.

* cited by examiner

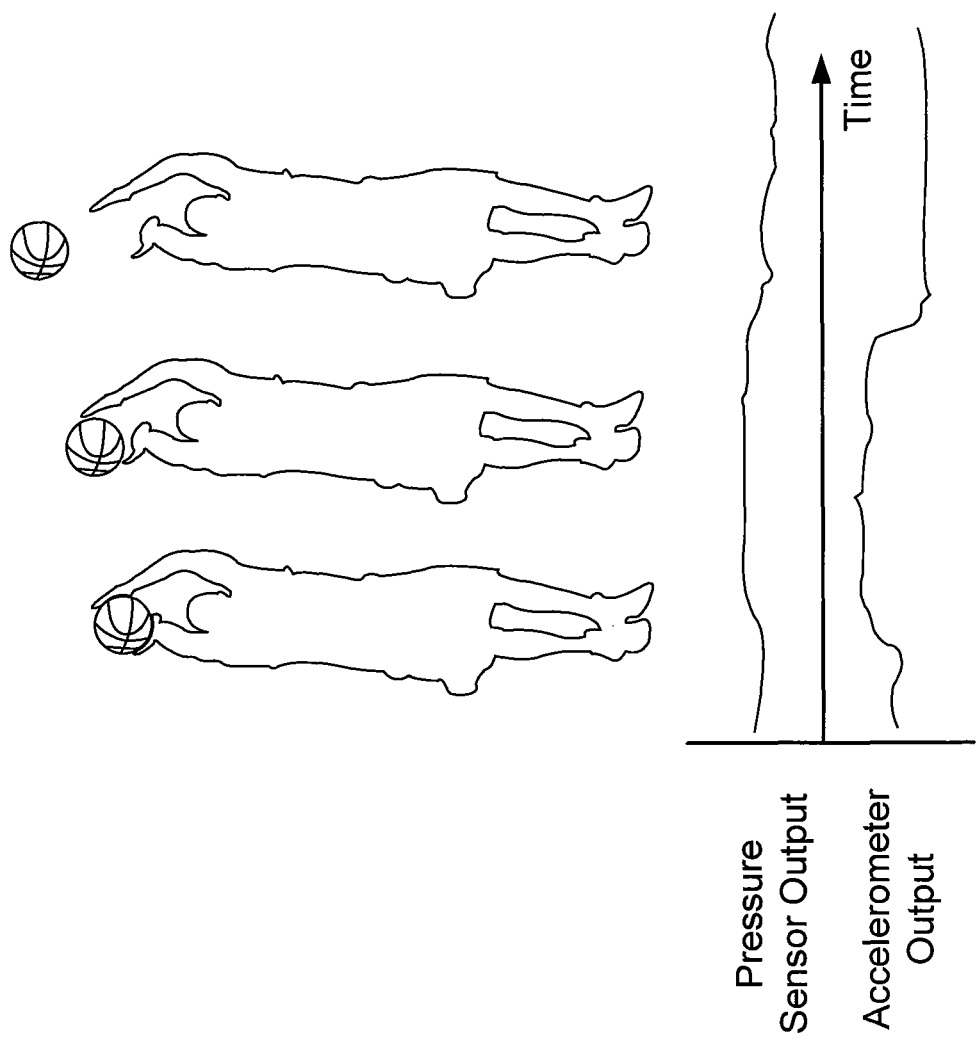

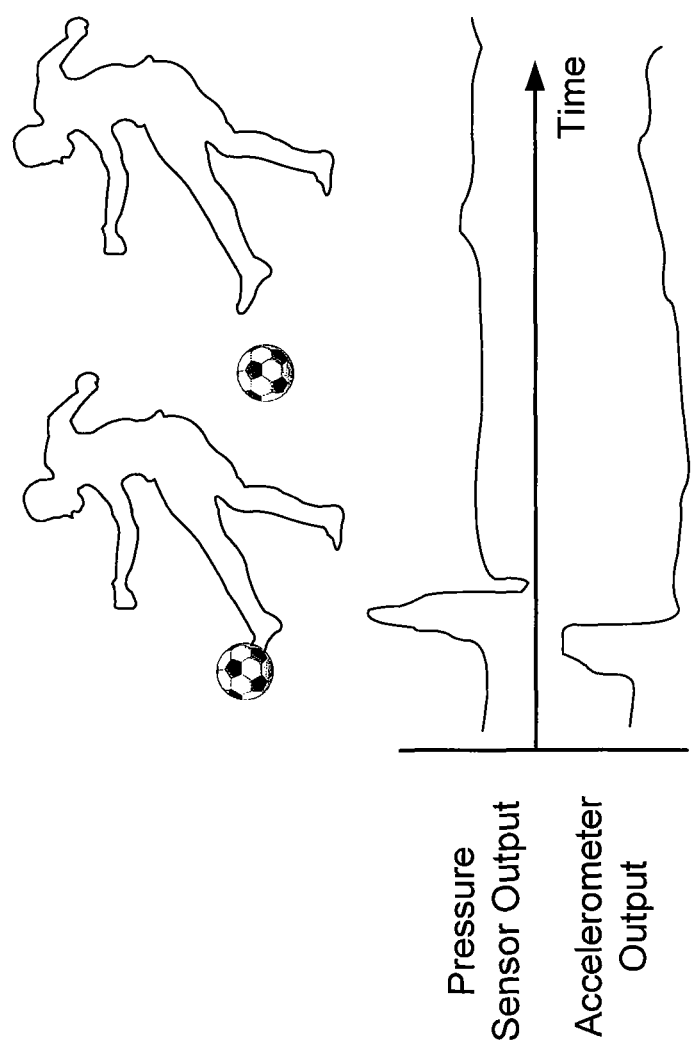

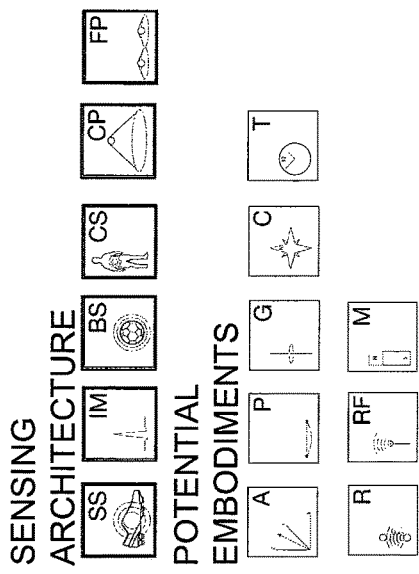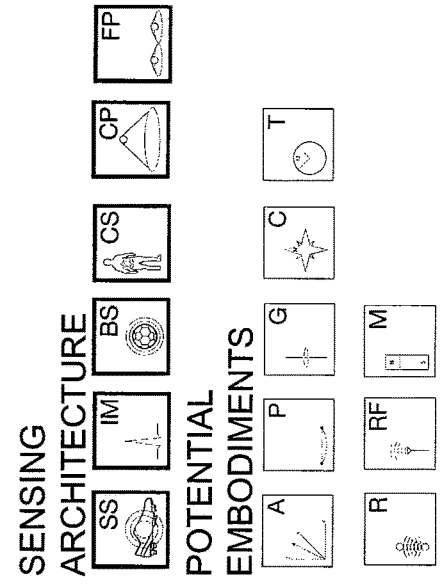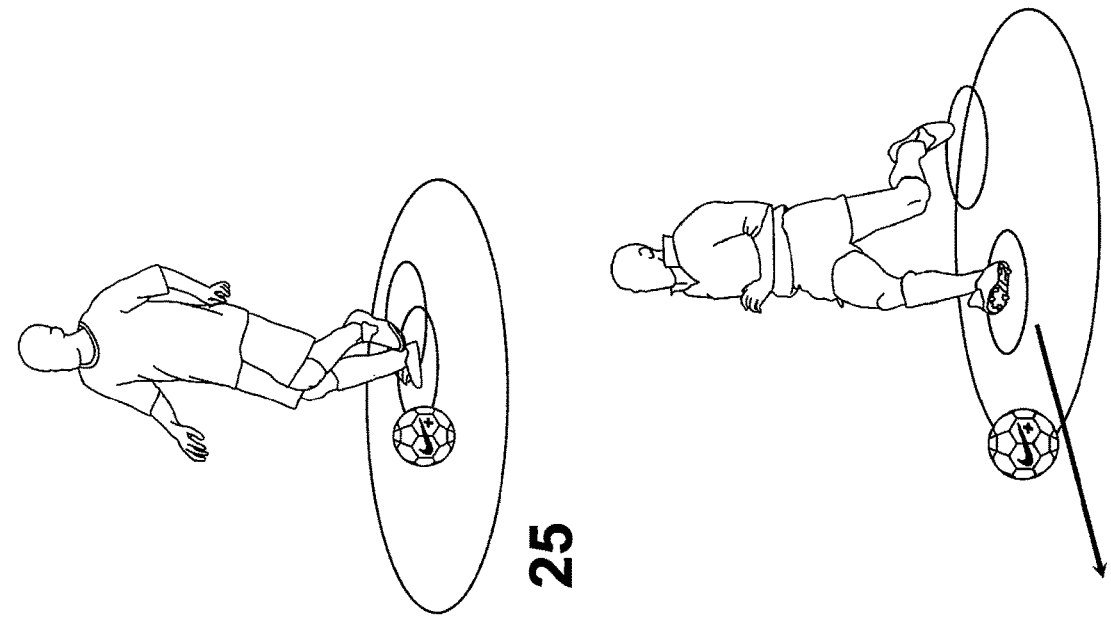
FIG. 24
FIG. 25

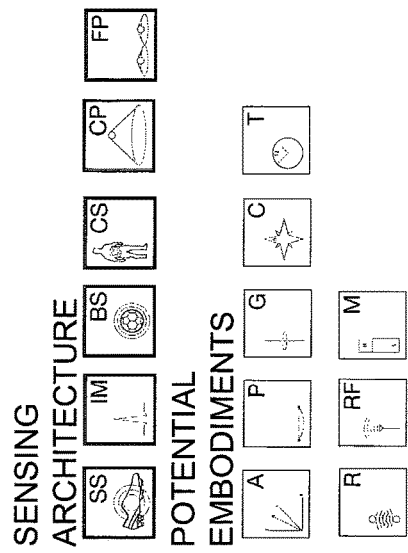
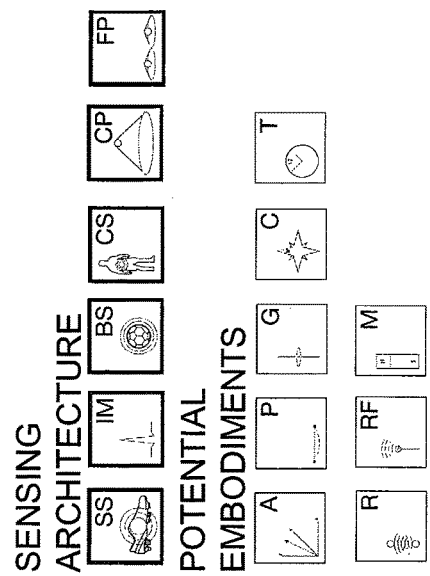
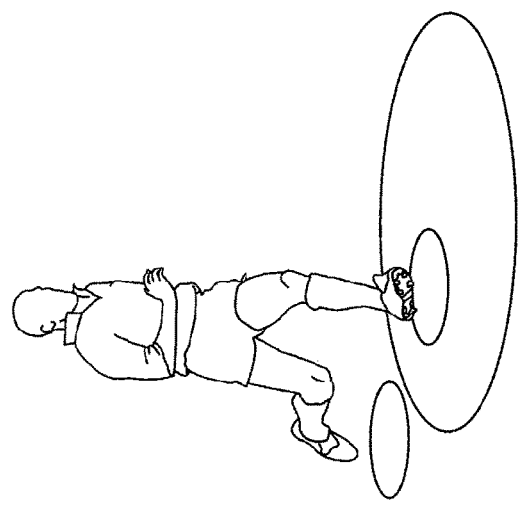
FIG. 26
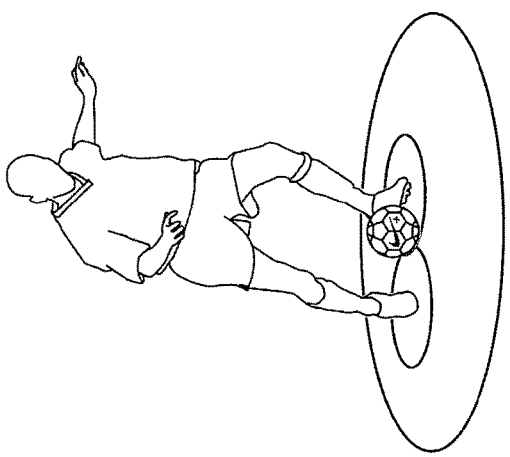
FIG. 27

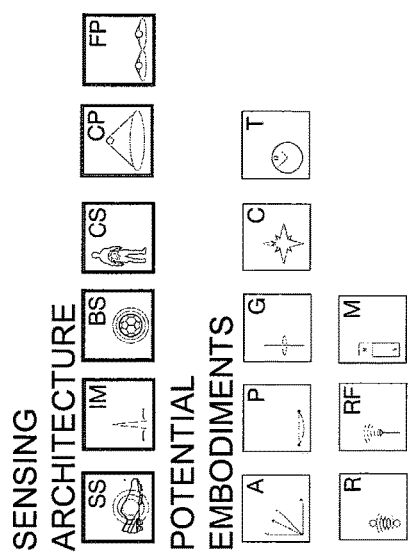
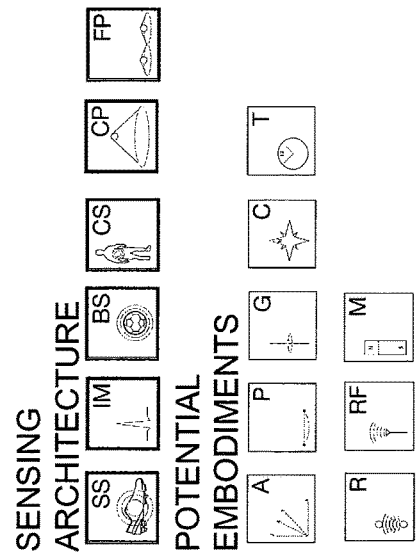
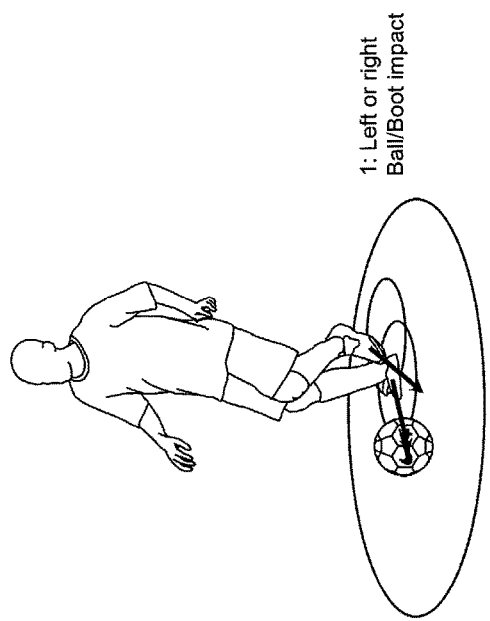
FIG. 28
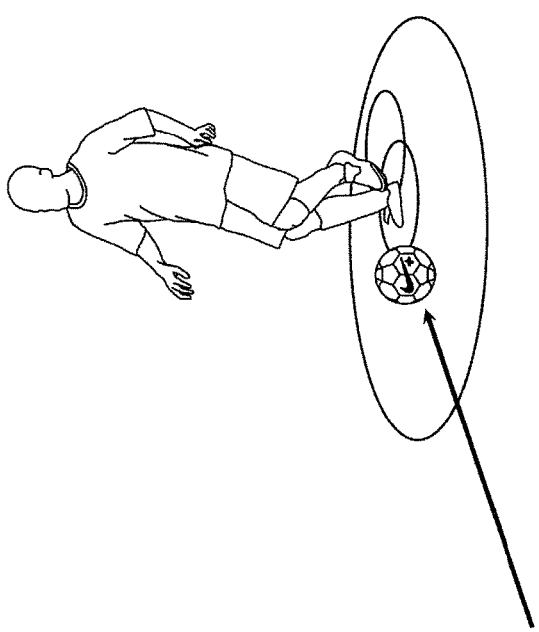
FIG. 29

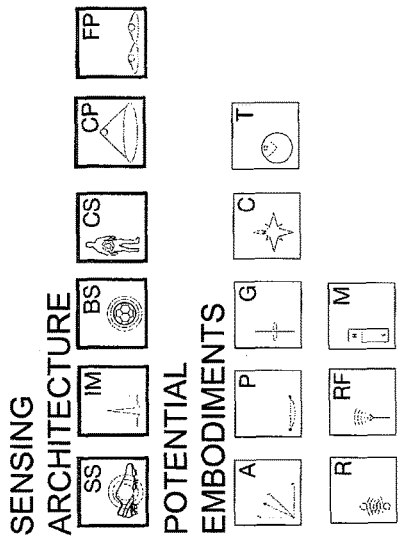
FIG. 30
1: Incoming pass
2: Outgoing pass after 1 touch
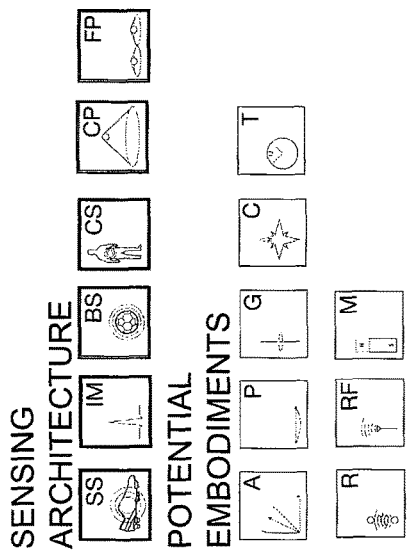
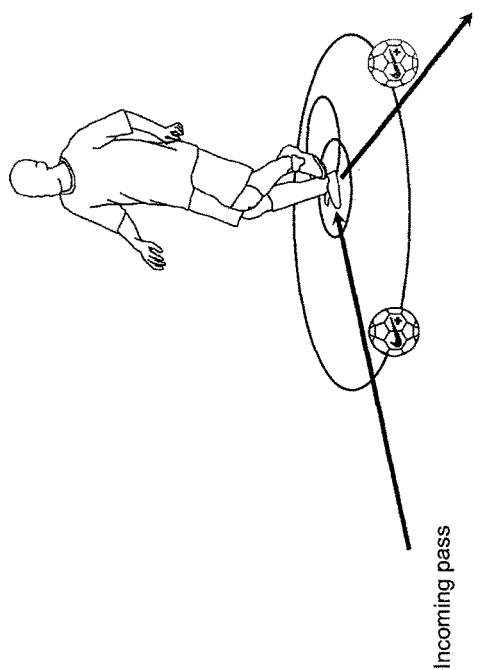
FIG. 31
1: Player A has possession, Player B approaches
2: Player B attempts a tackle
3: Player A keeps possession, and breaks away from Player B

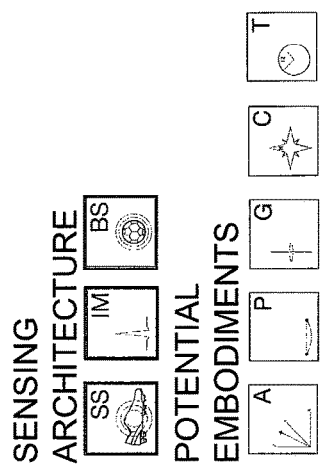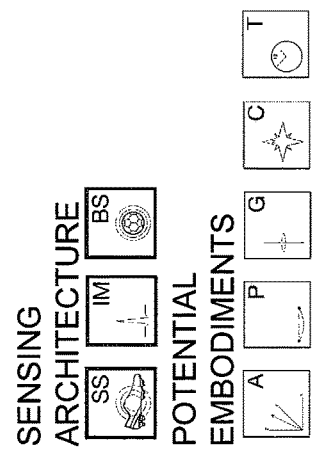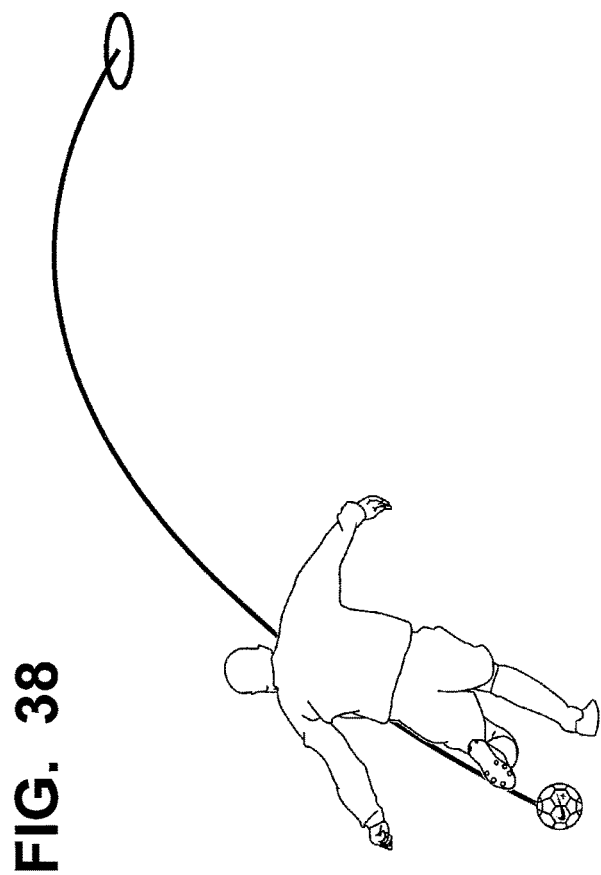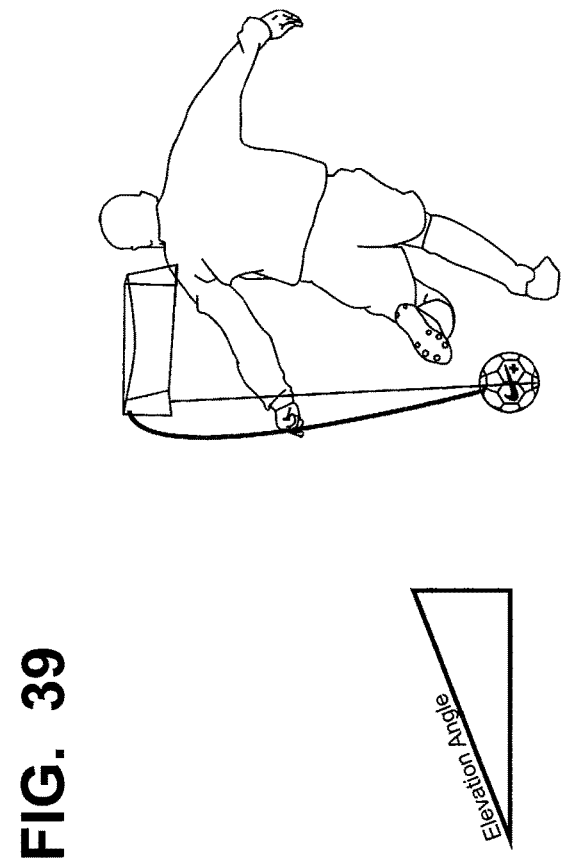
FIG. 38
FIG. 39

1: Player A has possession, and is running at speed.

2: Player A kicks the moving ball. The ball reports accurate speed and that a successful pass has been made.

1: Player A has possession, Player B approaches
2: Player B attempts a tackle and gives away a free kick
3: Player A gets to place the ball and take a set piece 1: Penalty set distance and only keeper can be near the ball
2: Set piece, varied distance and ball passes other players proximity

FIG. 50
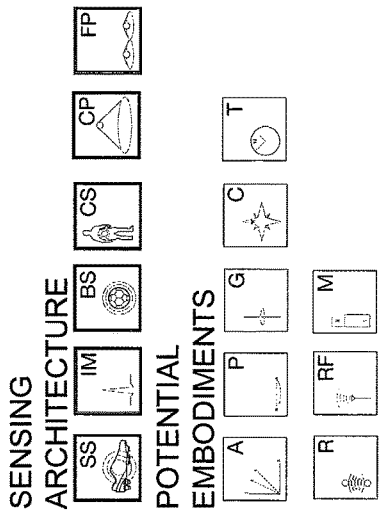
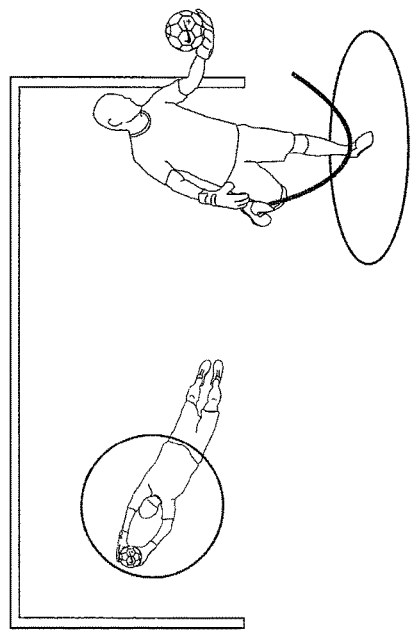
1: Keeper saves ball
2: Keeper kicks/throws the ball
FIG. 51
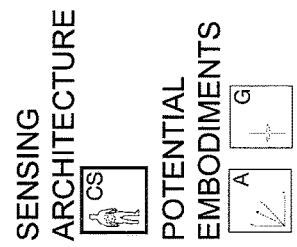
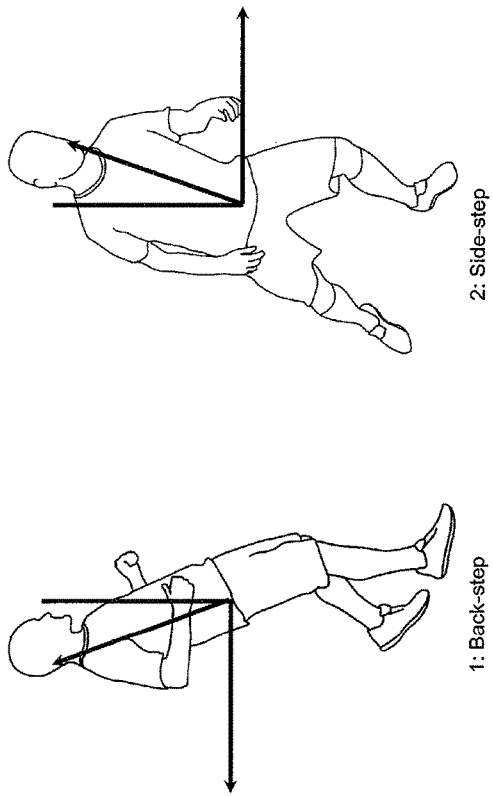
1: Back-step
2: Side-step

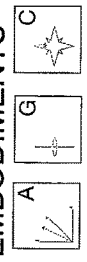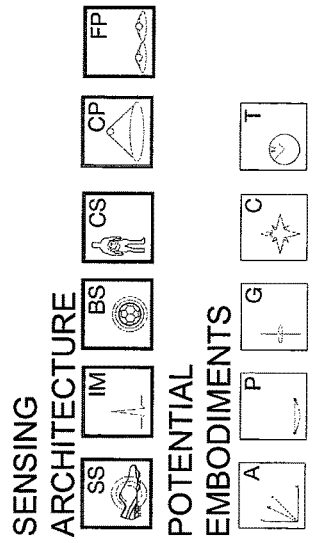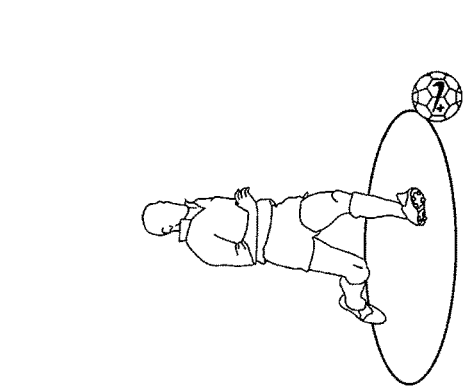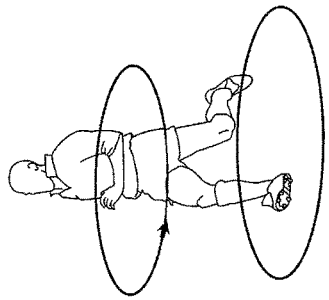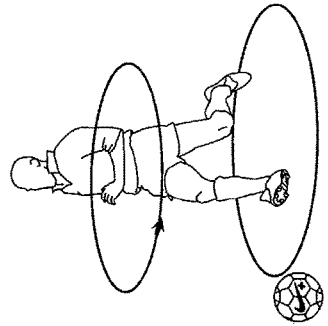
FIG. 52
FIG. 53

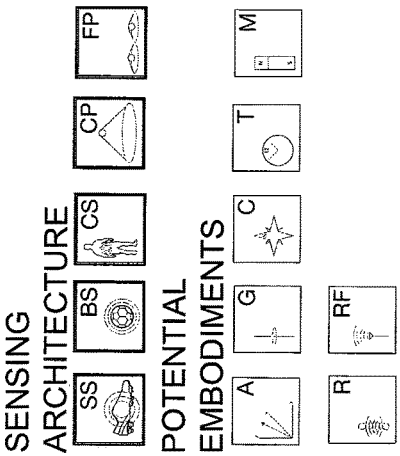
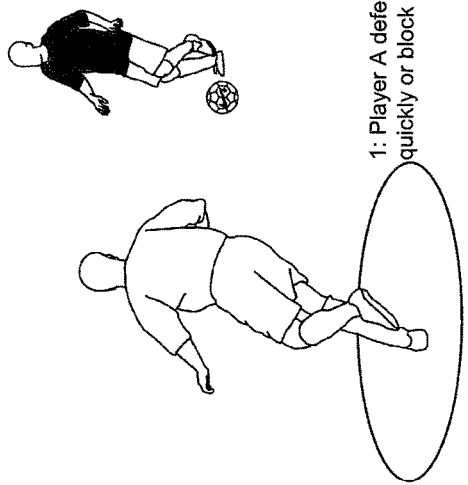
FIG. 56
1: Player A defensive posturing, getting ready to move quickly or block advancing player B movement
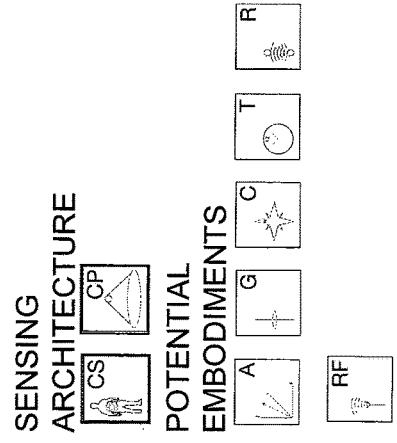
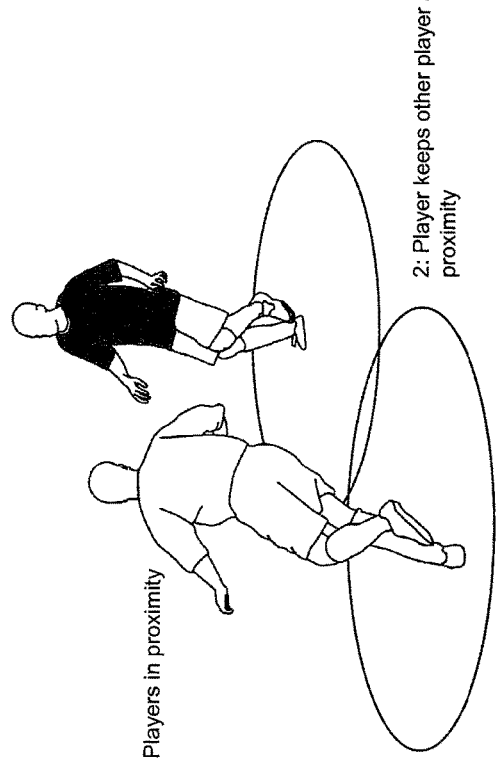
FIG. 57
1: Players in proximity
2: Player keeps other player in proximity 1: Players in proximity
2: Player A turns and breaks away

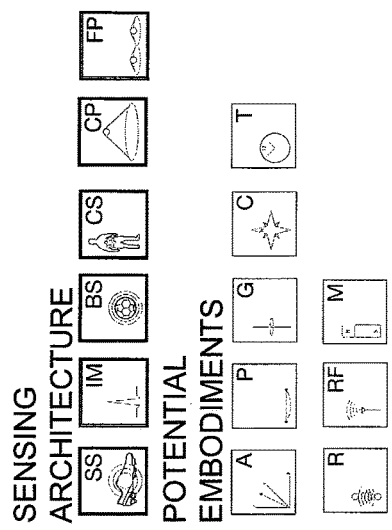
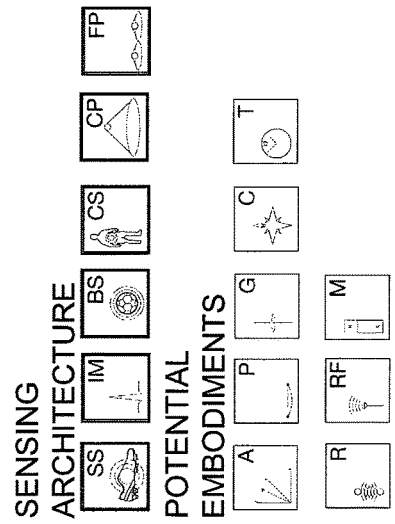
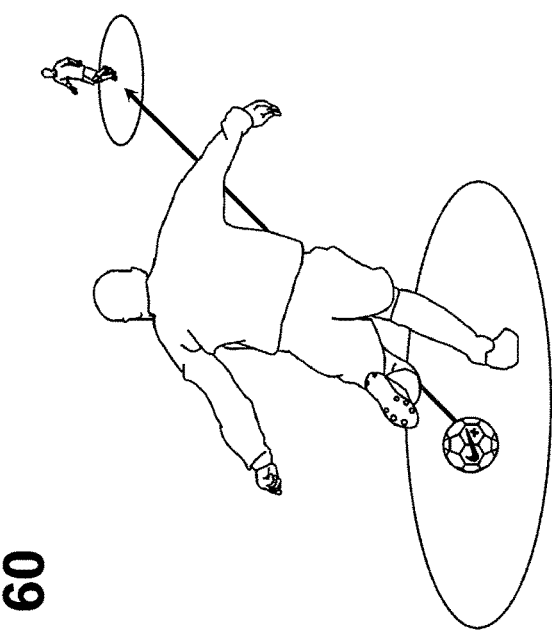
FIG. 60
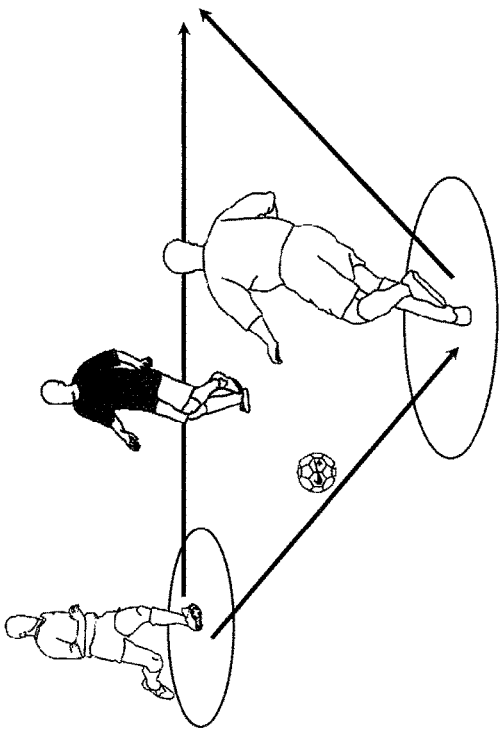
FIG. 61

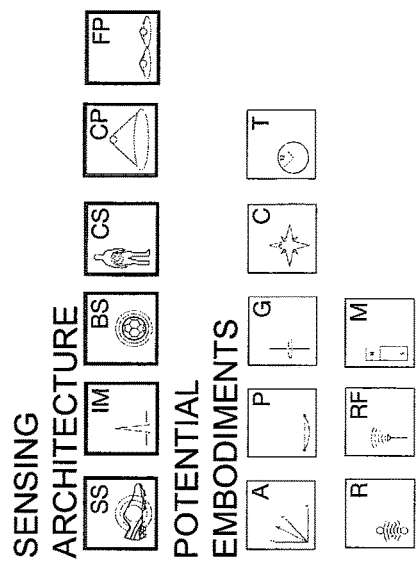
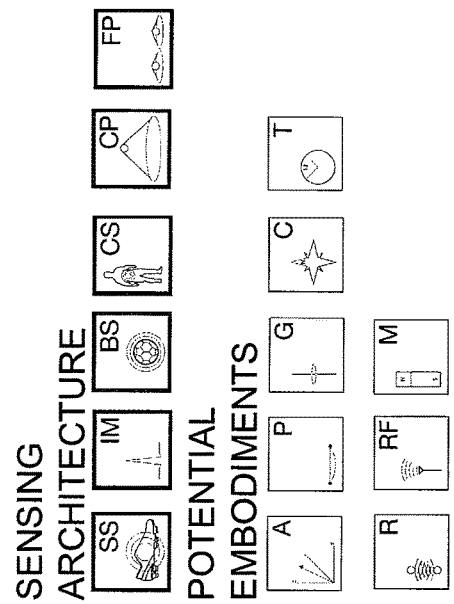
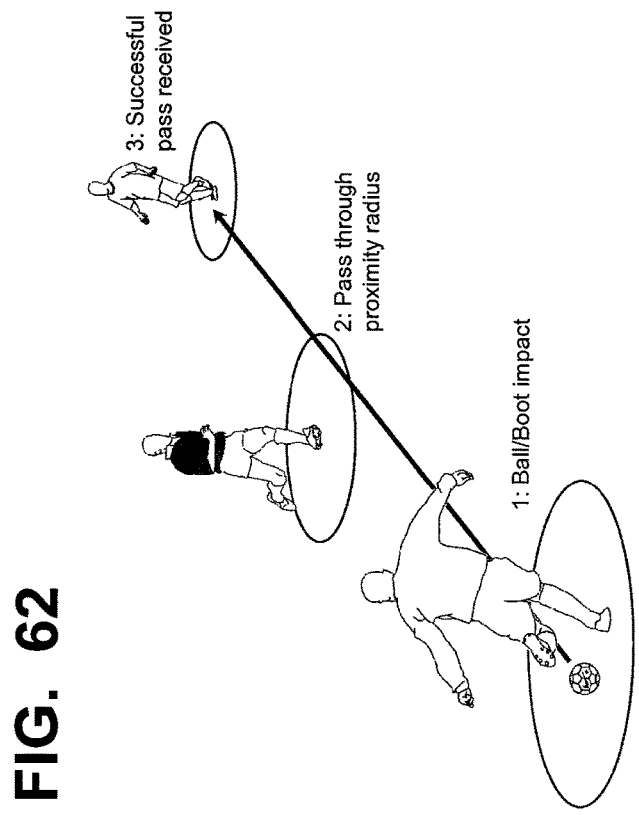
FIG. 62
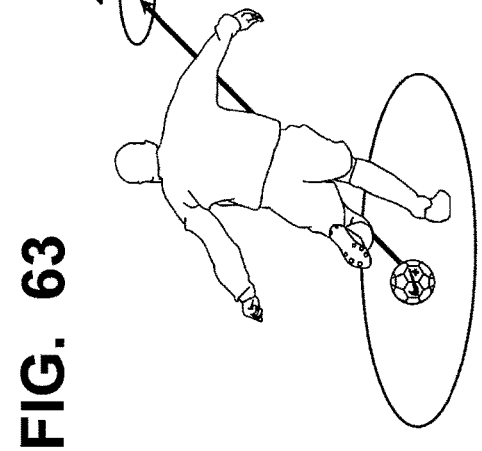
FIG. 63

FIG. 66
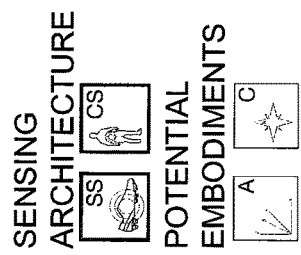
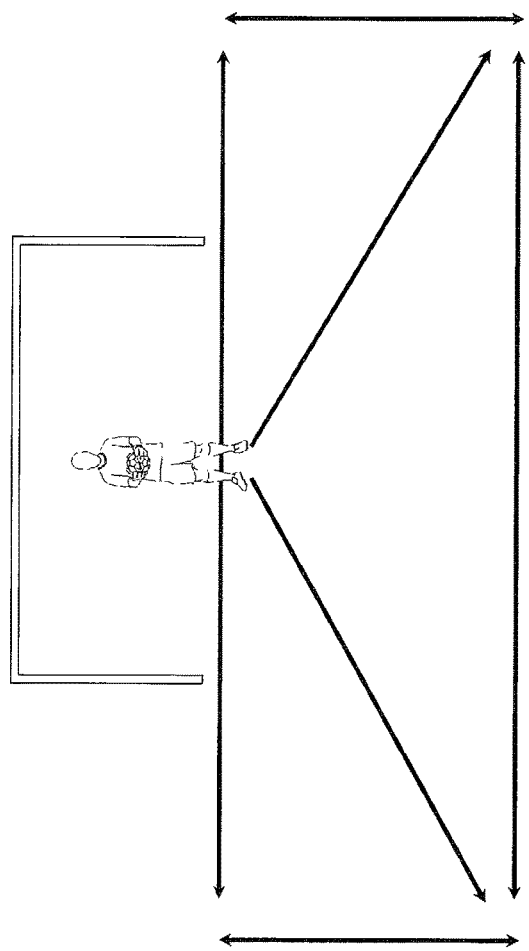
FIG. 67
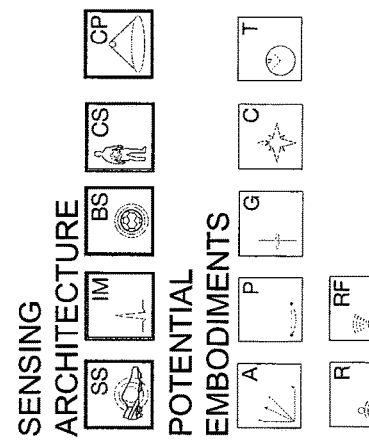
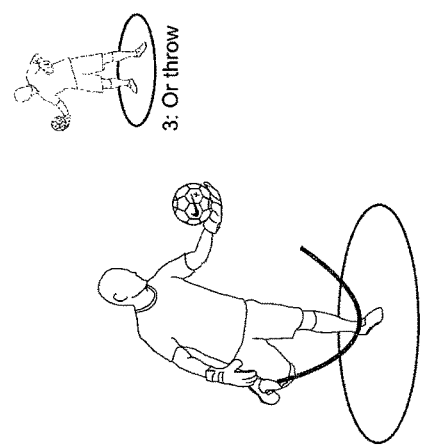
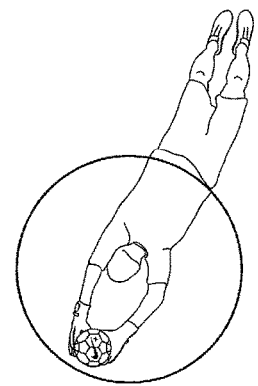
1: Keeper catch the ball  2: Keeper hold ball and kick out  3: Or throw

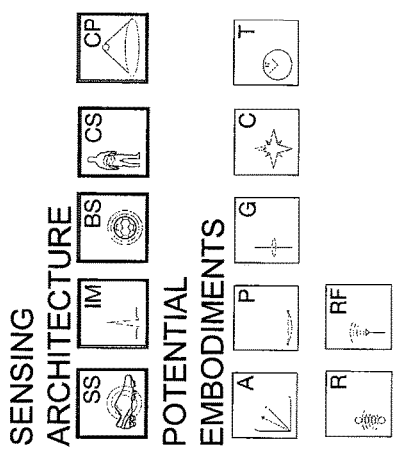
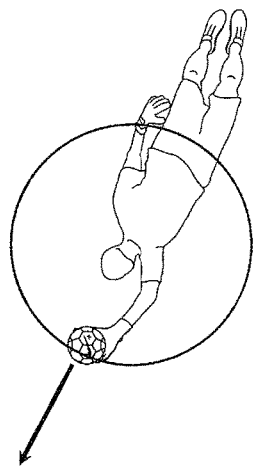
FIG. 68
1: Keeper parry's ball out of bounds
2: Opposition player places corner
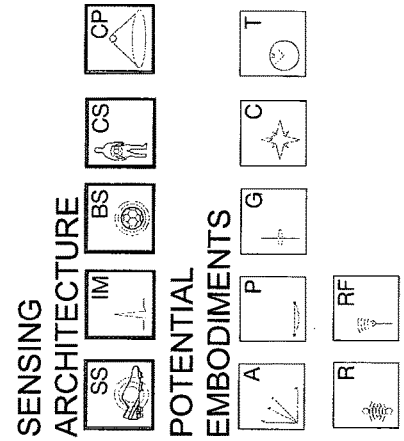
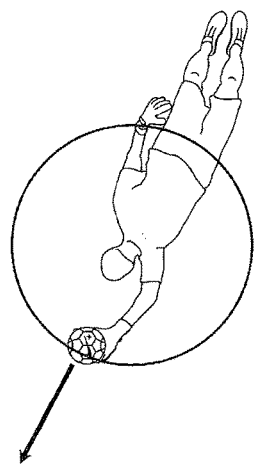
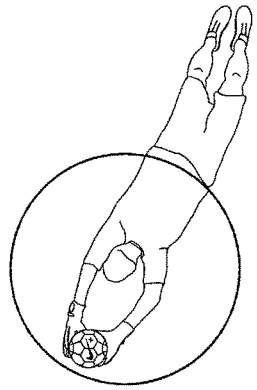
FIG. 69
1: Keeper catches the ball cleanly
2: Keeper unable to catch ball so parry's ball out of bounds

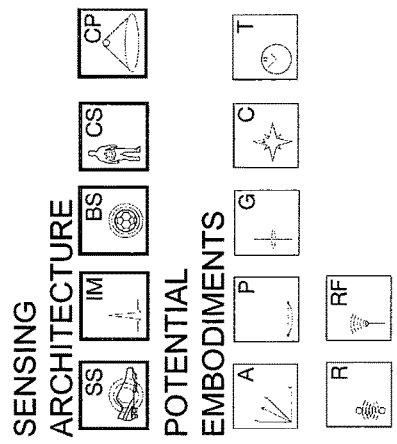
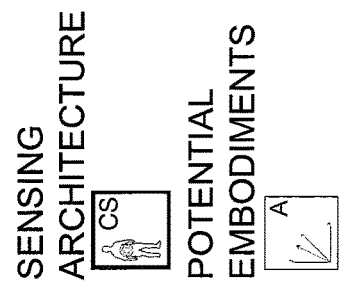
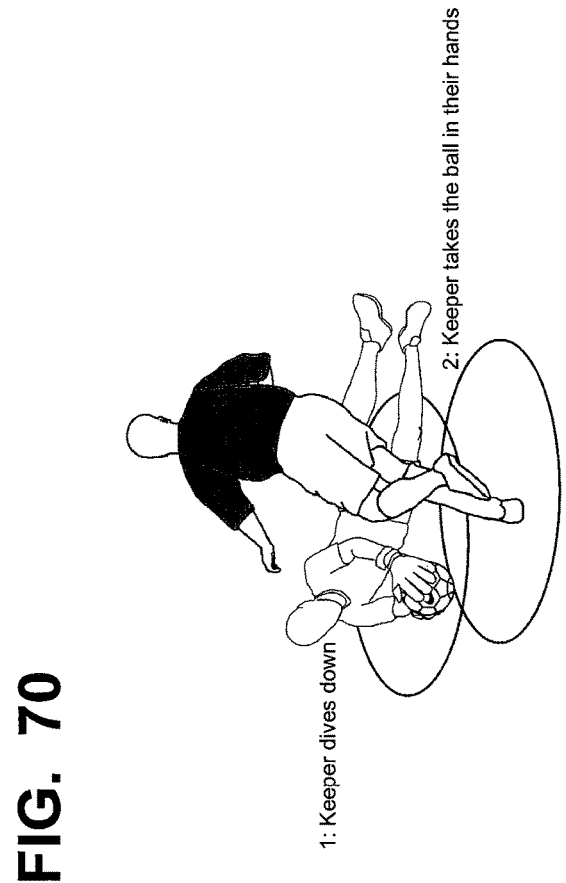
FIG. 70
1: Keeper dives down
2: Keeper takes the ball in their hands
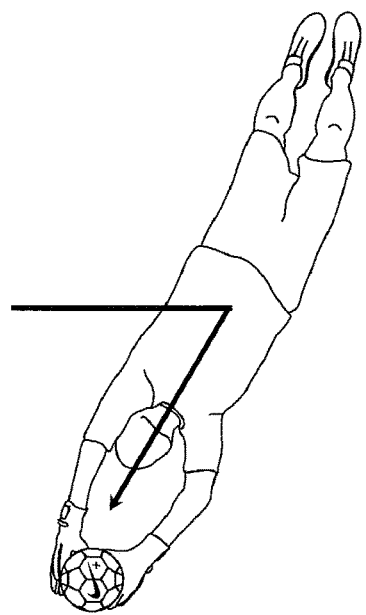
FIG. 71

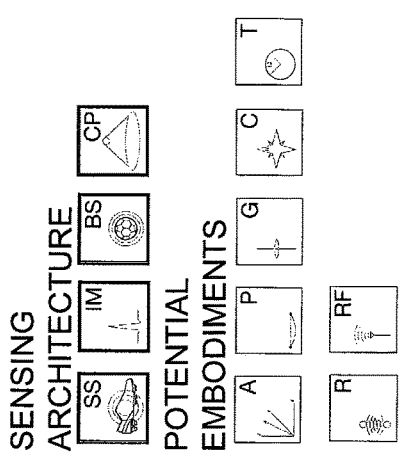
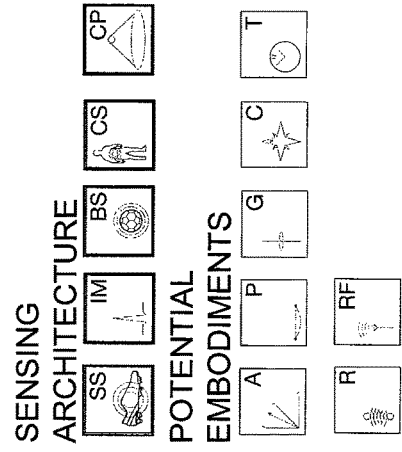
FIG. 72
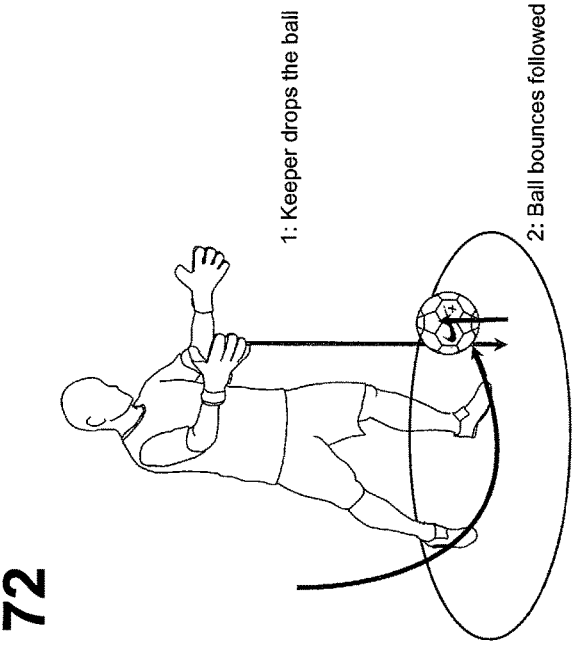
1: Keeper drops the ball
2: Ball bounces followed by kick event
FIG. 73
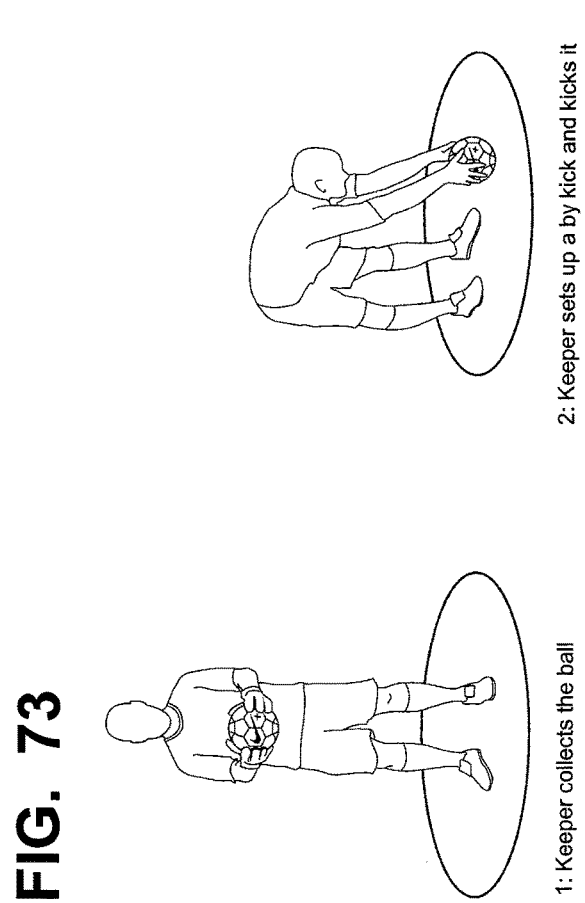
1: Keeper collects the ball
2: Keeper sets up a by kick and kicks it

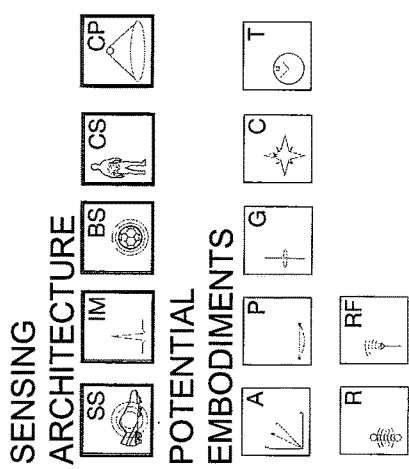
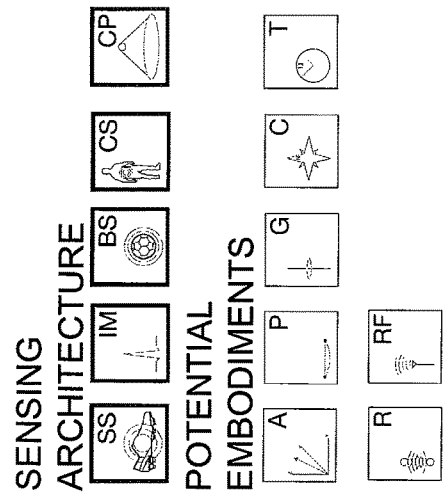
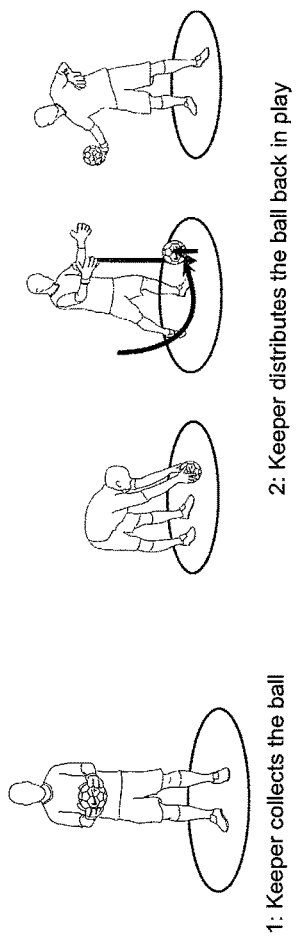
FIG. 74
1: Keeper collects the ball
2: Keeper distributes the ball back in play
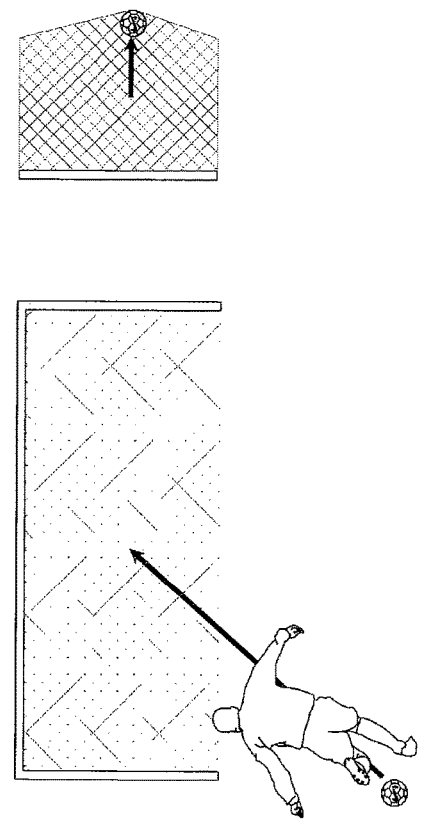
FIG. 75

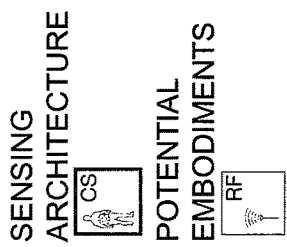
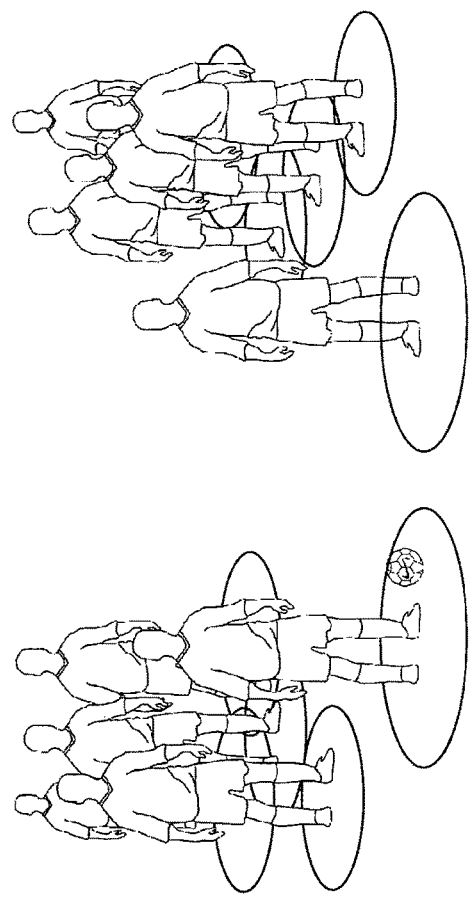
FIG. 76
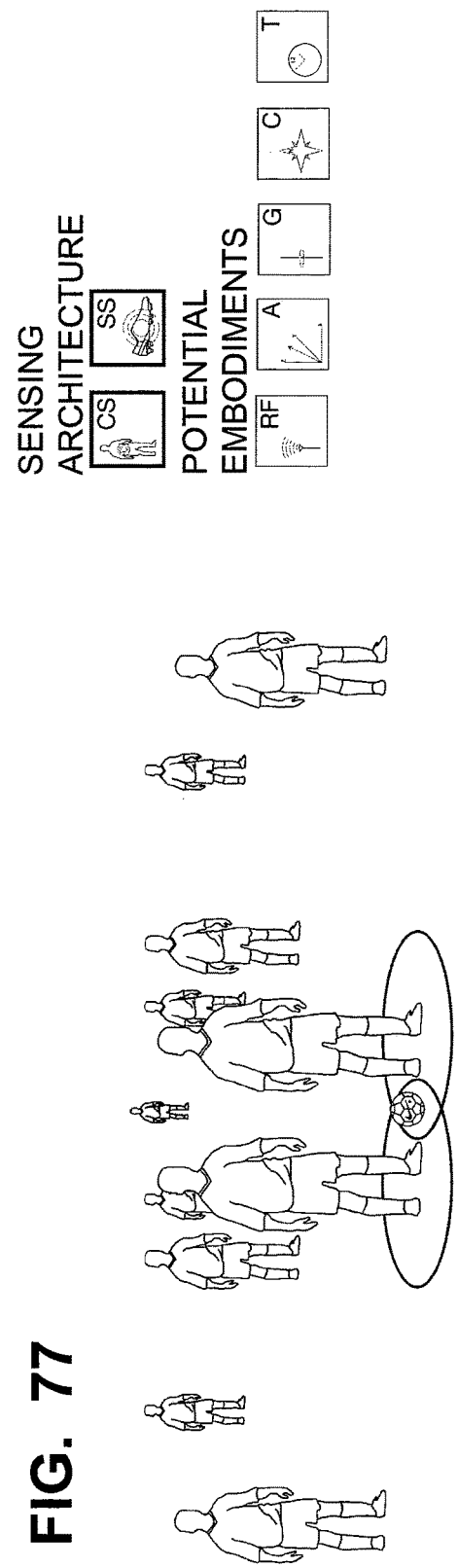
FIG. 77

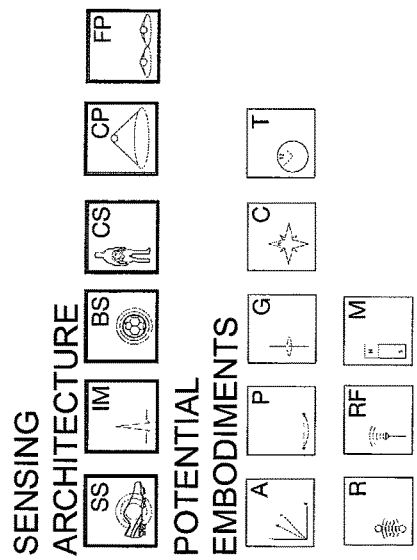
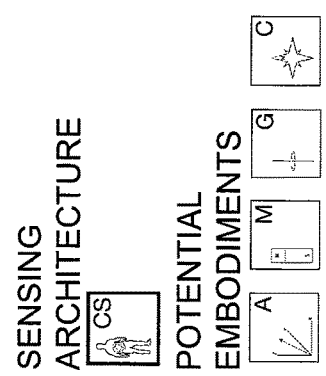
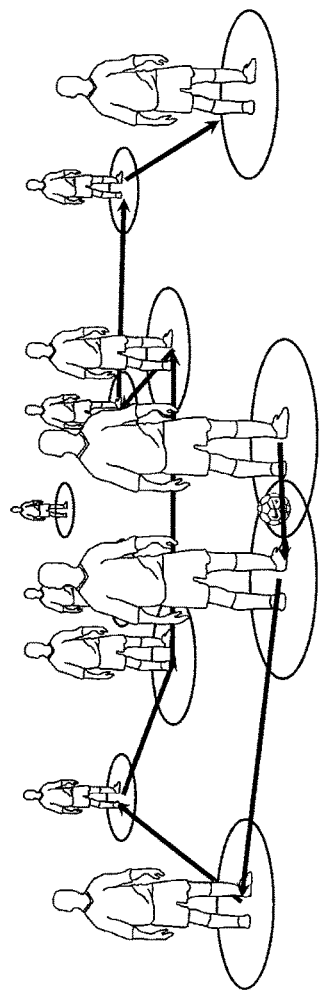
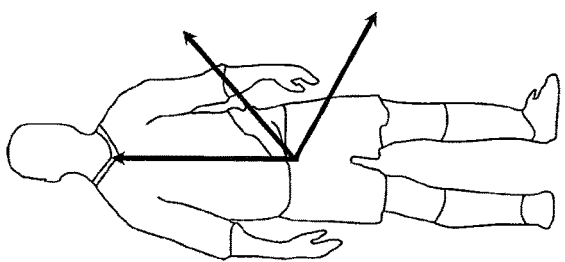
FIG. 80
FIG. 81

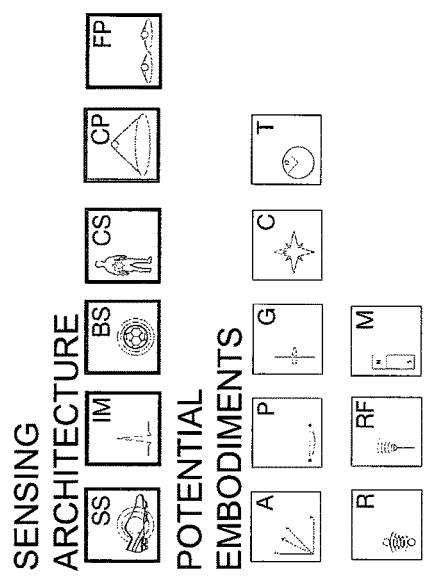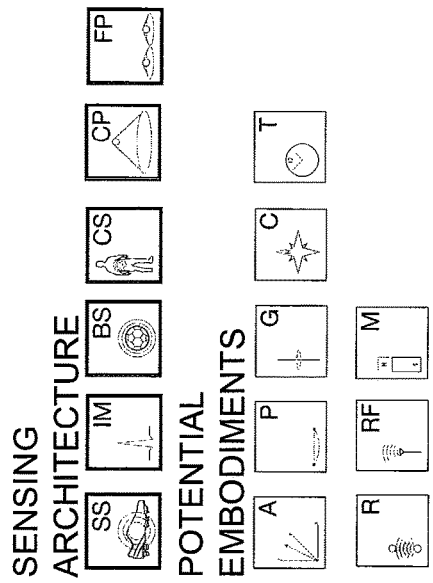
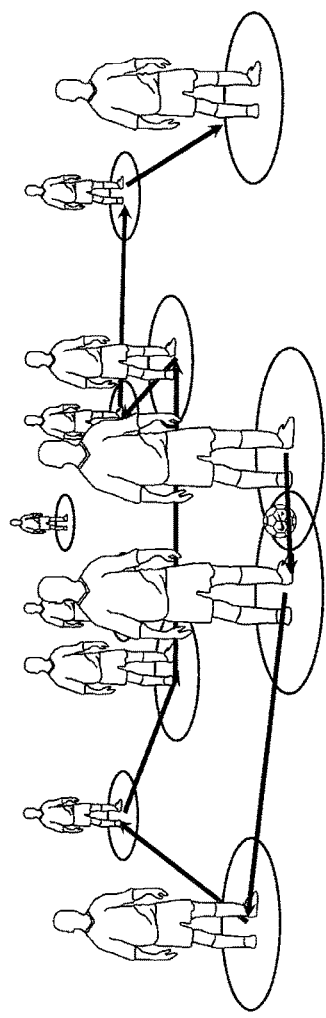
FIG. 82
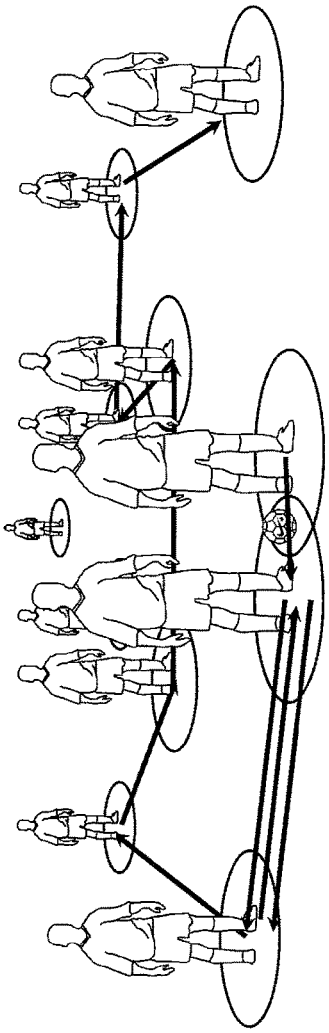
FIG. 83

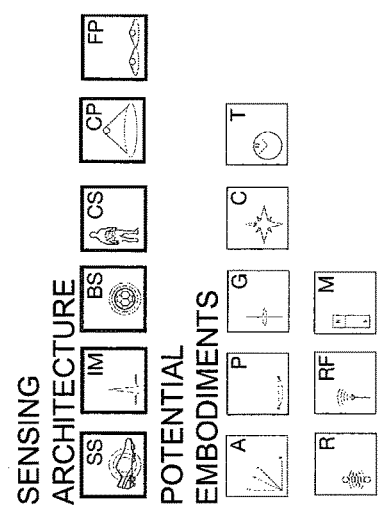
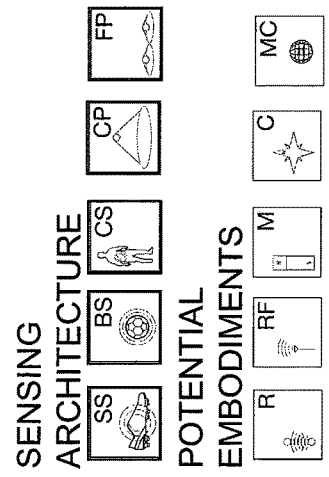
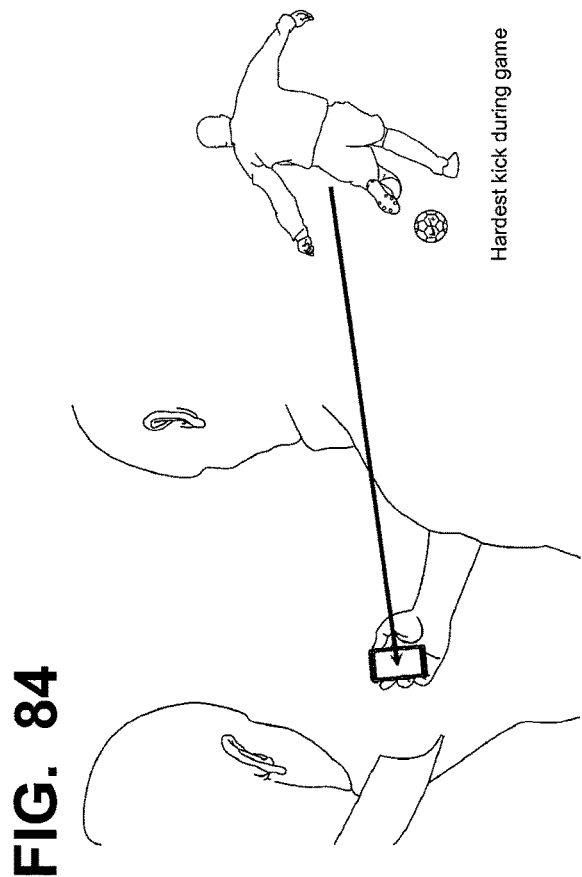
FIG. 84
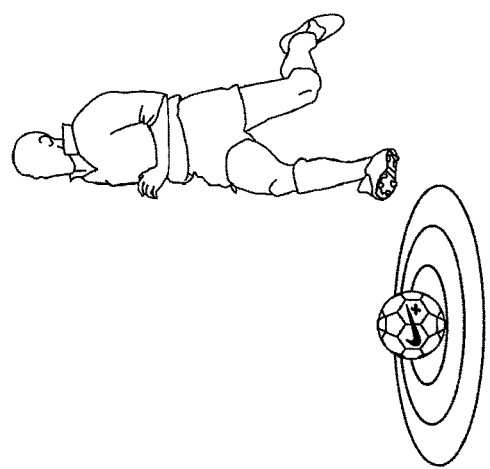
FIG. 85

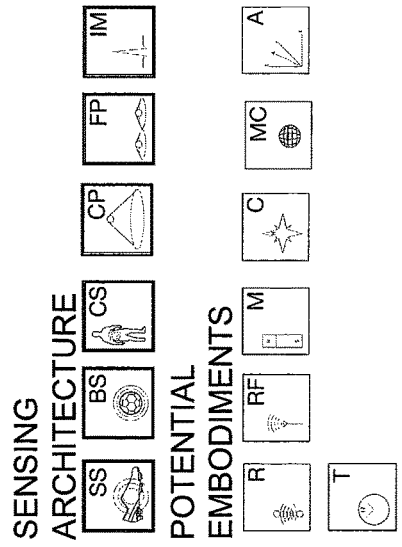
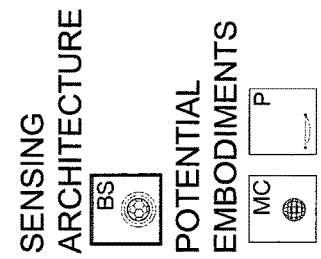
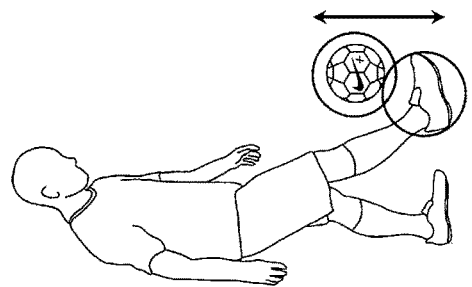
FIG. 86
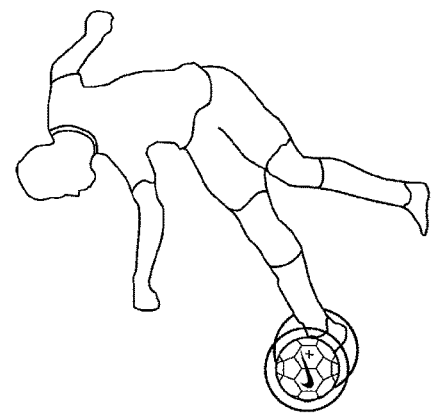
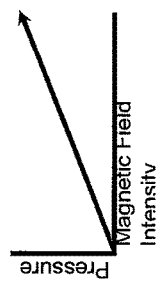
FIG. 87

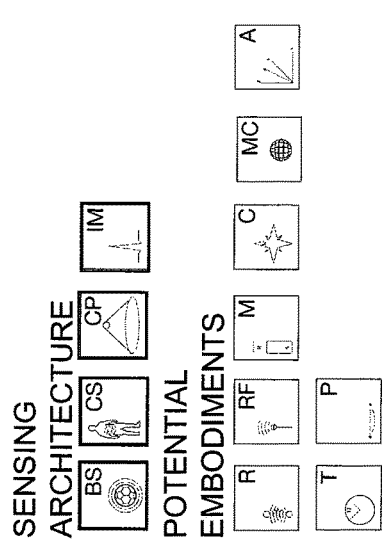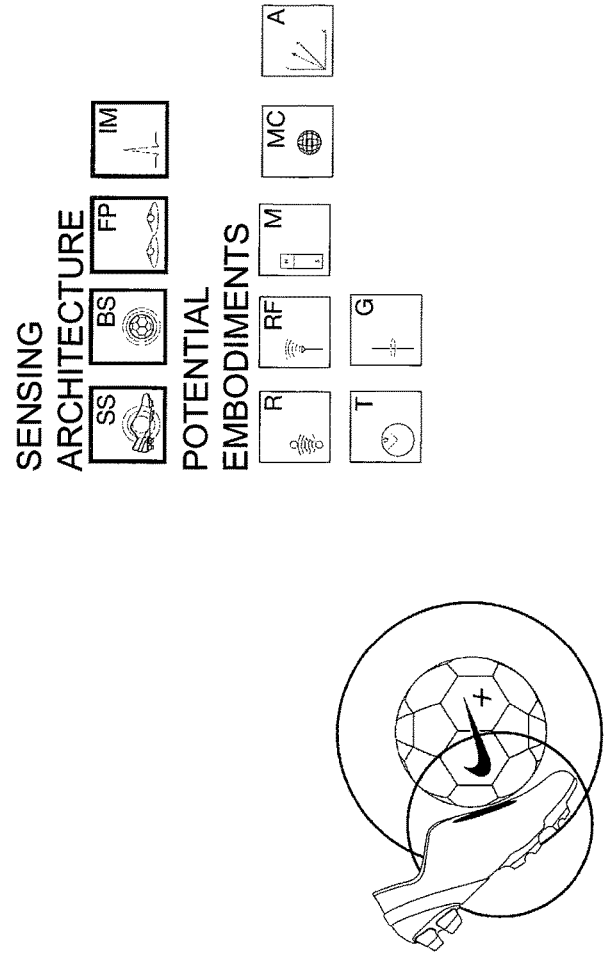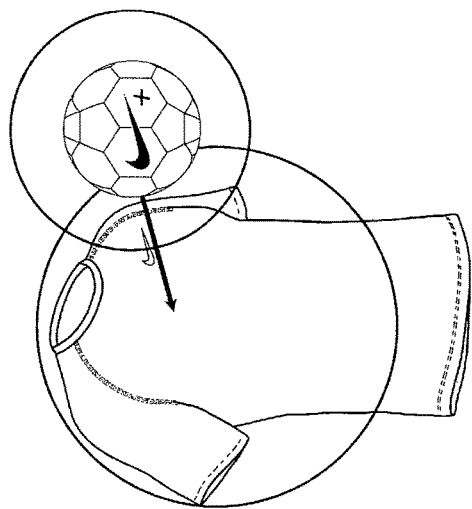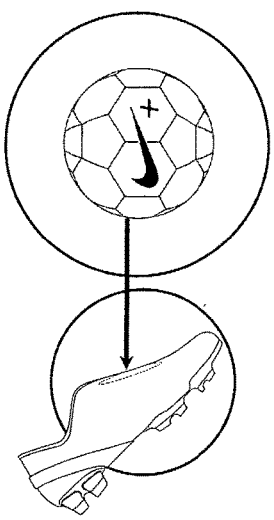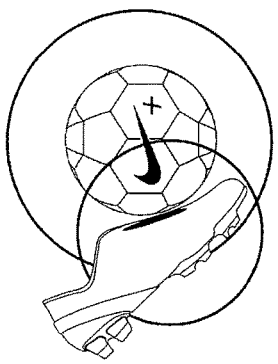
FIG. 88
FIG. 89

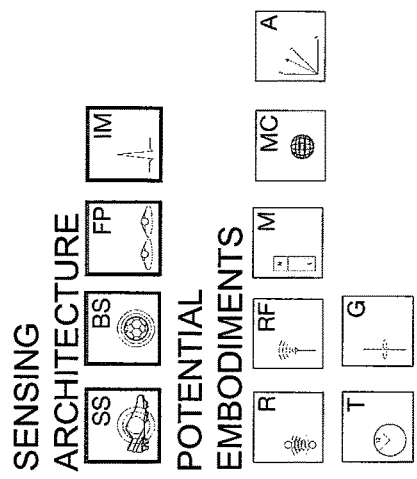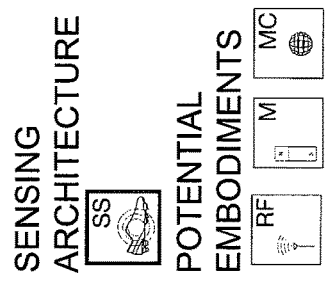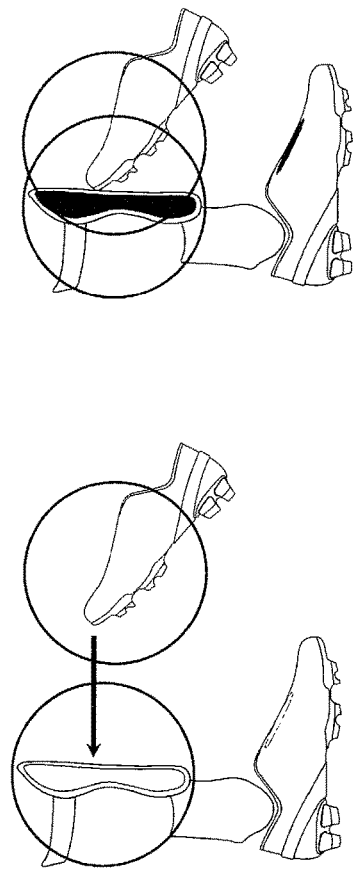
FIG. 90
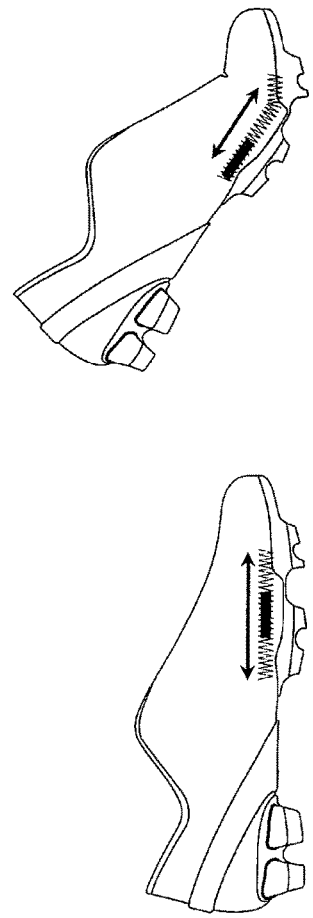
FIG. 91

FIG. 92
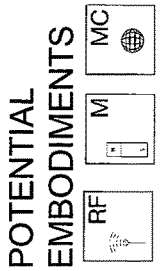
SENSING ARCHITECTURE
POTENTIAL EMBODIMENTS
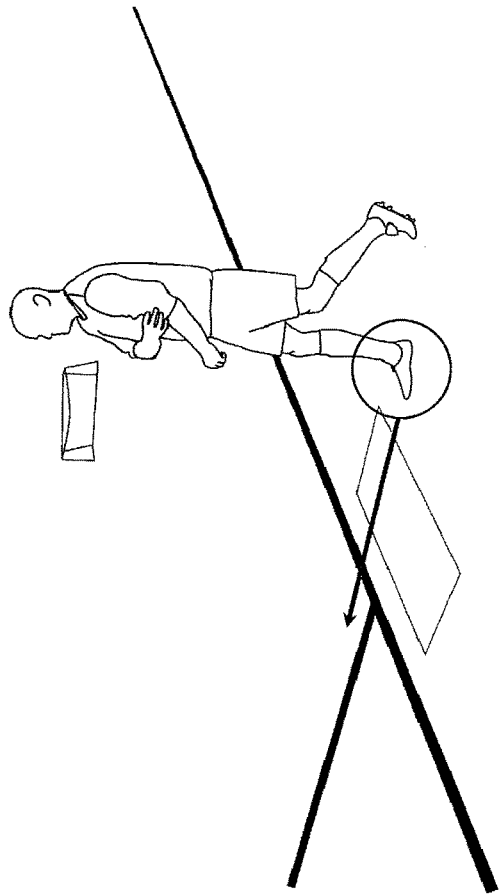
FIG. 93
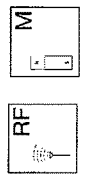
SENSING ARCHITECTURE
POTENTIAL EMBODIMENTS
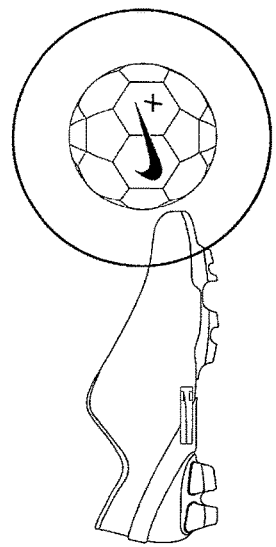
2: Ball comes near and switch is pulled up to strike contact showing proximity to ball
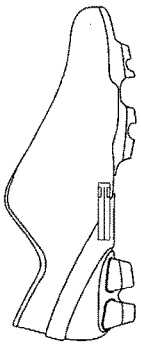
1: Magnet switch is in rest position

ATHLETIC PERFORMANCE MONITORING SYSTEMS AND METHODS IN A TEAM SPORTS ENVIRONMENT

RELATED APPLICATION DATA

This application is a continuation of co-pending U.S. patent application Ser. No. 14/845,993 filed Sep. 4, 2015, which is a continuation of U.S. patent application Ser. No. 12/630,737 entitled "Athletic Performance Monitoring Systems and Methods in a Team Sports Environment" and filed Dec. 3, 2009, the entire disclosure of which is hereby incorporated by reference and which in turn claims priority benefits based on: (a) U.S. Provisional Patent Appln. No. 61/200,953 filed Dec. 5, 2008 and entitled "Athletic Performance Monitoring Systems and Methods in a Team Sports Environment" and (b) U.S. Provisional Patent Appln. No. 61/186,740 filed Jun. 12, 2009 and entitled "Athletic Performance Monitoring Systems and Methods in a Team Sports Environment." These earlier provisional patent applications are entirely incorporated herein by reference.

FIELD OF THE INVENTION

The present invention relates to systems and methods for monitoring player performance during athletic activities (e.g., during a game, a practice session, a workout, etc.), including team oriented athletic activities. Such systems and methods may be useful for evaluating performances of one or more players in various team sporting activities, such as soccer, basketball, American football, hockey, rugby, field hockey, lacrosse, baseball, cricket, volleyball, badminton, and the like. The systems and methods may be used by the individual as a measuring stick and motivation to improve, as well as by coaches or trainers.

BACKGROUND

Many systems are available for measuring features of athletic performance. For example, many gyms and fitness centers are equipped with specialized systems that help track a user's use of the machines (e.g., card readers, RFID equipment, etc.). The usage data may be automatically generated and downloaded to a central computer system and made available for the athlete's review. One disadvantage of such systems is that their use is confined to use with specialized equipment within the "four walls" of the gym or fitness center.

The NIKE+™ athletic performance monitoring system (available from NIKE, Inc. of Beaverton, Oreg.) provides a convenient system and method that allows individuals to measure and collect data relating to ambulatory exercise, such as walking or running. Data collection using a NIKE+™ system is not confined to any specific geographic location. Rather, the system can be used at any desired locations, both indoor and outdoor.

Not all personal exercise and athletic endeavors, however, are limited to walking and running. Many individuals participate in team games, such as soccer, basketball, football, and the like. At present time, there is no easy or convenient system that is useful to automatically collect, compile, and store data that accurately and empirically depicts a player's efforts when participating in these team sports. Such systems would be useful to help a player gauge his or her performance, to help a player identify areas where improvement may be achieved, and to help a player recognize when improvement has been achieved. Additionally, such systems would be useful tools for coaches and trainers, to help them ascertain each individual's strengths and weaknesses and to help them field the best combination of players for a given game situation (e.g., a "scoring" team, a "defense" team, etc.). Moreover, such systems could provide enormous motivation for the athlete by enabling the athlete (or others) to set performance goals and/or challenges.

SUMMARY OF THE INVENTION

The following presents a general summary of aspects of the present invention in order to provide a basic understanding of the invention and various example features of it. This summary is not intended to limit the scope of the invention in any way, but it simply provides a general overview and context for the more detailed description that follows.

Aspects of this invention relate to systems, methods, and computer-readable media with computer-executable instructions stored thereon for performing methods and/or operating user interfaces relating to the monitoring of player performance during athletic activities (e.g., during a game, a practice session, a workout, etc.), including team oriented athletic activities.

Additional aspects of this invention relate to systems and methods for sensing and monitoring various athletic performance metrics, e.g., during the course of a game, a practice, a training session, training drills, and the like.

Systems in accordance with at least some examples of this invention may include systems for monitoring performance parameters of one or more athletes in a team sport setting. Such systems may include one or more of: (a) a sensor system for monitoring one or more of: (i) a first parameter correlated to a first player's movement speed during a first time period, (ii) a second parameter correlated to a determination of when the first player possesses the ball and when the first player does not possess the ball during the first time period, and (iii) a third parameter correlated to the first player's ball transfer speed, force, or power during the first time period; (b) a data storage system for storing data collected by the sensor system relating to the first, second, and third parameters; (c) a processor system for receiving and processing data stored in the data storage system; and (d) an output device for outputting user perceptible output including athletic performance metric information based on the collected and stored data.

As some additional examples, athletic performance monitoring systems according to at least some examples of this invention may include: (a) at least one sensor system selected from the group consisting of: a radar based sensor system, a radio or radio frequency based sensor system, a global positioning satellite based sensor system, a magnet based sensor system, a magnetic coil based sensor system, a pressure sensor system, an accelerometer sensor system, a gyroscope based sensor system, a time sensor or clock, and a compass, wherein at least one of the at least one sensor system is provided in or on an article of apparel, an article of footwear, a ball, or a hockey puck; (b) means for receiving output from the at least one sensor system; and (c) processing means program and adapted to determine or sense, based on the output received at the means for receiving, data relating to at least one event, metric, or feature selected from the group consisting of: a player receiving possession of the ball or puck; player possession of the ball or puck; a player's speed while in possession of the ball or puck; one or more characteristics of dribbling the ball; a knock on and sprint event; close control of the ball or puck; dribble foot distribution; control of an incoming ball or puck; a one touch pass event; a tackle avoided event; a successful tackle event; a skin event; a ball or puck possession or proximity heat map; a player intensity metric; boot kick zone information; ball or puck flight path distribution or information; longest kick or hit information; ball or puck flight elevation angle information; kick type distribution information; kick or shot power information; kick or pass style information; kick or shot power information at a predetermined threshold movement speed; pass accuracy information at a predetermined threshold movement speed; volley information; a free kick award event; information distinguishing a free kick from a penalty kick; a set piece event; a set piece save event; information for determining whether a set piece kick is on goal; player movement direction information based on body angle; a player turn in event; a player turn in event when in possession of or proximity to the ball; player movement direction or type; information regarding an amount of time a player spends on his or her toes; player posturing or player facing direction; man-to-man opposing position information; information relating to a player's ability to draw opposition; information regarding a player's speed in breaking away from defensive players; a successful pass event; a pass interception event; a give and go event; information relating to a ball or puck pass that passes in proximity to a defensive player but continues on to complete a successful pass; pass direction distribution information; pass player distribution information; information indicating an out of bounds event; information indicating an intentional out of bounds event; information identifying a goal keeper; information identifying a scored goal; information identifying a save; information identifying a keeper parry event; information identifying a keeper parry event with respect to a ball speed above a predetermined threshold amount; information identifying a keeper advance or tackle event; information identifying a player dive or a player jump event, and optionally, a jump height associated with the jump event; information identifying a drop kick event; information identifying a shot on goal that goes out of bounds; information identifying a shot on goal; an automatic pick of team captains; an automatic pick of team goal keepers; an automatic pick of teams; information indicating a game start; information for automatically identifying a direction of play for a team or an individual player; information for automatically identifying an individual player's teammates or an entire team based on pass distribution information; information for automatically identifying an individual player's teammates or an entire team based on player orientation; information for automatically identifying an individual player's teammates or an entire team based on an object's orientation, wherein each player carries an object that is oriented in a first predetermined manner to indicate players on one team; team identification using pre-game ball proximity or passing information; information regarding magnetic characteristics of a ball; ball juggling information; ball pressure information as a function of magnetic field strength associated with the ball; ball proximity to an article of apparel; information for changing a state of magnetic fluid contained in a shoe based on proximity to a ball or puck; information for change a state of an article of protective gear based on proximity to a foot; information relating to running state based on magnetic properties of an article of footwear; information regarding entering a playing field based on sensing a magnetic field; ball possession time information based on reaction of a magnetic switch sensor states within a shoe to a magnetic field generator within a ball or puck; information relating to a player on-field location heat map; information relating to player explosiveness; and information relating to whether a ball is being thrown or kicked.

Additional aspects of this invention relate to methods of operating athletic performance monitoring systems of the types described above, as well as to athletic performance monitoring methods that determine or sense data relating to at least one event, metric, or feature described above, e.g., using the various systems described above. Still additional aspects of this invention relate to user perceptible output systems, including graphical user interfaces displayed on computer devices, that provide output information to users of systems and methods according to this invention.

BRIEF DESCRIPTION OF THE DRAWINGS

The present invention is illustrated by way of example and not limited in the accompanying figures, in which like reference numerals indicate the same or similar elements throughout, and in which:

FIGS. 19A and 19B illustrate various features that assist in explaining differences in detector response for throwing actions v. kicking actions in accordance with examples of this invention;

Figure 1:
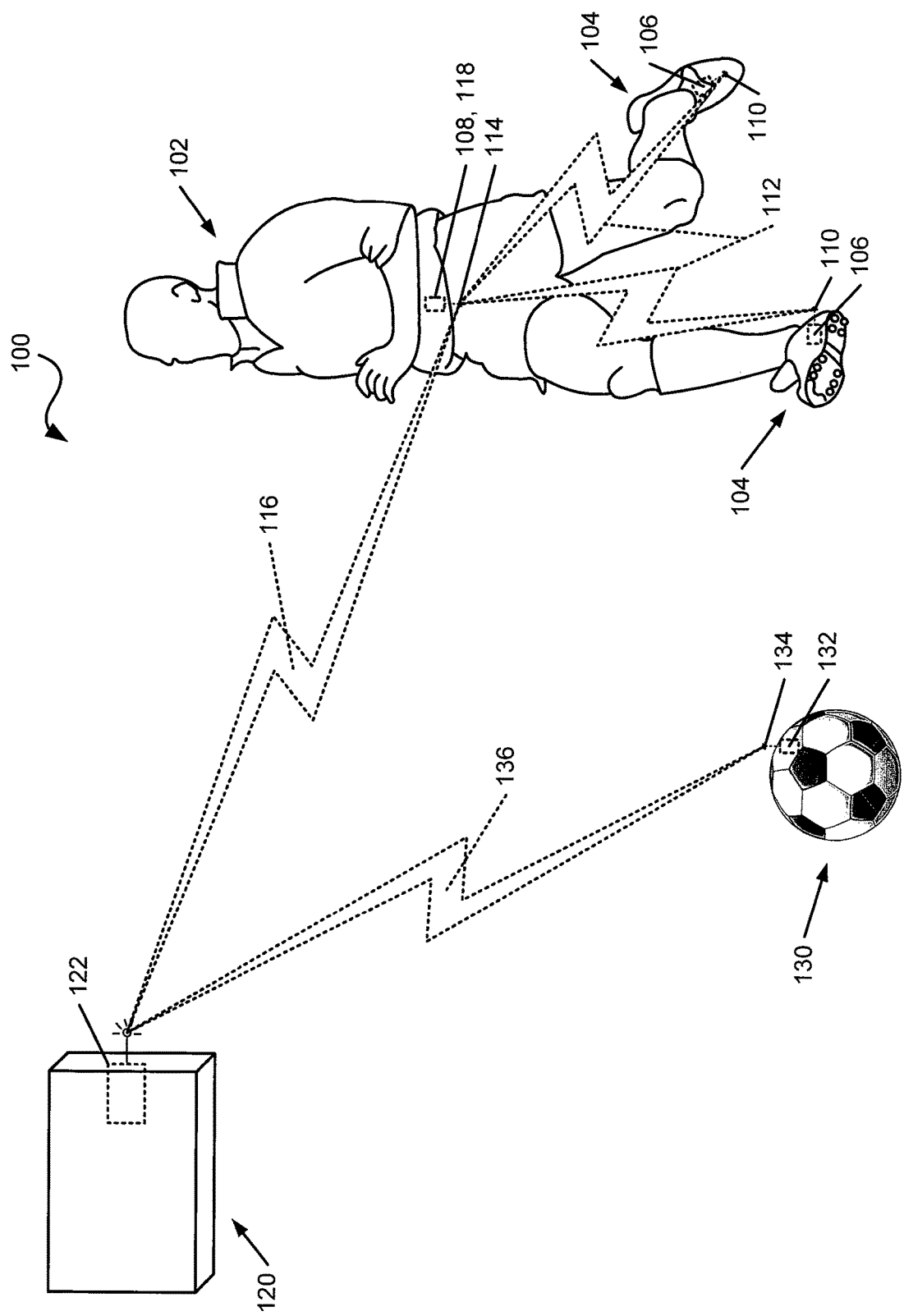
FIG. 1 generally illustrates the components and features of one example athletic performance monitoring system in accordance with this invention.

The reader is advised that the various parts shown in these drawings are not necessarily drawn to scale.

DETAILED DESCRIPTION

The following description and the accompanying figures disclose features of systems, methods, computer-readable media, and user interfaces in accordance with examples of the present invention.

I. GENERAL DESCRIPTION OF SYSTEMS, METHODS, AND USER INTERFACES IN ACCORDANCE WITH THIS INVENTION

Aspects of this invention relate to systems, methods, and computer-readable media with computer-executable instructions stored thereon for performing methods and/or operating systems and/or user interfaces relating to the monitoring of player performance during an athletic activity (e.g., during a game, a practice session, a workout, etc.), including team oriented athletic activities.

Systems in accordance with at least some examples of this invention may include systems for monitoring performance parameters of one or more athletes in a team sport setting (e.g., in a game, during practice, as part of a workout program, etc.). Any desired type of team sport may be involved without departing from this invention, such as soccer, basketball, American football, hockey, rugby, field hockey, lacrosse, baseball, cricket, volleyball, badminton, tennis, and the like. Such systems may accumulate data relating to one individual on a team, to multiple individuals on one team, and/or to one or more individuals on each participating team.

As some more specific examples, systems in accordance with at least some examples of this invention may include systems for monitoring athletic performance(s) that include: (a) a sensor system for monitoring one or more of: (i) a first parameter correlated to a first player's movement speed during a first time period, (ii) a second parameter correlated to a determination of when the first player possesses the ball and when the first player does not possess the ball during the first time period, and (iii) a third parameter correlated to the first player's ball transfer speed, force, or power during the first time period; and (b) a data storage system for storing data collected by the sensor system relating to the first, second, and third parameters. The term "ball," as used herein, constitutes any item used in sporting activities that is possessed, thrown, batted, kicked, hit, or otherwise propelled by the athletes in order to achieve a desired goal of the game. In addition to objects that are substantially round or spherical, such as soccer balls, basketballs, field hockey balls, lacrosse balls, baseballs, volleyballs, tennis balls, and cricket balls, the term "ball," when used generically herein, further includes other sport related objects, such as hockey pucks, America footballs, rugby footballs, badminton birdies, and the like.

Systems in accordance with at least some examples of this invention further may include: a processor system for receiving and processing data stored in the data storage system; and an output device (such as an audio device; a video device; an alpha-numeric display device; a computer monitor; a display screen from other electronic devices, such as cellular telephones, watches or other wrist borne devices, portable electronic devices, etc.) for generating a user perceptible output.

Based on the sensed data, systems and methods in accordance with this invention may determine any desired data associated with the athletic performance. As some more specific examples, systems and methods in accordance with examples of this invention may determine one or more of the following performance metrics for one or more of the players participating in an athletic activity: a player's maximum movement velocity during a desired time period; a player's average movement velocity during a desired time period; a player's time correlated movement velocity during a desired time period; a number of times that a player's movement velocity exceeded a predetermined threshold value during a desired time period; an amount of time that a player possessed the ball during a desired time period; an amount of time that a player was located within a predetermined distance from the ball during a desired time period; a player's movement velocity when in possession of the ball during a desired time period; a player's maximum movement velocity when in possession of the ball during a desired time period; a player's average movement velocity when in possession of the ball during a desired time period; a player's time correlated movement velocity when in possession of the ball during a desired time period; a player's ball transfer speed, force, or power (e.g., kick speed, pass speed, throw speed, shot speed, etc.) during a desired time period; a player's maximum ball transfer speed, force, or power during a desired time period; a player's overall movement distance during a desired time period; a player's overall movement distance while in possession of the ball during a desired time period; a number of times that a player possessed the ball during a desired time period; a number of times that a player was located within a predetermined distance from the ball during a desired time period; a number of times that a player contacted the ball during a desired time period; one or more performance goals for a player; whether a player has achieved a performance goal; and a revised performance goal for a player.

The output system associated with systems and methods according to this invention may output information relating to a player's athletic performance in any desired form, format, or manner (e.g., in any user perceptible manner). For example, the output system may output audio, video, alpha-numeric, tactile, and/or graphical information (including through a graphical user interface) relating to any of the performance metrics described above.

Methods for monitoring athletic activities of the types described above may include one or more of the following steps: (a) sensing data relating to one or more of: (i) a first parameter correlated to a first player's movement speed during a first time period, (ii) a second parameter correlated to a determination of when the first player possesses the ball and when the first player does not possess the ball during the first time period, and (iii) a third parameter correlated to the first player's ball transfer speed, force, or power during the first time period; (b) storing the data relating to the first, second, and third parameters; (c) calculating or determining one or more athletic performance metrics based on the sensed or stored data; and (d) generating a user perceptible output that includes information relating to one or more of the calculated or otherwise determined athletic performance metrics. The performance metrics may be any of the various types described above. The user perceptible output may be in any of the various forms or formats described above (e.g., audio, video, alpha-numeric, tactile, and/or graphical information).

When the athletic performance of multiple participants is tracked, the "time periods" for the tracking may be the same or different without departing from this invention. For example, the sensors may collect data for each player only during the time period that the player is actually actively in the game (e.g., when the player is not on the bench). The time period(s) may span one or more games or practice sessions, or they may involve only portions of games or practice sessions. Also, the time period may involve continuous or discontinuous blocks of time (e.g., if a player goes in and out of a game, the sensors may sense the player's activity over the course of the entire game as a single "time period," but only while the player is actively involved in the game).

Additional aspects of this invention relate to generating user perceptible output relating to athletic performance metrics measured and/or determined by systems and methods in accordance with this invention. In some examples, this output may be in the form of a graphical user interface generated on a computer-controlled display device (such as a computer monitor, a display screen for a cellular telephone or other portable electronic device, other audio and/or video display devices, etc.). Such aspects of the invention may include computer-readable media (such as a computer memory, like a hard disk drive, a portable computer memory device, and the like) including computer-executable instructions stored thereon for generating a graphical user interface on a display device, wherein the graphical user interface includes one or more of: (a) a display portion containing information relating to a player's movement speed during a desired time period of an athletic performance activity; (b) a display portion containing information relating to a player's ball possession during a desired time period; (c) a display portion containing information relating to a player's ball transfer speed, force, or power during a desired time period; (d) a display portion containing information relating to a player's maximum movement speed during a desired time period; (e) a display portion containing information relating to a player's maximum movement speed while in possession of the ball during a desired time period; (f) a display portion containing information relating to a number of times that a player's movement speed or power exceeded a predetermined threshold during a desired time period; and (g) a display portion containing information relating to a number of times that a player possessed or contacted a ball during a desired time period. Two or more of the various display portions may be displayed simultaneously, or one may access information contained in some of the display portions through interaction with an element provided in another of the display portions.

Given the general description of various example features and aspects of the invention provided above, more detailed descriptions of various specific examples of athletic performance monitoring systems, methods, computer-readable media, and user interfaces according to the invention are provided below.

II. DETAILED DESCRIPTION OF SPECIFIC EXAMPLES OF FEATURES OF ATHLETIC PERFORMANCE MONITORING SYSTEMS AND METHODS ACCORDING TO THE INVENTION

The following discussion and accompanying figures describe various example systems, methods, and computer-readable media with computer-executable instructions stored thereon for performing methods, operating systems, and generating user perceptible output relating to the monitoring of player performance during an athletic activity (e.g., during a game, a practice session, a workout, etc.), including team oriented athletic activities. When the same reference number appears in more than one drawing, that reference number is used consistently in this specification and the drawings to refer to the same or similar parts or elements throughout.

Initially, example hardware for operating systems and performing methods in accordance with this invention will be described. Then, a more detailed explanation of examples of performance monitoring and performance metric determination will be described. Example features of use of systems and methods in accordance with this invention in a multi-user atmosphere will be described. Additionally, features of an example user interface for providing user feedback and information will be described.

A. Example Hardware Systems

FIG. 1 generally illustrates features of example hardware components that may be included in an athletic performance monitoring system 100 in accordance with this invention. First, the system 100 may include one or more sensors that are carried by the athlete 102 during the course of the game, practice session, or the like (generically referred to herein as an "athletic performance" or "athletic activity"). As some more specific examples, one or more of the athlete's shoes 104 may carry a sensor 106 therein. As will be described in more detail below, the shoe sensors 106 may be used, at least in part, to measure various athletic performance metrics, such as movement speed, movement distance, on ball movement speed, on ball movement distance, off ball movement speed, off ball movement distance, ball possession time or count, kick speed, etc. The shoe based sensors also may be used to provide a record or identify the player that kicked the ball (optionally while also using data from a ball based sensor). In some example systems and methods according to this invention, the shoe 104 based sensors 106 may measure speed and distance in a manner akin to the measurement of speed and distance in NIKE+™ athletic performance monitoring systems available from NIKE, Inc. of Beaverton, Oreg. (e.g., pedometer based speed and/or distance type information).

If desired, the foot mounted sensors 106 may transmit relevant data back to a receiver 108 also worn by the athlete 102. While the data may be transmitted in any desired manner, FIG. 1 generally illustrates a wireless type transmission, as shown by transmission elements 110, transmission icons 112, and receiver element 114. Any desired wireless or wired transmission system and method may be used without departing from this invention, including the use of any desired wired or wireless data transmission format or protocol, including the transmission systems and protocols currently in use in NIKE+™ athletic performance monitoring systems.

The receiver 108 receives the data from the one or more shoe mounted sensors 106 and stores this data and/or transmits it to an input system 122 provided in a remote computer system 120. This can be accomplished in real time, during the athletic performance, if desired. FIG. 1 illustrates that the receiver 108 includes a transmission system (i.e., transceiver element 114), and the actual data transmission procedure is represented in FIG. 1 by transmission icon 116.

The remote computer system 120 may be any desired type of computer system, at any desired location, without departing from this invention. For example, the transmission system 114 may transmit over the internet to a remotely located server or other computer system 120, e.g., via cellular telecommunications systems or other wireless publicly or privately available data transmission systems. As other examples, the transmission system 114 may transmit to a sideline based or coaches' box based computer system 120, including to hand-held or portable computer systems 120, like those available in cellular telephones, personal digital assistants, and the like. In this way, the coach, trainer, or athlete 102 (or others) can readily have the collected data available for review and use, even in real time during the athletic performance.

The on-body receiver 108 further may include one or more sensor devices 118, if desired. For example, as will be explained in more detail below, the sensor device(s) 118 may constitute a body core mounted accelerometer that may be useful in determining player acceleration, player movement velocity, player movement distance, on ball movement speed, off ball movement speed, vertical displacement (up or down), and the like. The on-body receiver 108 sensor device(s) 118 also may be useful for sensing the ball, for determining metrics like ball proximity/possession time, on ball speed, on ball acceleration, off ball speed, off ball acceleration, etc. If desired, the body core sensor device(s) 118 may be utilized and the shoe based sensor device(s) 106 may be eliminated (or vice versa). As another example, if desired, the shoe based sensor device(s) 106 may directly transmit to computer system 120, without the intermediate transmission to an on-body receiver 108.

In systems and methods in accordance with at least some examples of this invention, the ball 130 also may include one or more sensors 132, a data transmission system 134, or other electronic capabilities (both active and passive). As shown in FIG. 1, the data transmission system 134 of the ball 130 also may transmit data to the remote computer system 120 (e.g., as shown through transmission icon 136). Again, any desired type of transmission system may be used, such as wireless transmission and wireless transmission protocols. As will be described in more detail below, the ball sensor system 132 may be used to provide information useful for determining various metrics such as ball speed, ball location, ball possession (e.g., by ball contact with or proximity to a player), kick speed, kick force, and the like. The ball sensor(s) 132 may include, among other things, one or more accelerometers, gyroscopes, pressure sensors (e.g., piezoelectric sensors, force sensors, etc.), RFID tags, etc. If desired, the ball transmission system 134 could transmit to the receiver 108 in addition to or in place of the transmission to the remote system 120.

Figure 2A:
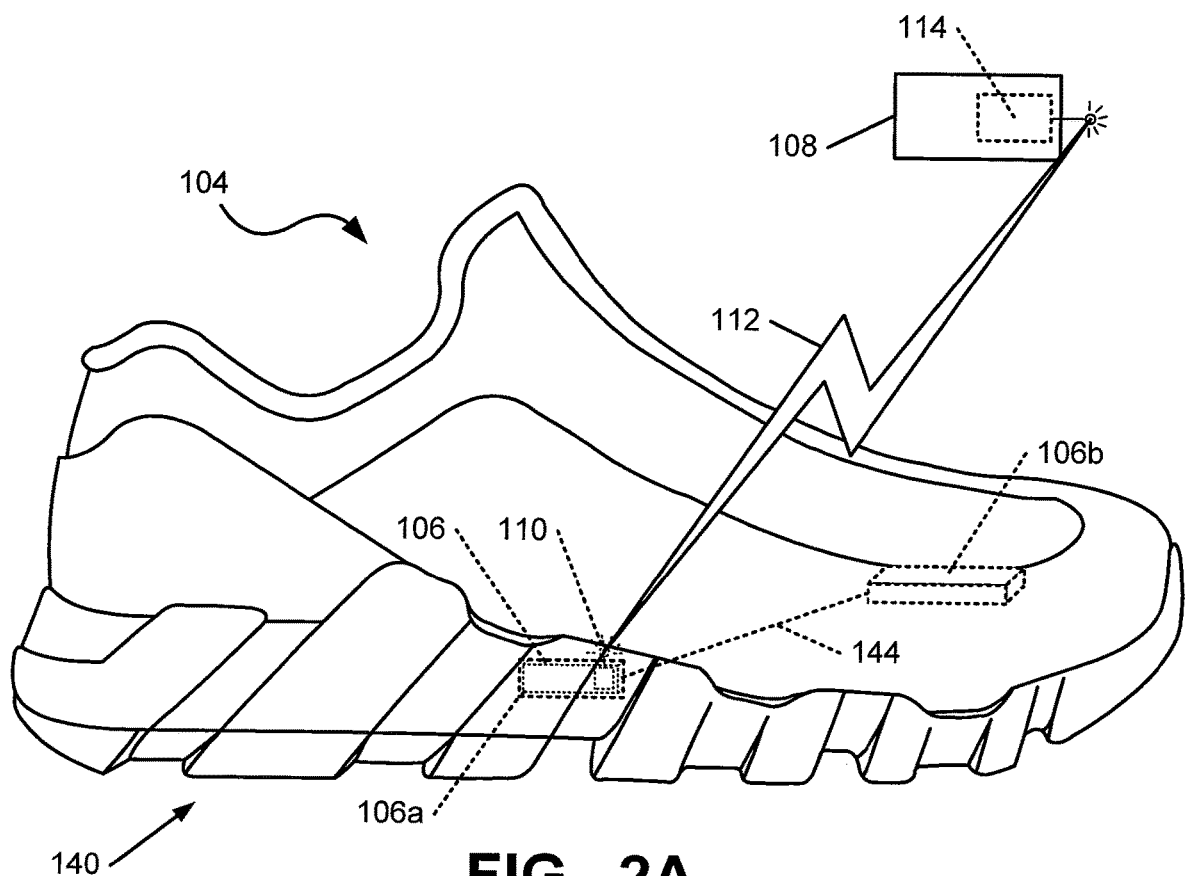
FIGS. 2A through 2E illustrate example features of various products that may be used in athletic performance monitoring systems and methods in accordance with this invention.
Figure 2B:
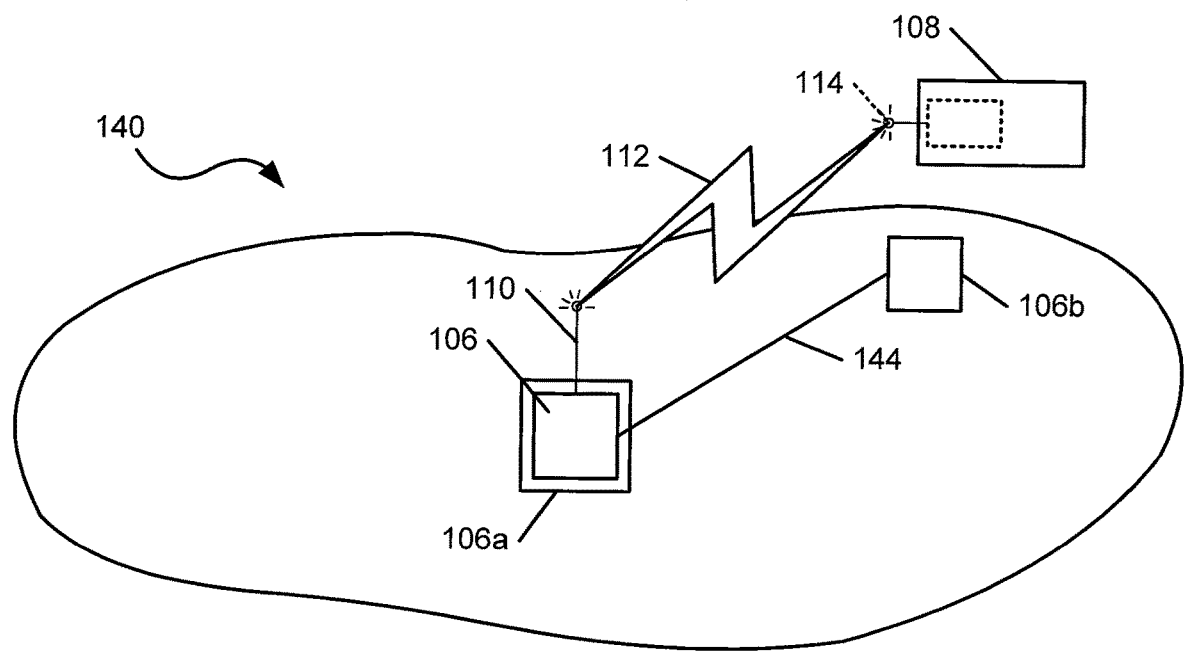

FIGS. 2A and 2B illustrate features of a shoe 104 that may include one or more sensors 106 in accordance with at least some examples of this invention. As shown in these figures, the sole 140 of one or both shoes 104 may include a centrally located housing 106*a* in which sensor 106 is mounted. As noted above, this sensor 106 may be an accelerometer or a pedometer based speed and/or distance type sensor (e.g., a piezoelectric sensor, a force sensor, etc.), and the mounting location and structure may be akin to the mounting of the sensors in NIKE+™ athletic performance monitoring systems available from NIKE, Inc. of Beaverton, Oreg. (e.g., mounted generally in the arch area of the sole 140, within a housing 106*a* defined in the midsole structure and underneath a sock liner or insole member of the shoe 104). Other mounting locations, structures, and arrangements on a shoe 104 (or other foot or leg borne equipment, such as a sock, shin guard, etc.) are possible without departing from this invention.

As further shown in FIGS. 2A and 2B, the shoe 104 may include other sensors, such as sensor 106*b*. This sensor 106*b* (or sensors) may be provided for other purposes, such as detection of contact with the ball 130 (which may correlate to ball possession), detection of kick force, detection of foot acceleration (which may correlate to kick force, ball speed, etc.), or the like, and it may be provided at any desired location on the shoe 104 (e.g., on the exterior, within the construction, on or incorporated into the upper, etc.). The sensor 106*b* may be an accelerometer, a force sensor, a pressure sensor (e.g., a piezoelectric sensor), or the like. Other sensors also may be provided on one or both shoes 104 worn by the athlete 102 without departing from this invention. When sensors are provided on both shoes, these sensors may measure the same or different parameters.

FIGS. 2A and 2B illustrate that the sensor 106*b* is connected to sensor 106 via connection 144, and in this manner, data from both sensor 106 and 106*b* is transmitted to the receiver 108 via transmission system 110, 112, and 114. This is not a requirement. For example, if desired, sensor 106*b* could include its own data storage and/or transmission system for storing data and/or transmitting it to the receiver 108 (or to another remote system, such as remote system 120). Other data storage and/or transmission arrangements also are possible without departing from this invention.

Figure 2E:
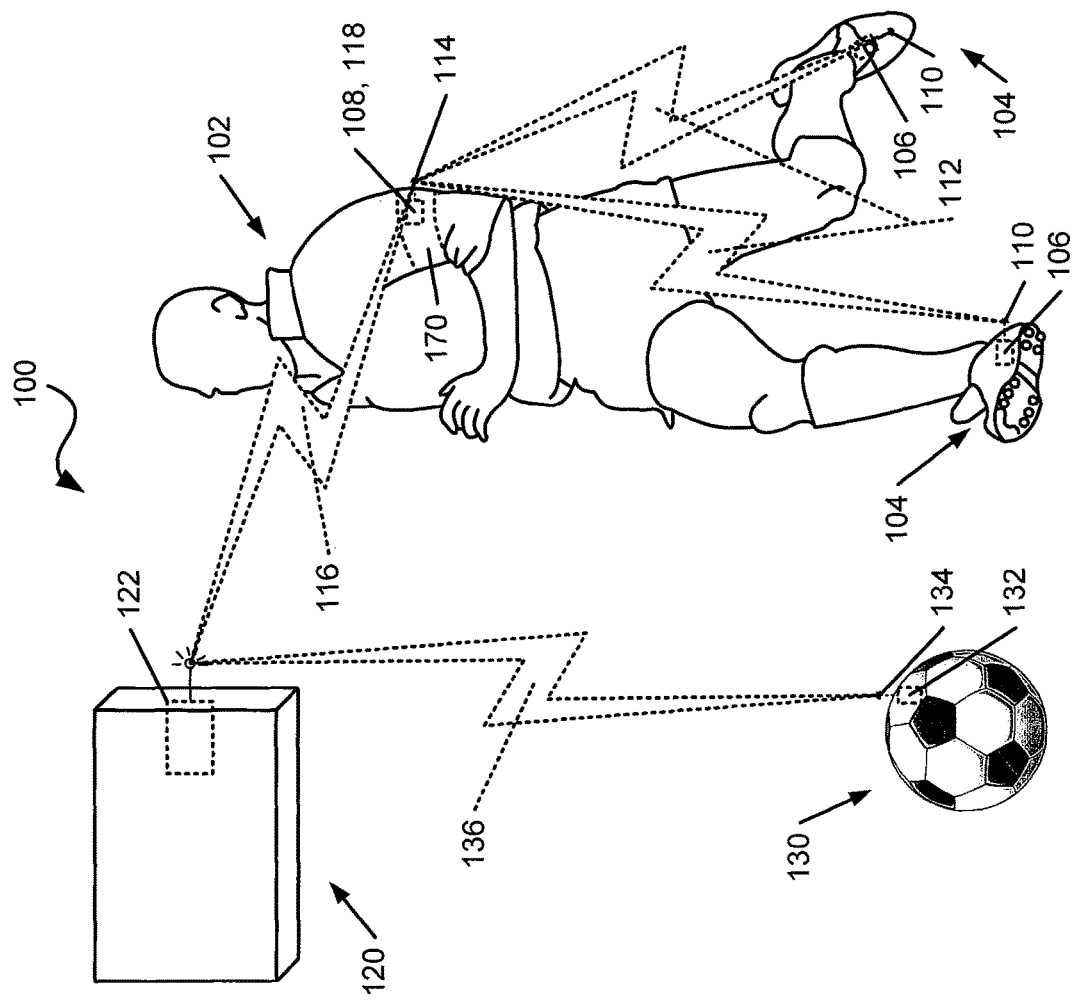
Figure 2C:
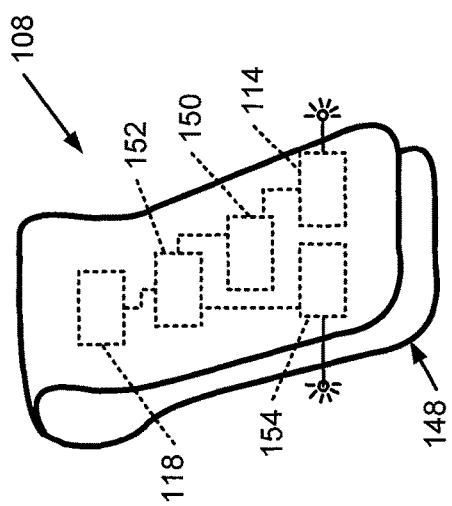

FIG. 2C schematically illustrates an example on-body receiver 108 that may be included in systems and methods in accordance with at least some examples of this invention. The receiver 108 of this example includes the data input device 114 that receives data transmissions from the shoes 104 or other remotely located sensors (e.g., sensors 106, 106*b*, 132, etc.). This remotely generated data may be stored in a memory device 150, further processed by a processor system 152, and/or immediately transferred to output system 154 (e.g., for transmission to another remote system, such as system 120). As mentioned above, receiver 108 further may include one or more of its own sensors 118, such as an accelerometer, a ball proximity detector, or other desired sensor element.

FIG. 2C illustrates the receiver 108 having a separate input device 114 and an output device 154. This is not a requirement. If desired, input may be received in and output may be transmitted from the receiver 108 using the same system (e.g., an input/output system, such as a wireless transceiver). When present as a separate system, the output device 154 may take on any desired form, such as a wireless transmitter (using any desired wireless transmission technology or protocol), a computer connection port (such as a USB port or other computer connection port), or the like.

Figure 2D:
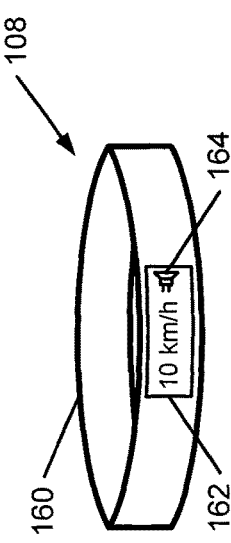

On-body receiver 108 may take on a variety of different forms without departing from this invention. For example, FIG. 2C illustrates the receiver 108 in the form of a clip 148 that may be attached, for example, to the waist band of the athlete's shorts (e.g., as shown in FIG. 1). The receiver 108 also may be in the form of a wrist band, such as a watch or other wrist borne data receiving device 160, like that shown in FIG. 2D. Optionally, if desired, the receiver 108 may include an output device that provides feedback to the athlete 102 in real time, as the athletic performance is taking place (such as a display monitor 162 for alphanumeric, video, or textual output; audio output (such as speaker 164, headphone, ear bud, etc.); etc.), as shown in FIG. 2D. As another option, the output device 154 may provide output to a device for providing real time feedback to the athlete 102 (such as a display, a speaker, an earphone, etc.).

FIG. 2E shows an overall system similar to that of FIG. 1, except in FIG. 2E the receiver 108 is formed as part of an armband 170, which may be worn inside the athlete's shirt or outside the shirt. Other arrangements and mountings for sensors, such as sensors 106, 106b, and/or 118, and/or receiver 108 (if present or necessary) are possible without departing from this invention. For example, one or more of the sensor(s) or receiver may be integrated into the clothing of the wearer, such as formed in or housed within a pocket provided in the waistband of the shorts or elastic of the jersey, as part of a belt structure, etc. As additional examples, a player's shin guard may include a sensor and/or a receiver device (e.g., for sensing the same type of data as sensed by the shoe borne sensor(s), such as step count, pedometer type speed and distance information, accelerometer data, ball contact data, ball proximity data, kick force, etc.). As another example, the receiver 108 or sensor(s) 118 could be included as part of a neckband, headband, or other apparel. Preferably, any body mounted sensors and/or receivers will be lightweight, durable, and positioned so as to have little or no impact on the player's performance or play and so as to have little or no possibility of injuring the player or others.

Figure 3:
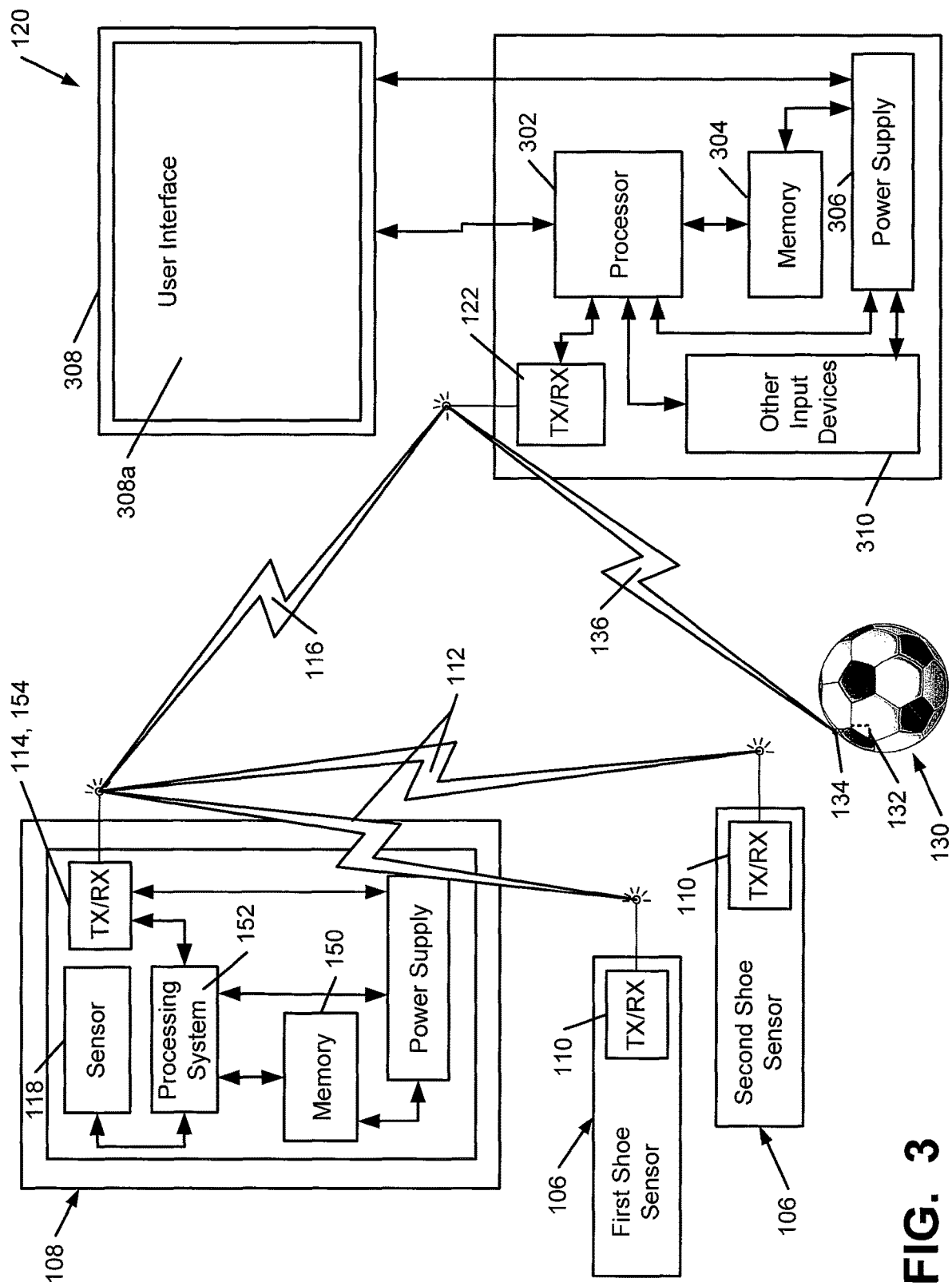
FIG. 3 illustrates a schematic view with a more detailed depiction of certain components of FIG. 1.

FIG. 3 illustrates additional features that may be included in systems and methods in accordance with at least some examples of this invention. In addition to the two foot mounted sensors 106 and the body mounted sensor 118 and receiver 108, FIG. 3 illustrates additional details of an example remote system 120 that may receive data transmitted from the receiver 108 and/or the ball 130 (e.g., via connections 116 and 136, respectively). In addition to transmitting data from the sensors 106, 118, and/or 132, transmission connections 116, 136, and/or 112 also may be used to transmit data from the remote system 120 to the receiver 108, ball 130, and/or shoes 104, respectively (e.g., to vary or control aspects of the sensors or other electronics provided in the receiver 108, ball 130, and/or shoes 104).

The remote device 120 may be, for example, portable audio and/or video players, cellular telephones, personal digital assistants, pagers, beepers, palm top computers, laptop computers, desktop computers, servers, or any type of computer controlled device, optionally a computer controlled device that generates or displays a human perceptible output and/or interface. The example remote device 120 shown in FIG. 3 includes a processor system 302 (which may include one or more processors or microprocessors), a memory 304, a power supply 306, an output device 308, other user input devices 310, and data transmission/reception system 122 (e.g., a wireless transceiver). The transmission/reception system 122 is configured for communication with the receiver 108, ball 130, and/or shoe sensors 106 via transmission/reception systems 114, 134, and/or 110 through any type of known electronic communication, including contacted and contactless communication methods, such as RFID, Bluetooth, infrared transmission, cellular transmissions, etc. The output device 308 may constitute any desired type of output device that includes a human perceptible interface and/or that generates output, such as portable audio and/or video players, cellular telephones, personal digital assistants, pagers, beepers, palm top computers, laptop computers, desktop computers, buzzers, vibrators, and the like.

In this illustrated example, the output device 308 includes a user interface 308a that may be in the form of a graphical user interface, such as an interface illustrating an internet website page or similar graphical depiction of data or information.

Figure 4:
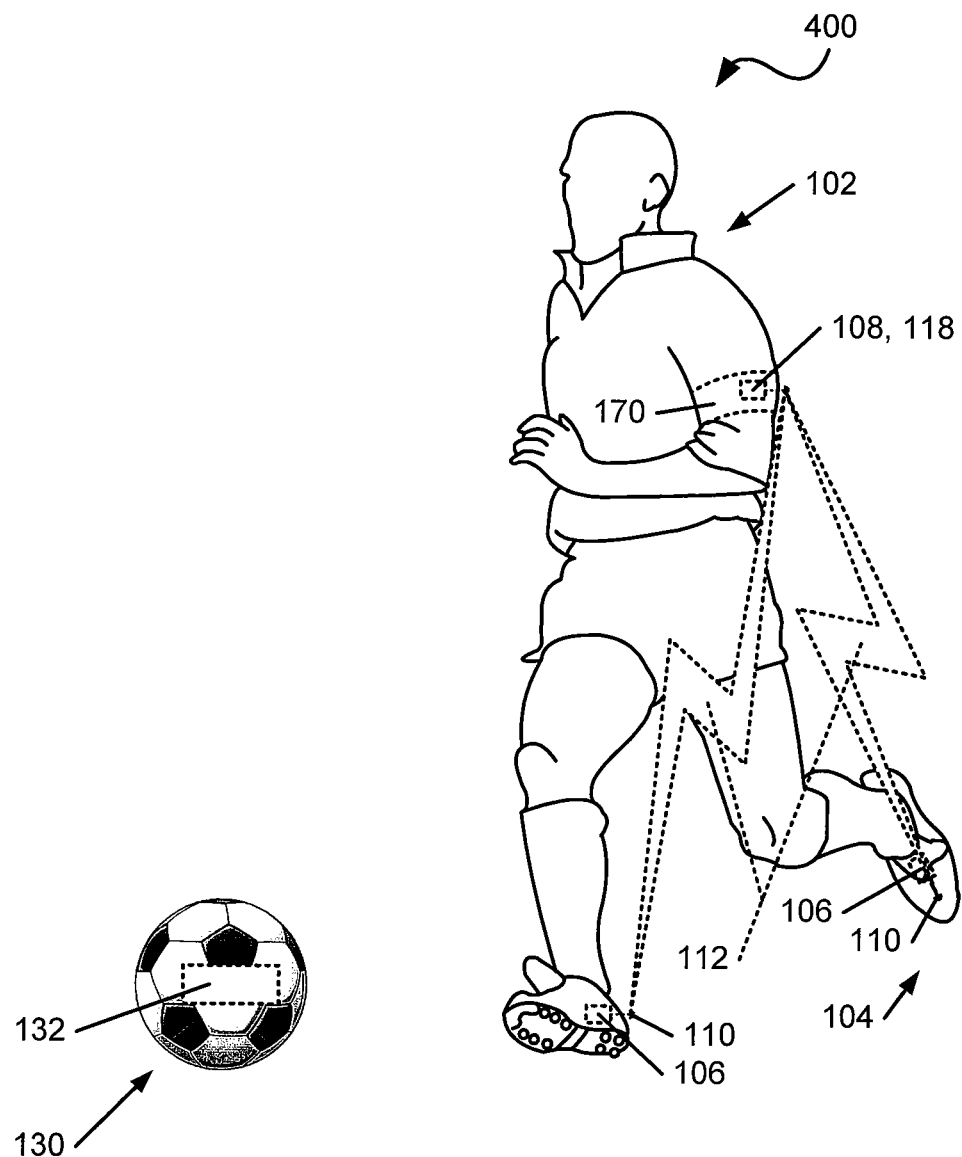
FIGS. 4 and 5 illustrate features of an alternative example athletic performance monitoring system in accordance with this invention.
Figure 5:
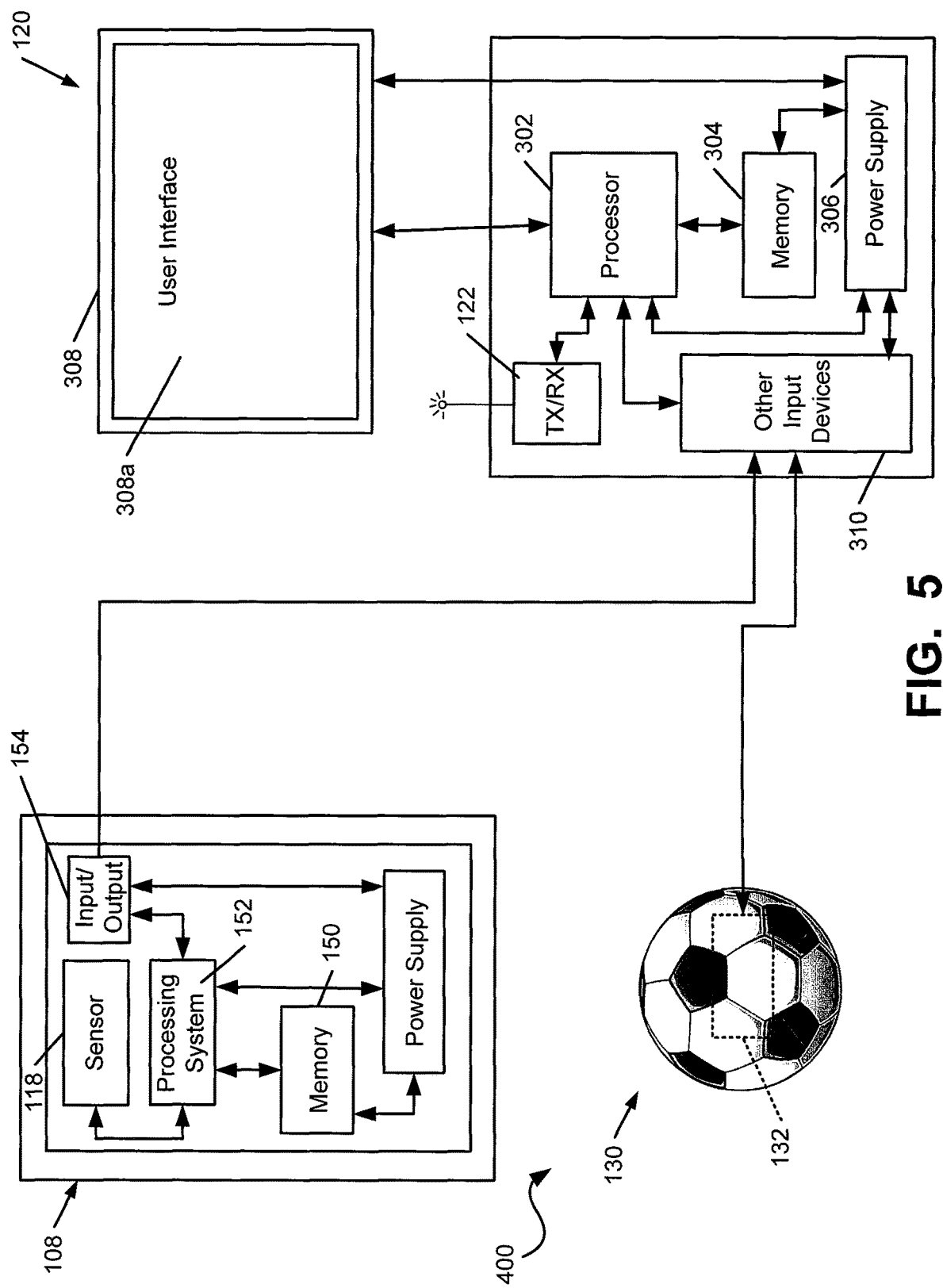

The systems illustrated in FIGS. 1 through 3 are potentially active, real-time transmitting systems that provide data to the remote system 120 as the athletic activity is taking place. This is not a requirement. For example, the system 400 of FIGS. 4 and 5 is much more passive than the systems of FIGS. 1 through 3. As far as the hardware systems, the system of FIG. 4 is similar to those of FIGS. 1 through 3 except that transmission systems 114 and 134 are removed, and receiver 108 and ball 130 function more like data loggers. More specifically, receiver 108 and ball 130 store data from sensors 106, 118, and/or 132 while the athletic activity takes place and save it for later transmission to a remote system 120, e.g., for post activity analysis, review, etc. If desired, even the data transmissions 112 from the shoes 104 to the receiver 108 may be omitted, and the shoe based data could be stored locally with the shoe sensors 106 for later download.

Optionally, if desired, the receiver 108 may include some sort of display (e.g., like that shown in FIG. 2D) or other output device to provide the athlete with some real-time performance feed back while the athletic performance is taking place (e.g., current speed, current distance traveled, minutes played, time in possession, on-ball speed, off-ball speed, a "pick up your pace" indication or other motivation or rewards, etc.).

After play is completed, the receiver 108 and the ball 130 (or an electronic component removed therefrom including their data log) may be plugged into a remote system 120, like those described above. See FIG. 5. Any type of connection system may be used without departing from this invention, including a wireless connection, a hardwired connection, connection via an input port (such as a USB port, or the like), etc. The remote system 120 may be located on the sidelines, in the locker room, in a player's home, or at any desired location, and it may be portable or non-portable.

Given the above example hardware descriptions, now additional details of example metrics that may be measured and the use of such hardware systems will be described in more detail.

B. Player Acceleration, Speed, and/or Movement Distance Sensing

Movement speed is one metric that is particularly important for gauging an athlete's performance. Systems and methods in accordance with at least some examples of this invention may measure the player's movement speed in various ways. For example, the sensor 106 in one or more of the athlete's shoes 104 may be adapted to measuring acceleration, speed, and/or distance information, e.g., in a manner akin to the way NIKE+ athletic performance monitoring systems and other pedometer based sensor systems monitor speed and distance information. For example, the sensor 106 may be an accelerometer, a pressure sensor (e.g., a piezoelectric sensor), or other force sensor that determines each time the player's foot hits the ground or other data associated with foot motion. By assuming that each foot contact constitutes a step, and by assuming each step covers a specific distance, the number of foot contacts may be correlated to an overall distance the athlete traveled. If desired, the distance for each step also may be adjusted based on various sensed factors, such as foot loft time between ground contacts, foot impact force, and the like, e.g., in manners that are known and used in the pedometer art. Also, by monitoring the time associated with the movements (e.g., by including a time stamp with each monitored foot contact, by tracking overall use time, etc.), the overall athlete's speed may be determined.

Pedometer based speed and distance measurement, however, may not always provide the desired degree of accuracy for use in many team oriented sports. For example, in soccer, football, basketball, rugby, and the like, athletes tend to move at widely varying speeds over the course of a game or practice session. They also tend to frequently jump vertically, dive, and otherwise leave their feet during play. Moreover, their feet are exposed to forces from sources other than contact with the ground, such as kicking the ball, kicking and hitting another object, etc. These additional features of many team sports may limit the accuracy of pedometer based speed and distance measuring systems.

Accordingly, systems and methods in accordance with at least some examples of this invention may include a body core mounted speed and/or distance measuring device. This may come, for example, in the form of an accelerometer mounted at the core of the athlete's body, such as in a waist band mounted accelerometer sensor (e.g., a two or three axis accelerator sensor 118, which may be included as part of receiver 108 to determine motion in two or three dimensions). Data generated by an accelerometer sensor 118 (i.e., the acceleration of the player at the location of mounting, such as the body's core or waist) may be integrated to provide the athlete's movement speed information, and it may be integrated again to provide the athlete's movement distance information. A body mounted sensor of this type may provide more accurate determination of the body's motion, e.g., when moving side to side, dancing around the ball, etc. Systems and methods for measuring acceleration and integrating the data obtained from an accelerometer are known.

Acceleration, speed, and/or distance determinations may provide useful data and information in several ways and for several performance metrics in systems and methods in accordance with this invention. For example, this data may be useful in determining the following metrics, which may be of interest to participants in team sports, such as soccer, basketball, American football, rugby, and the like: overall top acceleration, average acceleration, overall top running speed, average running speed, overall top running speed when in possession of the ball, average running speed when in possession of the ball, overall top running speed when not in possession of the ball, average running speed when not in possession of the ball, number of times speed exceeded a predetermined speed threshold (e.g., the number of times the athlete sprinted), overall distance traveled during the game, etc. This data can help the players (and/or their coaches) evaluate how hard the athlete is working, how much effort he or she is putting in to the game, how they are improving over time, the extent of recovery from injury, etc. This data also can be used to foster competition among individuals, such as team members, e.g., to provide motivation to work harder, improve, beat the other player's metrics, etc.

If desired, the body core based sensor (e.g., sensor 118 as part of receiver 108) may be the only sensor necessary for determining acceleration, speed, and/or movement distance determination. Therefore, if desired, the foot based sensors 106 could be eliminated. Nonetheless, if desired, the foot based sensors 106 could be used to provide secondary data for speed and/or distance measurement, such as data to help confirm the body core based sensor data, data to adjust or correct the body core based sensor data, and/or data to be used when the body core based sensor data is unavailable or seemingly unreliable. Additionally or alternatively, if desired, the shoe based sensor(s) 106 could be used to help eliminate drift of the body mounted accelerometer (e.g., if the shoe based data indicates that the player is stationary, this information could be used to calibrate or re-zero (e.g., eliminate drift from) the two or three axis body based accelerometer). The relative difference in acceleration measurements between a body core based accelerometer and a foot based accelerometer also may be determined.

As another alternative, at least some systems and methods in accordance with this invention may include a means of detecting the player's orientation or "mode of moving" when moving. For example, if desired, an electronic compass or a rotational sensor may be incorporated into the system, e.g., to aid in detecting a player's direction of movement and/or to provide additional details regarding the characteristics of the player's mode of movement (e.g., running forward, running at a side step, running backward, etc.). An accelerometer also can provide useful information regarding the direction of movement, if the accelerometer has a predetermined orientation at the start (e.g., with one axis of a two or three axis accelerometer facing the forward direction of motion). A determination of the amount of time or distance that a player runs forward, sideways, or backward could be a useful metric for measuring performance, at least in some sports. Also, if desired, different pedometer based speed and distance determination algorithms may be used, depending on the player's mode of movement (forward, backward, sideways, etc.), which may enable a more accurate determination of the player's overall movement speed or movement distance. More specifically, one algorithm may be appropriate for determining speed or distance (e.g., based on foot loft time, etc.) when a player is running forward, but a different algorithm may be better when running sideways, and even a different algorithm may be better when running backward.

In one more specific example of systems and measurements in accordance with this invention, one footpod (e.g., element 106, optionally one in each shoe 104) measures speed and distance of each step, e.g., utilizing a 3-axis accelerometer, and the collected data may be stored on the footpod 106 during a match or training session. A separate controller or a mobile phone (or other suitable device) may be used to communicate with the footpod 106, e.g., for the purpose of ascertaining footpod status, for starting/pausing/stopping recording of a session, and for initiating an upload of data (e.g., to computer system 120). In systems where a separate controller is used for these purposes, the user would need to connect the controller to his/her computer to upload their data, e.g., to a website service. In the case of a mobile phone (or other similar device) functioning as the controller, the phone could temporarily store the data and/or send the data directly to a web server wirelessly. Variations in these potential systems also are possible without departing from this invention.

Notably, for purely determining an athlete's acceleration, speed, or movement distance, no sensors, electronics, or other special features are needed in the ball. Therefore, if desired, a conventional ball could be used in such situations. In other situations and/or for measuring certain metrics, which will be described in more detail below, it may be advantageous to provide sensors, electronics, and/or other specialized structures in the ball.

C. Player Ball "Possession" and "Proximity" to the Ball Detection

Another useful piece of information for many types of team sports relates to a player's ball possession time. This may be measured, for example, by detecting an athlete's contact with the ball (e.g., by a hand, foot, or other body part), an athlete's close proximity to the ball, or in other manners. Determination of ball possession or proximity to the ball also can be an important part of other interesting or desired metrics, such as possession time, overall top running speed when in possession of the ball, average running speed when in possession of the ball, overall top running speed when not in possession of the ball, average running speed when not in possession of the ball, number of times near the ball, number of ball contacts or "touches," kick force, etc. This data can help the players (and/or their coaches) evaluate how hard the athlete is working, how much effort he or she is putting in to the game, which players are the most effective with the ball, which players work hardest to stay near the ball, the strongest defenders, the ball "hogs," etc. This data also can be used to foster competition among individuals, e.g., to provide motivation to work harder, improve, beat the other player's metrics, etc.

In some team sports where the ball is held throughout at least most of its possession, ball possession for an individual player can be relatively easy to determine, e.g., by determining which player is contacting the ball and/or by determining how long the player held the ball. One example is American football or rugby. Similarly, in lacrosse, the ball tends to rest in the head of the player's stick throughout the majority of the player's possession time. For such sports, appropriate sensors in the ball and/or on the player and/or on their equipment can relatively easily determine who has possession and the length of time of that possession. As one more specific example, RFID receivers or readers in an athlete's clothing or equipment (such as gloves, a jersey, helmet, pads, stick, shoes, etc.) may be triggered by an RFID transmitter tag mounted in or on the ball, and electronics included with the athlete's clothing or equipment may log how long each individual possession lasts. By time stamping or otherwise providing time data associated with this possession data, the possession data could be correlated to acceleration, speed, and/or movement distance data (e.g., determined as described above), to allow systems and methods in accordance with this invention to determine more specialized metrics, such as overall top running speed when in possession of the ball, average running speed when in possession of the ball, overall top running speed when not in possession of the ball, average running speed when not in possession of the ball, etc. While other players also may come in contact with the ball during an individual play, this contact typically is relatively short term, and it typically is overlapped by and/or surrounded on each end by contact with the main player in possession. Therefore, the data can be easily analyzed to determine which contacts simply constituted a fleeting, non-possessory contact and which contacts actually demonstrated possession of the ball. Alternatively, if desired, multiple players could be considered to simultaneously have "possession" of the ball by systems and methods according to this invention (e.g., if "possession" is simply equated to any contact with the ball).

In other sports, however, continuous contact with the ball is not a feature of ball "possession." For example, in soccer and basketball, a player in "possession" "dribbles" the ball to move it up and down the field of play, resulting only in occasional contact with the ball. The ball is not typically held for long periods of time or carried for long distances in such sports. In hockey and field hockey, the ball (e.g., including a hockey puck) may repeatedly come into and out of contact with the player's stick while the player in possession of the ball moves down the field of play. Also, a player in "possession" of the ball may only make contact with the ball once, sometimes for only a very short time period (e.g., when a quick pass or shot is made). Moreover, in all of these sports (e.g., soccer, basketball, hockey, field hockey), players on the opposing teams may attempt to steal the ball or puck throughout a player's possession. Such features of play make ball "possession" somewhat more difficult to determine using sensors.

Systems and methods in accordance with at least some examples of this invention may approximate a player's ball "possession" using various features of proximity of the player to the ball. While the description below primarily focuses on possession determination in the context of soccer, those skilled in the art, given the benefit of this disclosure, would be capable of extending features of this description for use in other sports, such as basketball, hockey, field hockey, American football, rugby, lacrosse, and the like.

Figure 6:
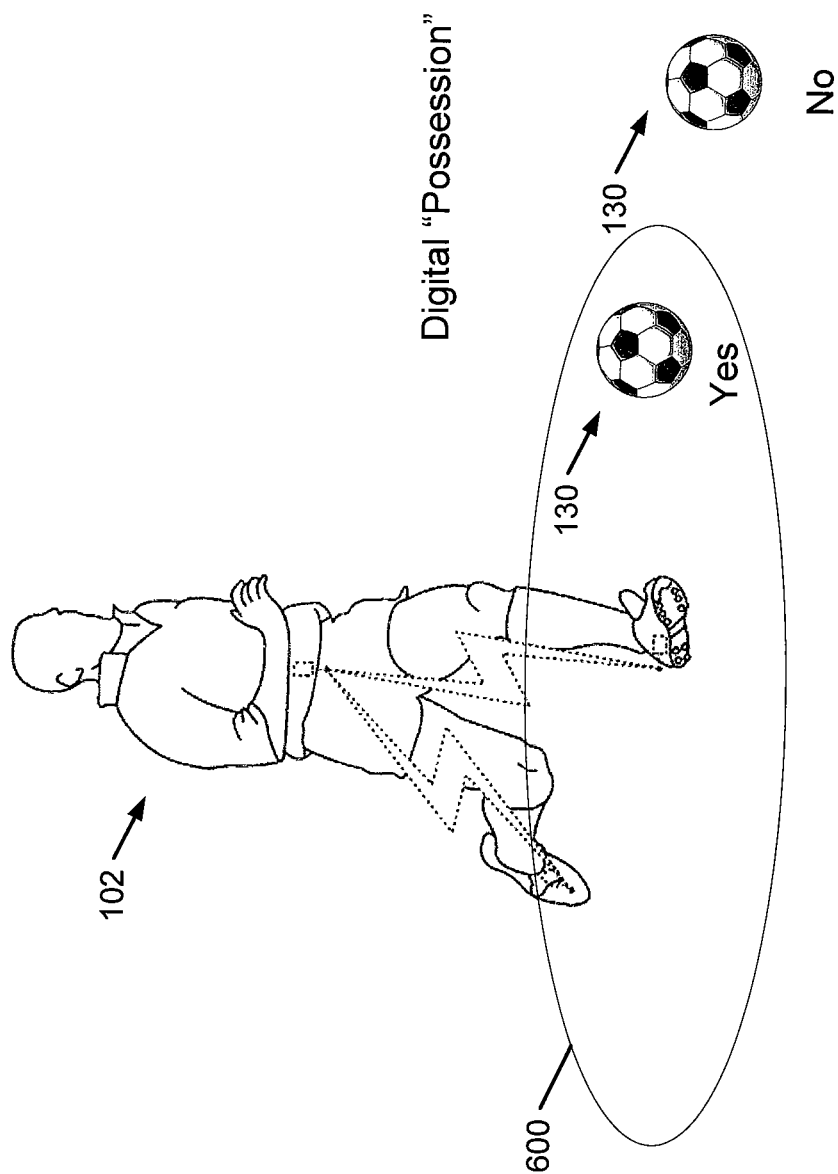
FIGS. 6 and 7 illustrate various potential features useful in determining ball "possession" or ball "proximity" in accordance with at least some examples of this invention.

Determination of "possession" may include various features. For example, systems and methods in accordance with at least some examples of this invention may determine that "possession" exists whenever a player contacts or comes within a certain threshold distance from the ball (e.g., within one meter). As illustrated in FIG. 6, such systems may be thought of as "digital" possession determining systems, where a player either has possession or does not have possession. More specifically, when the ball 130 is within a one meter distance of the player 102 (inside ring 600), the player 102 may be considered as having "possession." When the ball 130 is more than a one meter distance from the player 102 (outside ring 600), the player 102 may be considered as not having "possession." In such systems and methods, multiple players may be considered as having "possession" at a single time (when each player is within close proximity to the ball). When multiple players from different teams are located in proximity to the ball, this also may be considered "contested time," as is described in more detail below.

Optionally, if desired, a positive determination of "possession" may require at least one contact with the ball (and optionally, the "possession" determination may start at that contact). As another option, systems and methods according to the invention may track both "possession" (e.g., requiring at least some contact and/or continuing contact with the ball) and "proximity" (e.g., when there has not been contact but the player is close to the ball or when a different player has made an intervening ball contact but the first player remains close to the ball, etc.). If desired, a new "possession" determination may be made each time a different player contacts the ball (although the previous player in contact may remain close to the ball and his or her "proximity time" may continue to accumulate). As noted above, "proximity" may be simply equated to "possession" in some systems and methods according to this invention.

Figure 7:
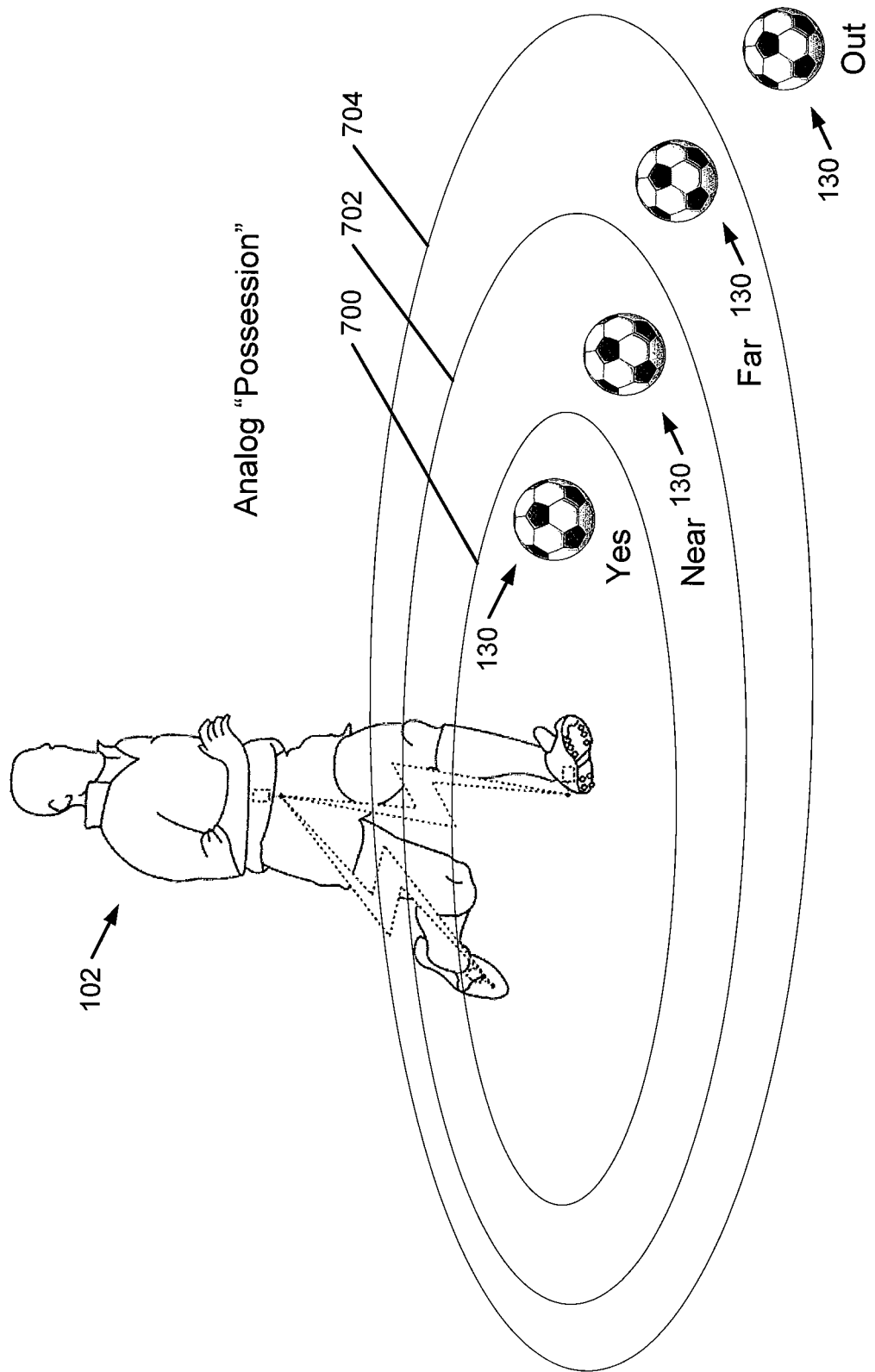

"Possession" also may be considered as more of an "analog" parameter. For example, systems and methods may be produced to provide a more detailed determination of the proximity of a player to the ball. For example, as shown in FIG. 7, determination of the player's distance from the ball may be more closely determined, to better enable a determination of "possession." For example, when the player 102 is very close to the ball 130 (e.g., within inner ring 700), that player may be considered in "possession" of the ball 130 (if desired, multiple players may have "possession" at one time). When the player 102 is relatively close to the ball 130 (e.g., within ring 702 but outside ring 700), the player 102 also may be considered to be in possession of the ball, optionally, if other parameters are met (such as if the player 102 was the last person to touch the ball 130 or the player 102 is the closest player to the ball 130, and there has been no intervening ball contact by another player, etc.). When the player 102 is somewhat close to the ball 130 (e.g., within ring 704 and outside ring 702), the player 102 also may be considered to be in possession of the ball 130, optionally, if other (optionally, more stringent) parameters are met (such as if the player 102 was the last person to touch the ball 130, the player 102 is the closest player to the ball 130, and there has been no intervening ball contact by another player, etc.). Any desired possession parameters may be developed without departing from this invention. When the player is too far away from the ball 130 (e.g., outside ring 704), systems and methods according to at least some examples of the invention may determine that the player 102 does not possess the ball 130. Optionally, systems and methods according to at least some examples of this invention may determine that a player remains in "possession" of the ball until a new player contact with the ball is ascertained, irrespective of the previous player's location with respect to the ball.

1. RFID Technology

One potential way of determining ball possession or proximity is through the use of RFID (radio frequency identification) technology. RFID systems use coupled energy to transmit a small amount of data between an interrogator (also known as a "reader") and a remote, inexpensive tag. The tag can be stationary or in motion with respect to the reader. Such RFID systems can be categorized according to two main criteria, namely: the means of powering the tag (e.g., passive, semi-passive, or active) and the energy coupling mechanism (e.g., inductive or radiative).

Figure 8A:
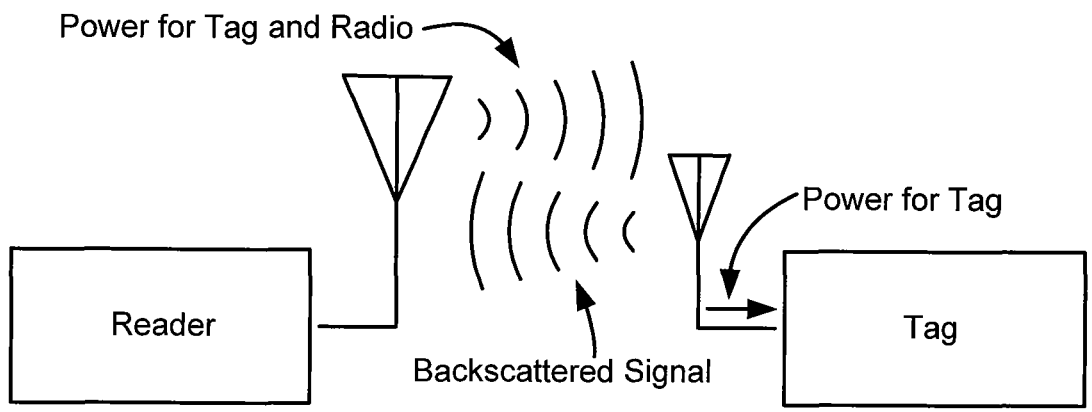
FIGS. 8A through 8C illustrate variations in radio frequency identification ("RFID") systems that may be used for "proximity" or "possession" determinations in athletic performance monitoring systems and methods in accordance with this invention.
Figure 8B:
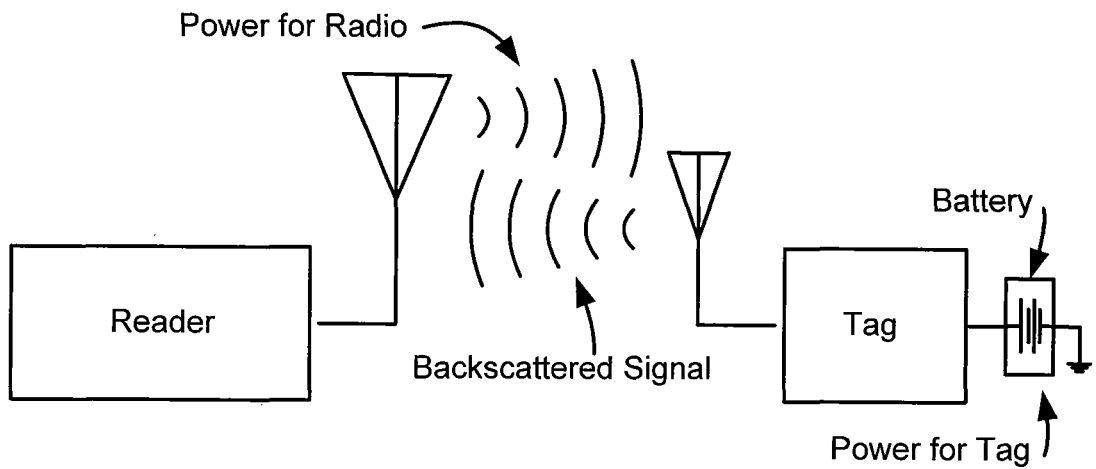
Figure 8C:
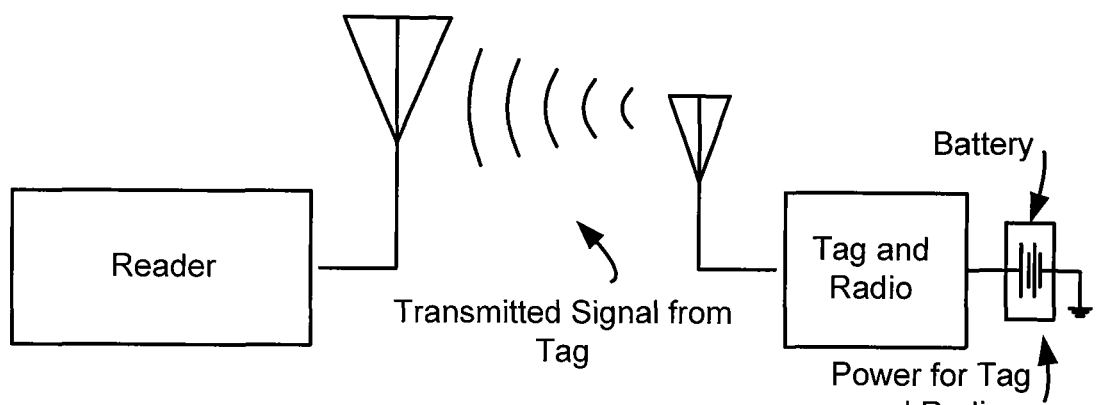

FIGS. 8A through 8C schematically illustrate various RFID technologies. In the "passive" RFID system illustrated in FIG. 8A, power for both the tag and the return radio signal (i.e., the "backscattered signal" in FIG. 8A) generated by the tag are provided by energy recovered from the reader signal. Such a completely "passive" system may be advantageous in the environment of this invention because it could eliminate the need for a power source (e.g., a battery) on the ball. In "semi-passive" RFID systems, as illustrated in FIG. 8B, power for the return radio signal is provided from recovered reader energy signal, but the tag electronics are powered by a small battery included with the tag. The "active" RFID system illustrated in FIG. 8C is really akin to a traditional radio system. The tag radio signal and the electronics are both powered by a local battery provided with the tag (and the reader's electronics are powered by its own separate power source).

Radio tag frequencies range from a few hundred MHz to several GHz. In this spectrum, wavelengths become comparable to the mechanical scale of personal electronics and more specifically, full wavelength antenna sizes. Such features allow far-field operations where power varies inversely with the square of the distance from the source.

Figure 9:
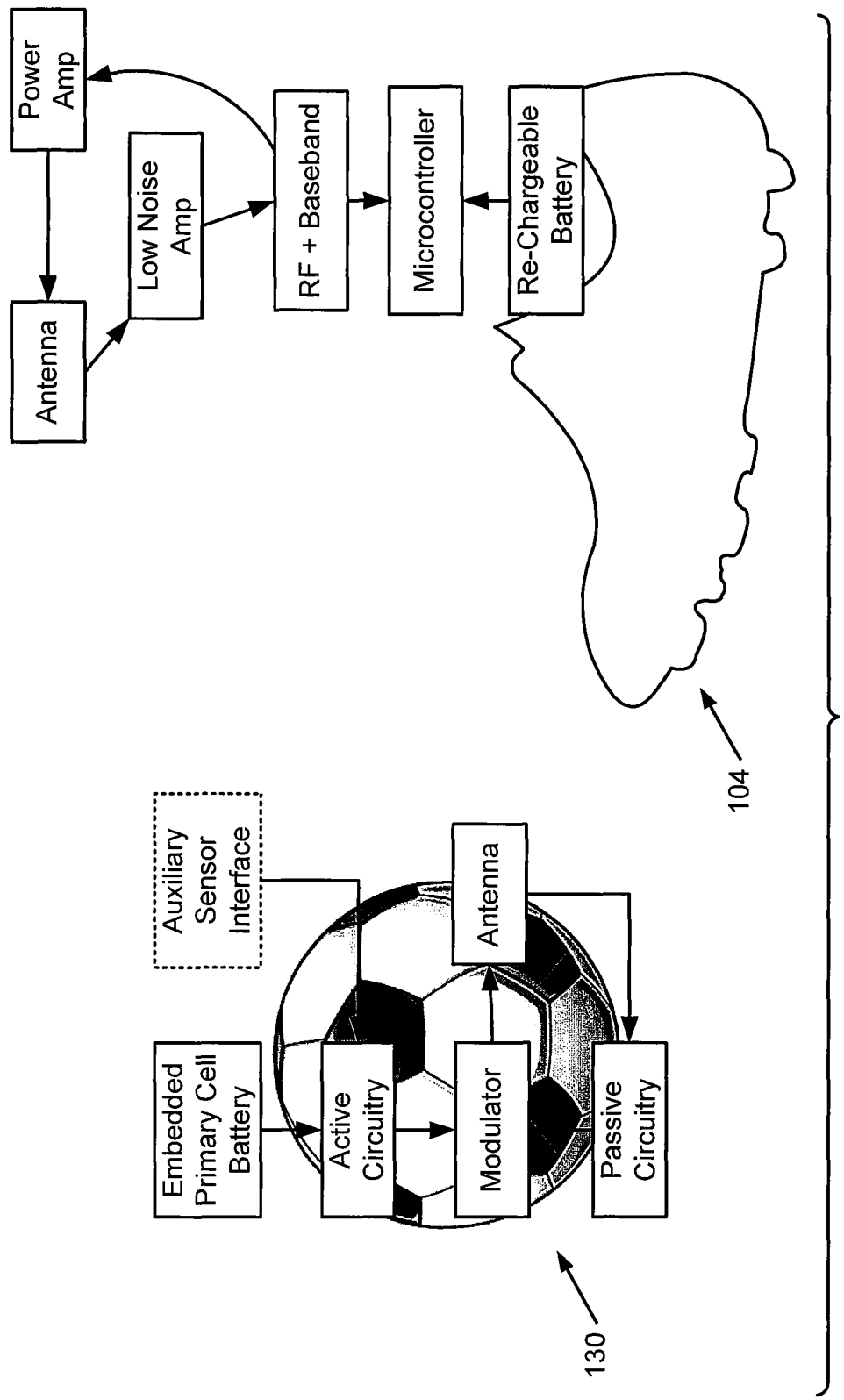
FIG. 9 illustrates example features and components of a semi-passive RFID based "proximity" or "possession" determination system that may be used in systems and methods in accordance with this invention.

FIG. 9 illustrates one example of the hardware and equipment that may be used in a semi-passive RFID system to detect player proximity for soccer or other sports. Notably, in the system illustrated in FIG. 9, the ball 130 includes the RFID tag and its associated antenna and other electronics, and the shoe 104 (or other article of the player's equipment, such as a shin guard, sock, receiver 108, etc.) includes the RFID reader and its associated antenna and other electronics. More specifically, the ball 130 of this example carries an embedded primary cell battery, an auxiliary sensor interface, active circuitry, a modulator, passive circuitry, and an antenna. The player (e.g., the shoe 104) in this example system carries a re-chargeable battery, a microcontroller, an RF+baseband component, a low noise amp, a power amp, and an antenna. The battery assist on the ball mounted tag permits a relatively low-received power density, which effectively lowers the transmission power required on the player (and lowers the mass of the necessary battery and other electronic equipment to be carried by the player). A single ball 130 may include multiple tags on the ball (e.g., to assure that a tag antenna is always facing the player's reader, to enable more sensitive distance measurement, such as for analog possession determinations, etc.). RFID tag and reader equipment of this type is conventionally known and commercially available.

Proximity detection of this type may be combined with data relating to foot contact with the ball, if desired, to distinguish between ball possession and ball proximity. Alternatively, as noted above, possession may simply be equated with proximity, if desired.

2. DPR Technology

Digital packet radio ("DPR") also may be useful in determining ball proximity and/or "possession" (optionally, in conjunction with other data, such as foot and/or ball contact data) in systems and methods according to at least some examples of this invention. Many NIKE+ athletic performance monitoring products (available from NIKE, Inc. of Beaverton, Oreg.) use DPR for wireless data communications (e.g., in the 2.4 GHz band). DPR also is used in many commercially deployed networks, such as cellular networks, WiFi (802.11), ZigBee, and PCS. Two example chipsets that may be used for implementing DPR based proximity and/or possession determinations in systems and methods according to this invention include chipsets available from Nordic Semiconductor Inc. of Sunnyvale, Calif. and ANT Wireless of Cochrane, Alberta, Canada. Both companies make ultra low-power radio silicon chipsets that can be used in a variety of applications. The radio chipsets can be powered by a standard coin cell type battery with excellent device lifetimes.

Figure 10:
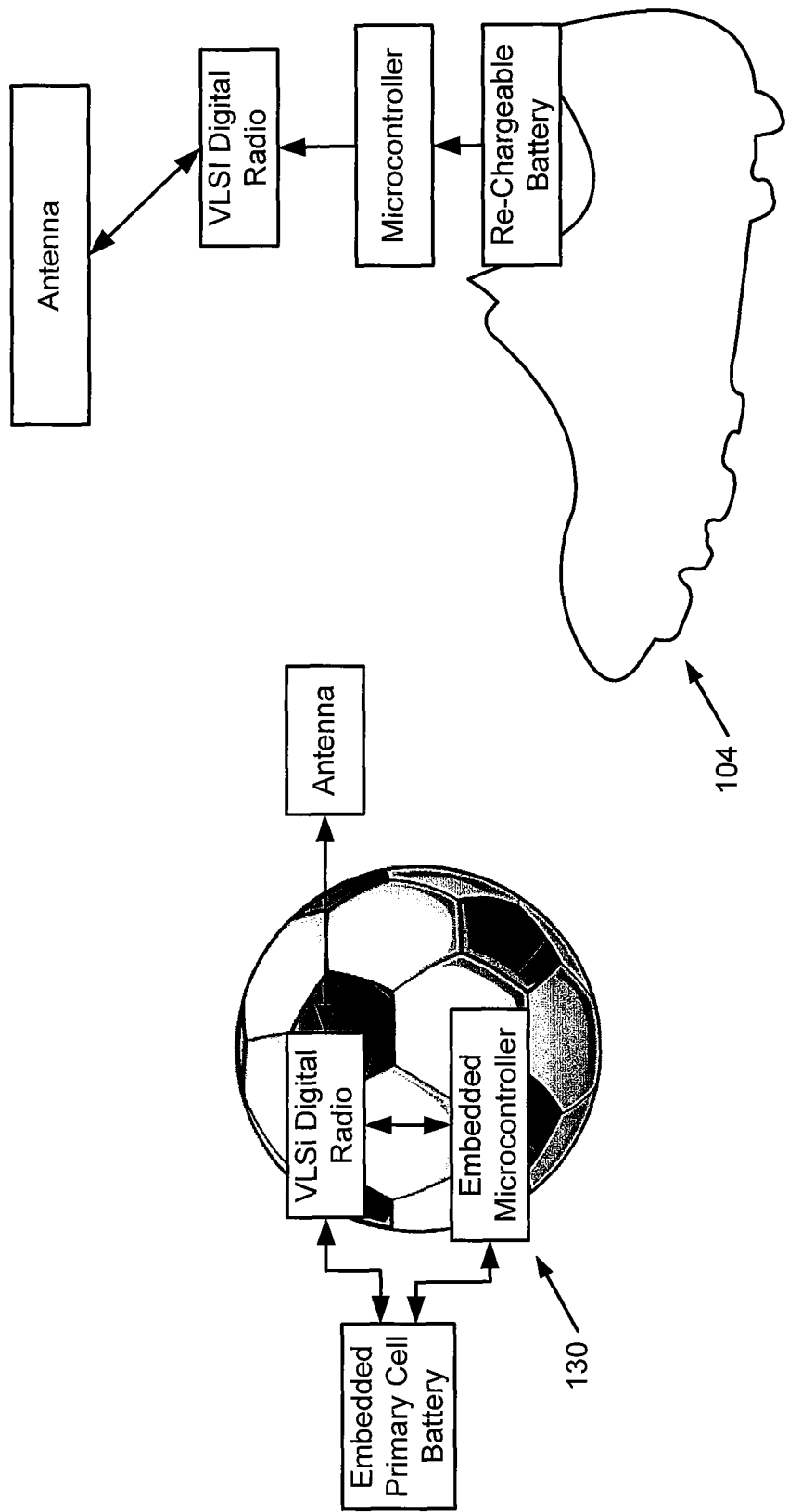
FIG. 10 illustrates example features and components of a digital radio packet based "proximity" or "possession" determination system that may be used in systems and methods in accordance with this invention.

DPR implementations for proximity and ball possession determinations offer low-power, high range systems and methods. FIG. 10 illustrates one example system. Notably, while these systems and methods are low power and high range, they still require an active receiver end (i.e., some electronics and/or power on the ball 130), as shown in FIG. 10. In the DPR system of FIG. 10, the ball carries an embedded power source (e.g., primary cell battery), an embedded microcontroller, a very large scale integration ("VLSI") digital radio system (e.g., a chip), and an antenna. The athlete (e.g., as part of the shoe 104 or receiver) carries a re-chargeable battery, a microcontroller, a VLSI digital radio system (e.g., a chip), and an antenna. The DPR system may operate on any desired frequency, such as 915 MHz or 2.4 GHz. Such hardware systems are known and are commercially available, as noted above.

In the ball 130, the small radio and the microcontroller trigger radio bursts that send out unique identifying data packets. The trigger for each radio burst could be periodic (e.g., every 50 ms, every second, etc.). On the other hand, the trigger could be aperiodic, such as in response to an actual event trigger, like motion, contact, impact, etc. These packets allow a body-worn receiver on the player 102 (e.g., in boot 104, in a body core worn element, etc.) to log received data that directly correlates to how long the ball 130 spent within proximity to the receiver. This proximity may be correlated to ball possession (optionally, if another metric is logged, such as contact between the player's foot and the ball 130, as determined by a shoe based sensor 106*b*). This is a very "digital" possession type determination system. If desired, as noted above, possession may be equated to proximity.

DPR also may be used to provide more analog possession information. In such a system, the ball 130 may serve as the receiver, and the body worn device may provide the bulk of the transmissions. In such as system, the ball 130 would periodically listen for a radio packet broadcast from the body worn transmitter. The body worn-transmitter could send out bursts of packets at different set output powers. The ball 130 would only receive packets from the weakest transmitted signals when it is in close proximity to the player 102. The number of signals received by the ball 130 will decrease the further that the ball 130 is away from the player 102 sending the signals until it is receiving only the strongest signals or none at all. The ball 130 may respond to any received packets by transmitting back with a unique identifier derived from the packets it received (e.g., an identifier indicating the transmission power). This arrangement allows the body worn receiver to determine how far away the ball 130 is based on the weakest signal that is received at the ball 130 and for which a response was sent. Alternatively, if desired, the ball could send out the bursts of packets at different output powers and the body worn sensor could receive these packets and determine the relative distance between the ball and the body sensor based on the detected signals (and their corresponding power levels).

With DPR systems, because there is an active radio at each end, i.e., at the ball 130 and at the player 102, the transmission power can be quite low (and smaller than other technologies), but, as noted above, it does require some power source on the ball. DRP also provides the ability to dynamically vary output power, giving systems and methods in accordance with at least some examples of this invention the ability to estimate the range between the ball 130 and the player 102, and/or even the ability for the player's system to acquire the ball outside of some predetermined "possession" distance (e.g., one meter).

3. RADAR Technology

Ball possession and/or player proximity to the ball also may be detected in some example systems and methods according to this invention by RADAR technology ("RAdio Detection And Ranging"). RADAR systems use reflected radio "ping" energy to identify and locate target objects by analyzing their reflected "signature." RADAR systems do not require active transmission in two directions, which means that the ball need not include an active transmitter or a power source in at least some RADAR based proximity or possession determination systems and methods in accordance with this invention. If desired, however, RADAR based systems could rely on an active (power utilizing) systems as part of the ball to generate a radio "ping" for the mobile detector to recognize, or they may in some way (e.g., actively powered or passively unpowered) enhance or distinguishingly mark the reflected energy to ease the mobile transponder's job of identifying the ball from the clutter of background noise, other reflections, and/or miscellaneous distortions in the signal.

Passive RADAR systems, in which the ball does not include a power source, can rely on one or more other RADAR reflection techniques to increase the "visibility" of the reflected signal from the ball (e.g., by increasing its gain or coherence). One example of such a technique would be to provide a retroreflective device on the ball, such as a corner reflector. As one example, the corner retroreflective material could be provided within one or more seams of the ball, or optionally in an interior layer of the ball (if the impinging radiation is capable of penetrating the ball's exterior cover). Corner reflectors are known in the RADAR and other art, and these devices reflect radiation outward from the reflector in substantially the opposite direction from which it entered the reflector (i.e., directly back toward the radiation source and/or parallel to its incoming direction). Another example technique would be to provide "chaff" on or in the ball structure. "Chaff" constitutes specifically sized small pieces of RADAR reflective material organized in a unique pattern on the ball that is easily recognized by the RADAR detection system. Such reflectors and chaff are well known in the RADAR field, and are sized and shaped in suitable configurations so as to be capable of incorporation into the structure of a ball (such as a soccer ball, hockey puck, basketball, or the like). These features increase the RADAR reflection signature from a ball and make the ball better stand out among the other RADAR radiation reflected from other objects in the area (such as other players, other equipment on or near the field, goal posts, etc.).

Another technique for helping a passive (non-powered) ball's radiation reflection signature stand out among other objects involves the use of a passive frequency doubler structure on the ball. A passive frequency doubler works using a principle similar to "square law" detectors. Non-linear devices can generate frequency harmonics when stimulated with a signal. A diode, at small signal levels (e.g., equivalent to less than −20 dBm) has a VI relationship that is roughly $I=k*V^2$, where k is some constant. Such a device is capable of generating a frequency harmonic that is twice that of what is used to drive the diode, by the equation: $\cos(f_0)^2=\frac{1}{2}+\frac{1}{2}*\cos(2*f_0)$, where $f_0$ is the input frequency. This frequency harmonic can be radiated out of the same antenna that received the fundamental frequency.

By providing a passive frequency doubler structure on the ball in such a RADAR system, the reflected radiation detector or receiver only needs to listen for a signal at twice the carrier frequency that its associated transmitter radiated. This doubled frequency signal will be known to be unique to the object carrying the passive frequency doubler (i.e., the ball in this arrangement). In addition, the frequency doubler also generates a DC component, which may be used to power a small amount of electronics on the ball. These electronics could modulate the signal that the frequency doubler radiates, essentially giving the ball a unique ID. On the other hand, the signal that is radiated can be coded (with a barker code or a pseudorandom sequence), and then auto-correlated with the returned signal for an additional signal processing gain. Another simple method that may be used for processing gain would be frequency chirping.

Figure 11:
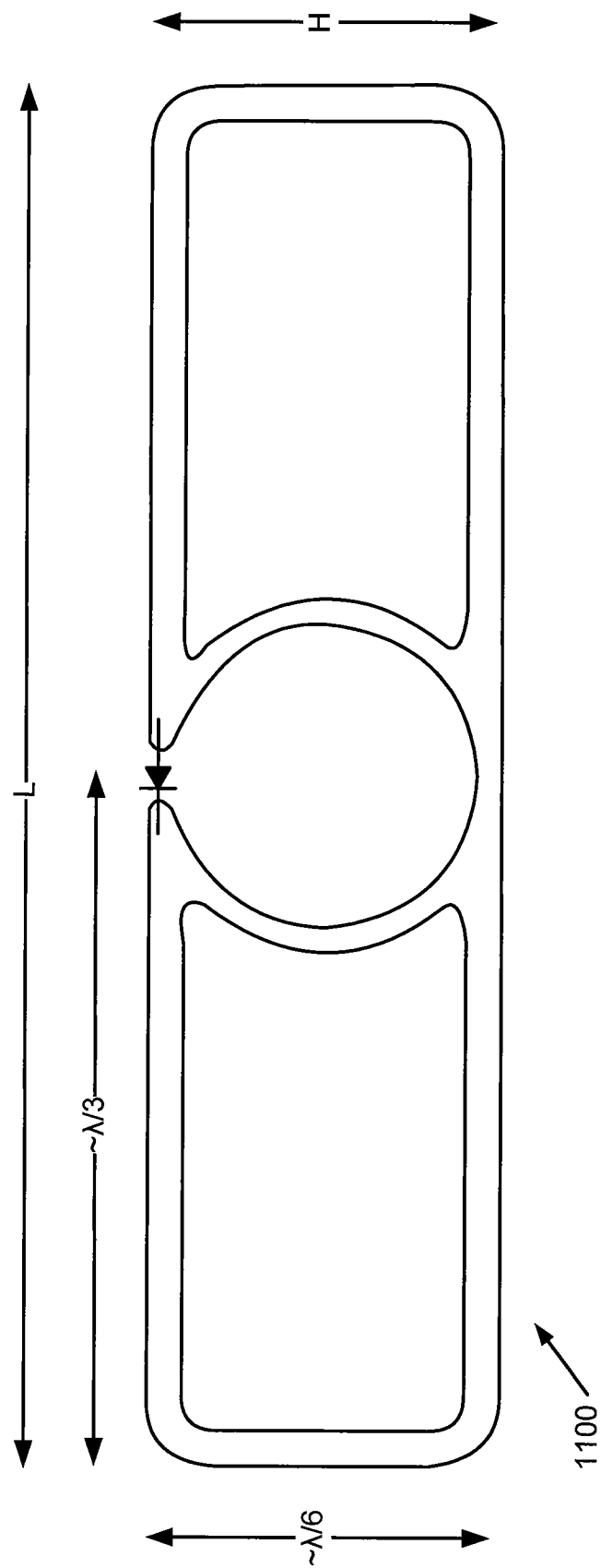
FIG. 11 illustrates an example passive frequency doubler system that may be used in "proximity" or "possession" determination systems and methods in accordance with this invention.

Frequency doubler antennae of the types described above are known, as described for example, in U.S. Pat. No. 4,890,111, which patent is entirely incorporated herein by reference. One example antenna 1100 as described in this patent is illustrated in FIG. 11. The dimensions of such an antenna may be about ⅔ of the wavelength λ of the transmitted and incident radiation frequency in the length dimension L and about ⅙ that wavelength λ in the height dimension H. With such an antenna incorporated in to the structure of a soccer ball (e.g., on its exterior surface, between layers of the ball, within the ball interior, etc.), the mobile receiver could be configured to "listen" for a specific carrier frequency (i.e., twice the transmitted frequency) to detect the presence of the ball, e.g., when enough energy is present in both the forward and return path from the player mounted radiation transmitter, to allow the radiation to reach the ball and bounce back to the player mounted radiation detector. As some more specific examples, the initially transmitted RADAR frequency may be 915 MHz, and the reflected frequency may be doubled to 1830 MHz. Another good candidate is 433 MHz (doubled to 866 MHz). The use of other frequencies also is possible without departing from this invention.

Figure 12:
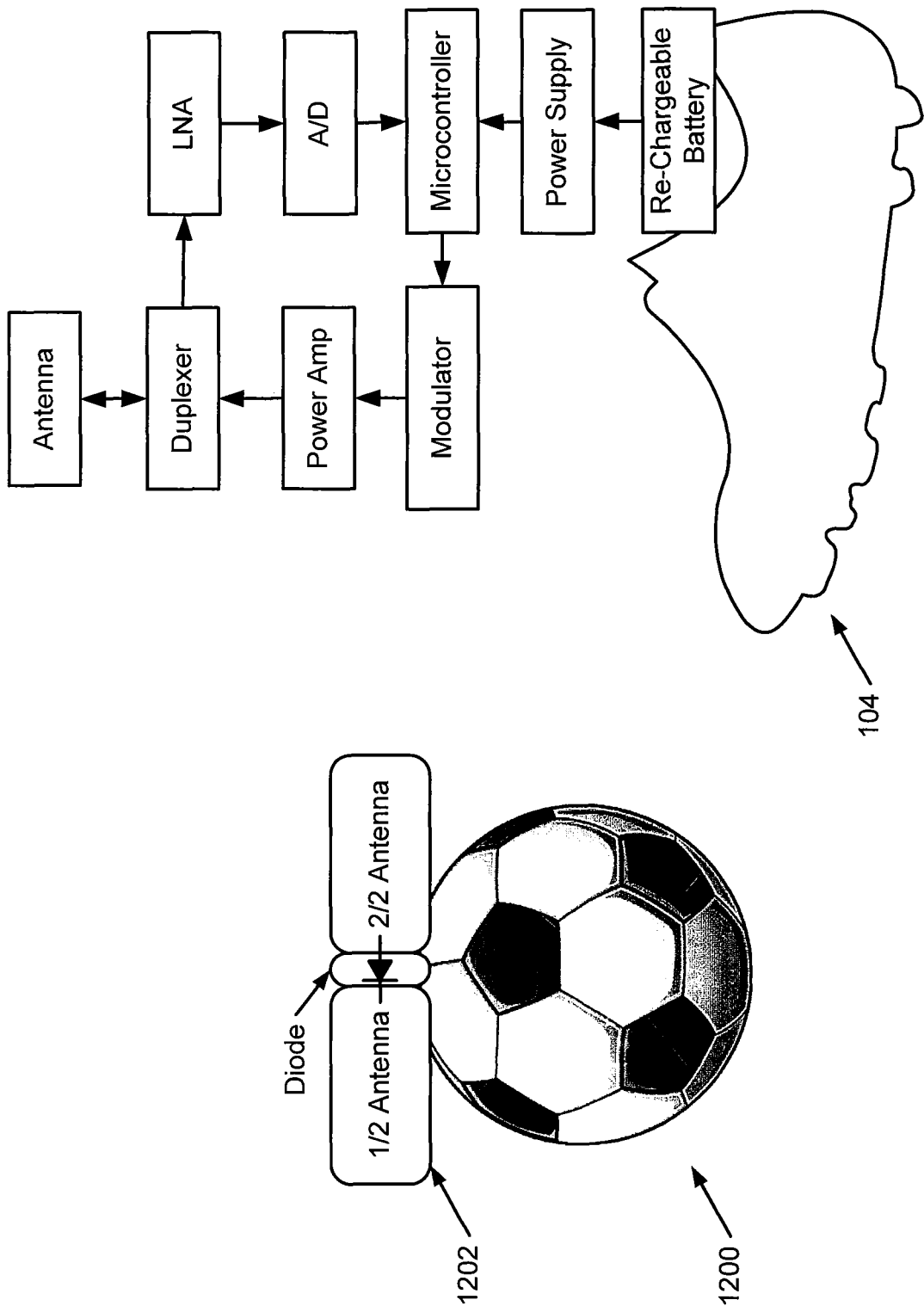
FIG. 12 illustrates example features and components of a RADAR based "proximity" or "possession" determination system that may be used in systems and methods in accordance with this invention.

FIG. 12 illustrates example structures that may be provided on both the ball 1200 and the player 102 (e.g., as part of the player's shoe 104, as part of receiver 108, etc.) in accordance with at least some RADAR based proximity detection systems in accordance with this invention. As shown in FIG. 12, the ball 1200 includes an antenna structure 1202 like that described above in conjunction with FIG. 11. The shoe 104 (or other player borne component) includes a rechargeable battery and/or other power supply, a microcontroller, a modulator, a power amp, a duplexer, an antenna, a low noise amplifier (LNA), and an analog to digital converter (A/D). The shoe 104 transmits radiation toward the ball 1200 at a first frequency (e.g., 915 MHz), and the ball 1200 doubles the frequency through antenna 1202 and reflects the radiation back toward the shoe 104, where it can be detected. The ball 1200 may include plural antennae all around the ball structure to assure that at least one antenna faces the receiver on the player.

As an alternative, if desired, one or more RADAR radiation sources may be independent of the player (e.g., located on the sidelines or at other locations, to cover the entire field, etc.). In such a system, the player 102 need only carry the reflected radiation detector (and its associated power source and electronics), and not the radiation transmission source. The ball electronics may be configured to send out radiation only at a desired power level so that a player mounted detector would only detect the reflected radiation from the ball when in relatively close proximity to the ball (e.g., within 1 meter, etc.).

Figure 13:
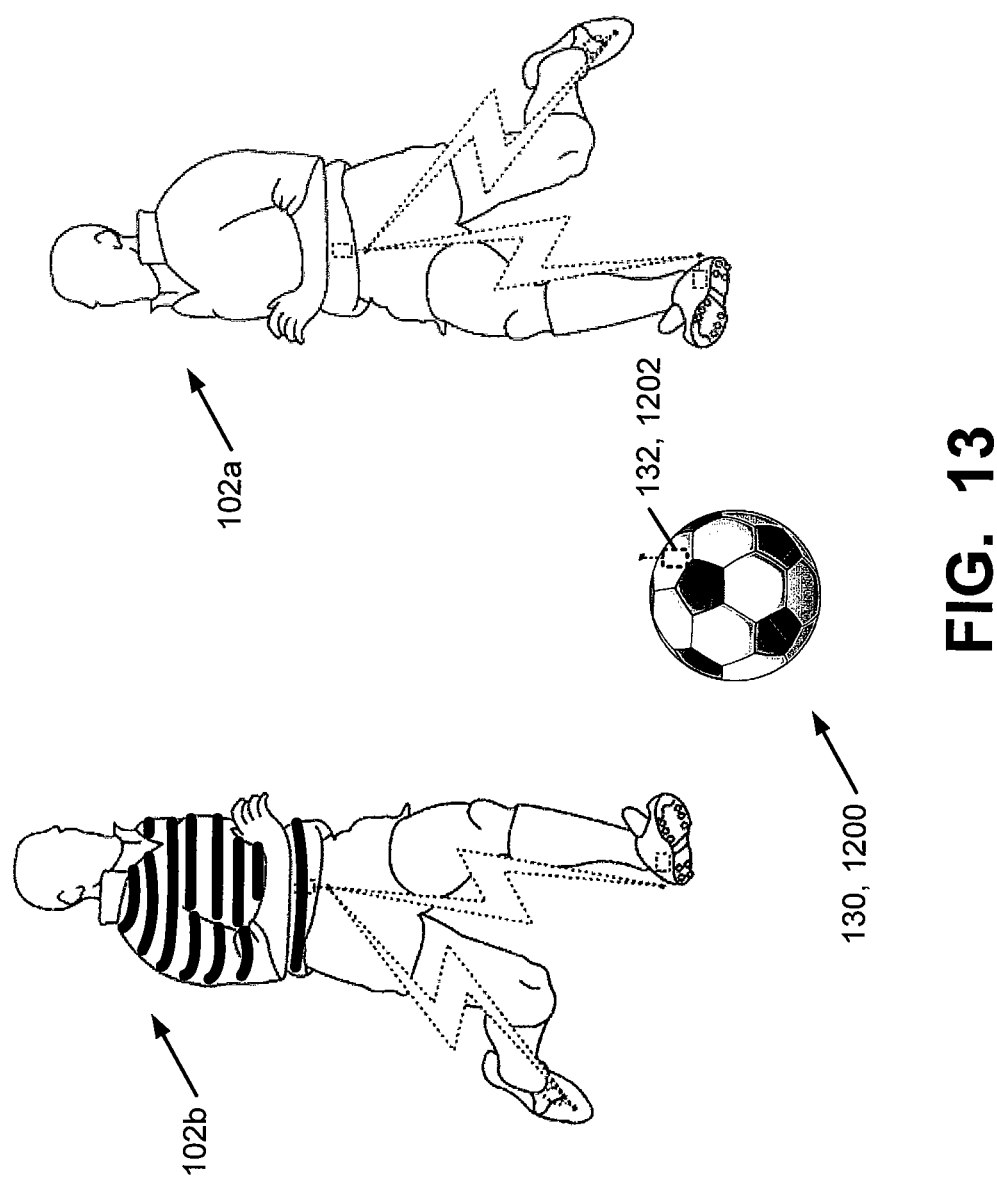
FIG. 13 is a diagram that aids in the discussion of multi-player concurrent usage of systems and methods of the invention and "data collisions;"

Various features may be provided to help prevent "packet collisions" when multiple players are using systems and methods in accordance with this invention, e.g., to help prevent one player from detecting radiation reflected from the ball transmitted by a different player. For example, as shown in FIG. 13, two players, one player 102a from one team and one player 102b from the other team (or even more players), may approach the ball 1200 simultaneously. If each player is equipped with actively transmitting RADAR or other data transmitting systems and methods according to the invention, the various detectors or sensors could easily read the wrong data and incorrectly determine position or proximity data. Such data "packet collisions" should be avoided to provide more reliable and usable data for systems and methods according to this invention.

One way of limiting or eliminating "packet collisions" constitutes a timing plan where each player's device transmits at a random interval, with a standard mean interval in place. This would make it unlikely that any two or more players would be transmitting at a given time in proximity to the ball, but that all players would have the same overall transmit rate. In such a system, a player's reflected radiation detection system could be activated only for a short time after his or her device transmits its radiation "ping" or data transmission, to help prevent unwanted data reception and sensor activation. One potential downside, however, would be that such a technique could potentially limit a single device's ability to detect the ball quickly, due to limitations on the average transmit rate (i.e., due to delays between transmissions).

Another method for limiting or eliminating "packet collisions" would be to "channelize" the devices on each player. Because the passive frequency doubler can operate on many frequencies in a narrow band, each player could use a slightly different frequency within the same broader band. Then, each player's detector could be tuned to "look" within a narrow band around two times the transmitted frequency. Such "channelization" also could be used to distinguish one team's data from the other team's data during the game or other activity. Other "collision avoidance" techniques also may be utilized without departing from this invention. Collision avoidance features also may be used with other proximity and possession systems and methods described above, if desired, without departing from this invention.

4. Other Potential Proximity/Possession Detection Technology

Other sensing systems and detection arrangements may be used for determining proximity and/or ball possession without departing from this invention. For example, ultrasound based proximity detection may be utilized, particularly for very close range ball proximity detection applications. Ultrasound systems may work using reflected radiation techniques similar to the RADAR techniques described above. Infrared radiation detection systems (both passive and active systems) may be utilized to detect ball proximity. Micro-Electro-Mechanical ("MEMs") devices, such as accelerometer and/or gyroscope devices (e.g., fabricated using semiconductor lithographic processes) also may be incorporated into a ball. Hall-effect sensing may be used with magnets in either the ball or shoe to detect proximity, particularly for short range applications. The inclusion of such devices in a ball may be particularly useful as adjunct sensors, e.g., to help determine when a ball has been kicked, and optionally, which player made the kick (e.g., by time stamping the data relating to the sensed contact in both the ball data and the various player's shoe data, etc.), kick force, kick speed, etc.

Some more specific examples are described below. One or more of these possession determination systems and methods may be used in conjunction with one or more of the speed/distance measuring systems described in more detail above.

In some systems and methods in accordance with examples of this invention, a magnet may be suspended in the center of the ball 130, and the footpod 106 may be equipped with a magnetometer (e.g., a compass sensor that measures Earth's magnetic field). This system may function, for example, by detecting small changes in the Earth's magnetic field due to the magnetic field emitted by the ball 130, which indicates the ball 130 is within a certain distance of the player's foot (and hence a certain distance from the magnetometer of the footpod 106). From this type of detection, physical contact with the ball and/or close proximity of the athlete to the ball may be inferred.

As another more specific example, one or more small tags may be built into the construction of the ball 130. A signal would be emitted by a sensor/receiver on the player. When the tag in the ball 130 receives the signal, it bounces it back at exactly double the frequency (e.g., using the frequency doubler features built into the ball as described above). The receipt of this doubled frequency signal by the sensor/receiver (e.g., in the footpod 106) indicates the ball 130 is within a certain range of the sensor/receiver (e.g., dependent on the strength of the initial signal). As some even more specific examples of this aspect of the invention, a sensor/receiver may be placed in both of the player's shoes 104 and have a short required working range (e.g., about 30 cm). In this case, each detection of the ball 130 would infer a physical contact with the ball 130 by the player's shoe 104. Alternatively, if desired, a sensor/receiver may be located in just one of the player's shoes 104 or on the player's body (such as waist-worn component 108) and have a larger working range (e.g., about 1-2 m). In this case, each detection would infer proximity of the player to the ball 104, or that the player is in possession and control of the ball 104.

Moreover, in a similar manner to the way player-to-ball proximity may be measured, systems and methods according to at least some examples of this invention may determine player-to-player proximity. As another more specific example, modules carried by each player may wirelessly communicate with one another when within a predetermined distance or range from one another (e.g., via a peer-to-peer network) to provide an indication of player-to-player proximity.

D. Ball Motion Related Metrics

Other useful metrics for many types of team sports relates to the speed at which the ball moves during play, e.g., as a result of a kick, throw, hit (e.g., with a bat, stick, arm, foot, racket, etc.), etc. More specific types of metrics that may be of use include, for example, ball speed, ball spin, linear ball speed, spin speed, spin direction, ball transfer speed (the term "transfer," as used in this context, generically means movement of the ball due to athlete interaction, such as a kick, throw, hit, header, etc.), ball transfer force, etc. Combining ball oriented metrics like these with various player oriented metrics (e.g., due to shoe or player body oriented sensor data and interaction between shoe or body oriented electronics and ball oriented electronics, as described above) or other data, such as possession, speed, time, etc., can provide other useful information, such as the identification of the player that kicked or otherwise propelled the ball, number of ball "touches" or contacts for various specific players, goal success and credit to the appropriate player, pass attempt success (e.g., whether the pass successfully reached a player on the same team), steals, missed passes, turnovers, etc.

Providing sensors in various types of balls, such as soccer balls, is known in the art. For example, various electronically enhanced balls that measure metrics, such as spin, speed, curve, trajectory, pressure, contact, and the like, are described in patent applications owned by Cairos Technologies, AG and in patents naming David J. Martinelli as the inventor. These patents include: U.S. Pat. Nos. 6,073,086; 6,157,898; 6,148,271; 6,151,563; U.S. Published Patent Appln. No. 2007/0191083; U.S. Published Patent Appln. No. 2007/0059675; U.S. Published Patent Appln. No. 2007/0060425; U.S. Published Patent Appln. No. 2007/0299625; U.S. Published Patent Appln. No. 2008/0085790; U.S. Published Patent Appln. No. 2008/0084351; U.S. Published Patent Appln. No. 2008/0088303; U.S. Published Patent Appln. No. 2008/0090683; PCT Published Patent Appln. No. WO2008/080626; PCT Published Patent Appln. No. WO2008/104,247; and PCT Published Patent Appln. No. WO2008/119479. Each of these patent documents is entirely incorporated herein by reference. The various ball oriented sensors or other electronics or structures described in the possession/proximity discussion above may be incorporated into a ball structure in the same manner as described in these various patents and publications.

E. Example Team Features

Figure 14:
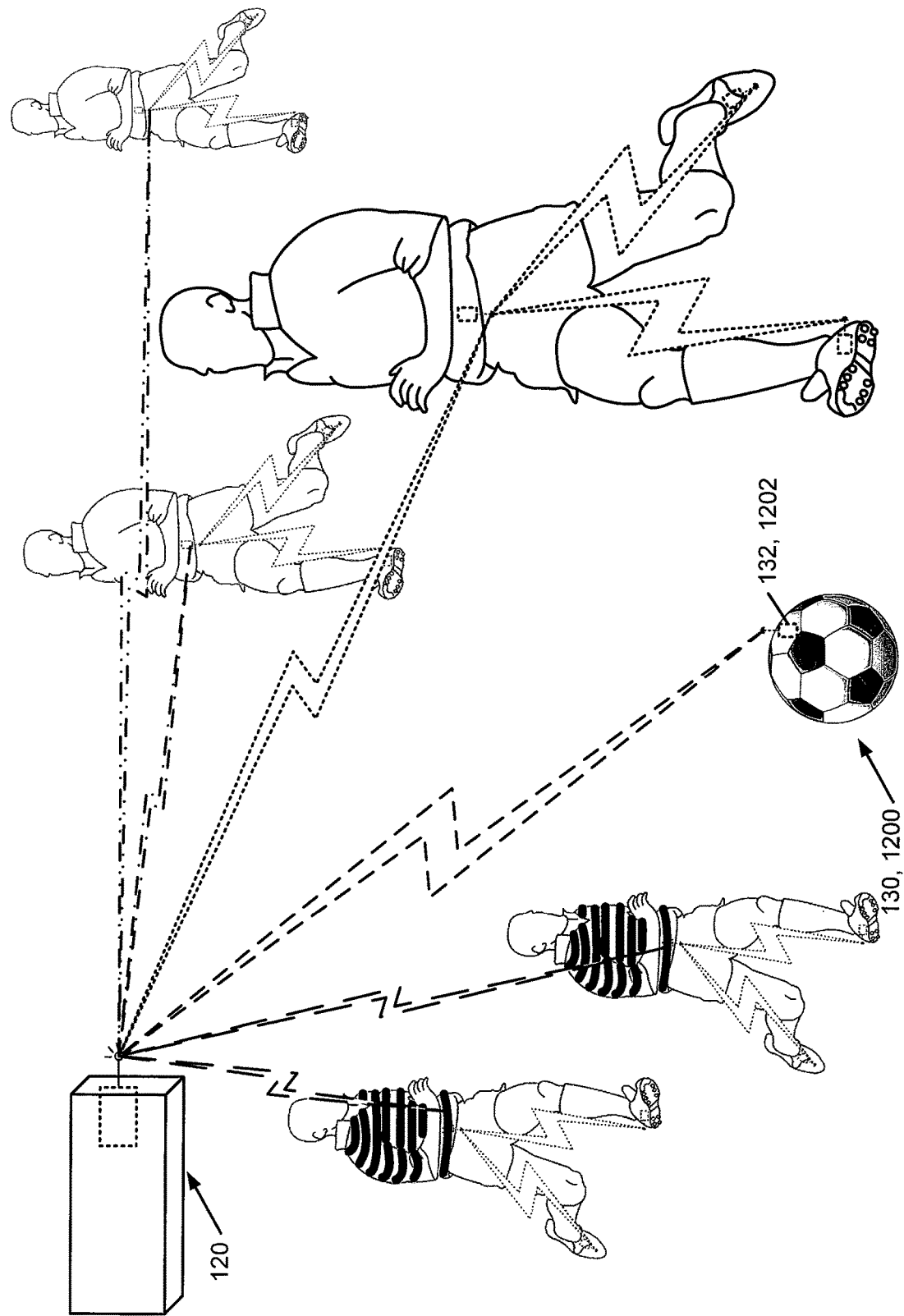
FIG. 14 is a diagram that aids in the discussion of multi-player concurrent use of systems and methods in accordance with this invention.

As illustrated in FIG. 13 (and as alluded to above) and FIG. 14, systems and methods in accordance with this invention are not limited for use with a single player. Rather plural players, optionally on both teams, may be equipped with active transmitters and/or receivers that interact with the transmitting, receiving, and/or reflecting equipment provided with the ball 130 or 1200. When plural players on a team are equipped with appropriate electronic equipment as described above, it can be determined when the ball 130, 1200 moves from one team member to another. Such systems and methods can be useful for providing various team metrics, such as team possession time, passing streaks and efficiency, pass accuracy, turnovers, steals, tackles, etc. All data (e.g., from the players on both teams, from the ball 130, 1200, etc.) can be transmitted to a single remote computer system 120, or optionally, if desired, to different remote computer systems 120 (e.g., one for each team, one for each player, etc.). As yet another example, if desired, the data can simply be logged during the game or practice session (as described in conjunction with FIGS. 4 and 5 above) and later downloaded or otherwise accessed for use by the individual players, coaches, etc. The various player's data also could be intercommunicated to one another via peer-to-peer networking so that players could compare performances quickly and easily, e.g., on the sidelines, in the locker room, etc.

Team oriented metrics also allow team players and coaches to look at both the individual and team data and determine various features or characteristics of play, such as which players play best together, the strengths and weaknesses of individuals, the strengths and weaknesses of various groupings of players, who is ball "hogging," who is insufficiently involved in the game, who is loafing, etc. The coaches and/or team members can evaluate the data in real time (e.g., on the sidelines, in the coach's box) during the game or practice session to better understand whether a combination of players is working (or, potentially, to discover an injury or other need for substitution by noting that a player's performance has suddenly fallen off). Also, the team data can be used to motivate the individuals to challenge one another and/or to motivate them to make efforts to improve the overall team statistics.

F. Example Website Features

Additional aspects of this invention relate to the presentation of data to the player, coach, trainer, or other person(s). Such systems help the player measure and track his or her capabilities, mark improvements over time, determine areas that require additional work, etc. Data can be collected over single games, portions of games, single practices, portions of practices, multiple games (or portions thereof), multiple practices (or portions thereof), multiple seasons (or portions thereof), etc.

Figure 15:
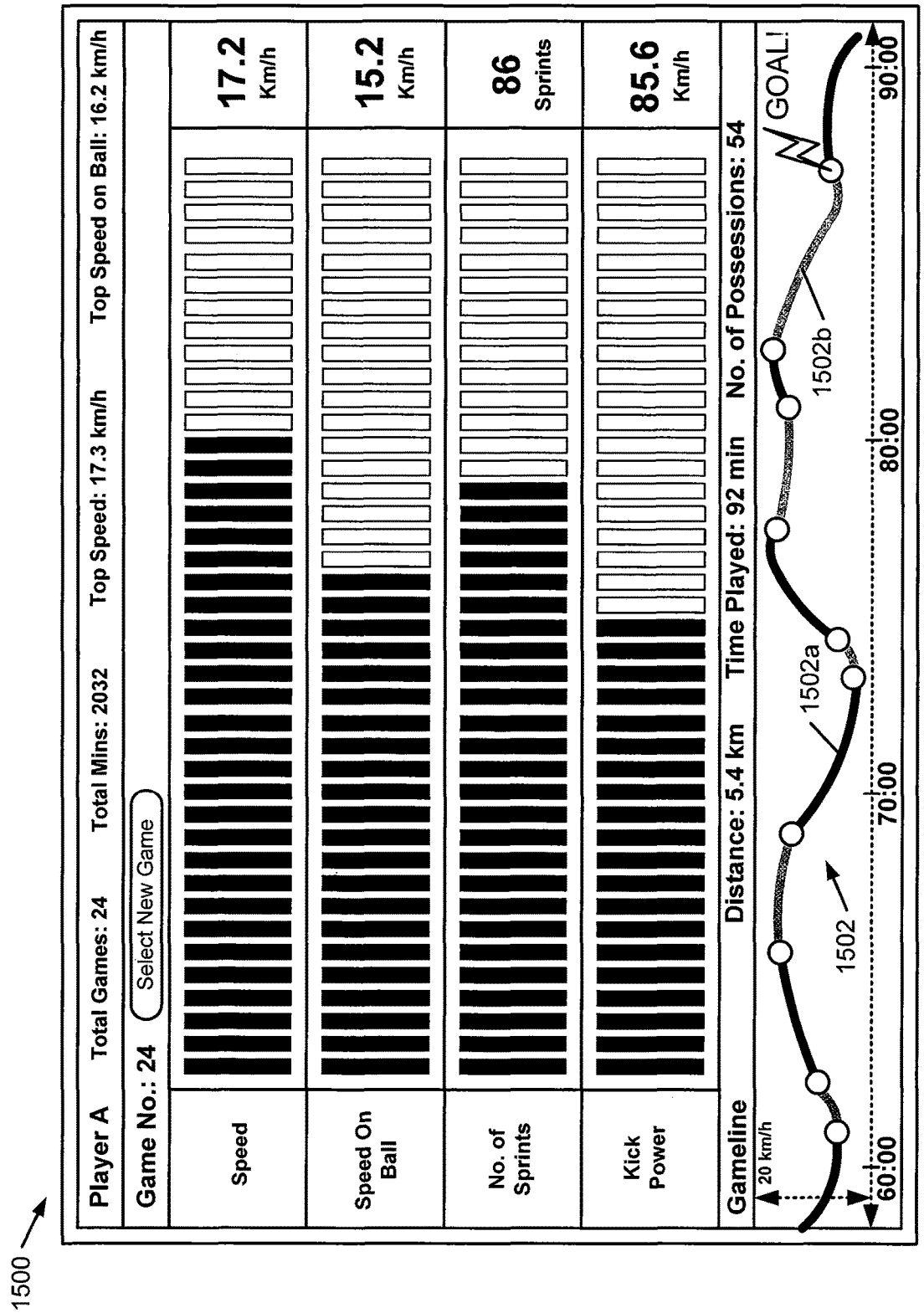
FIGS. 15-18 illustrate example features of user interfaces that may be provided by systems and methods according to examples of this invention.

FIG. 15 illustrates an example user interface screen 1500 that may be used in systems and methods in accordance with at least some examples of this invention. As shown in FIG. 15, the interface screen 1500 may present much information to the player, including information relating to a specific game or practice session, as well as information relating to more long term use of systems and methods in accordance with this invention. For example, as shown in FIG. 15, user interfaces 1500 in accordance with this invention may provide information relating to the overall total number of games played by the player, the total overall minutes logged by the player using the system, the player's top speed over that time period, and the player's top speed while in possession of the ball (e.g., while he was personally in possession of the ball or within close proximity to it, not while the team was in possession).

The interface screen 1500 also provides information for an individual game (with the ability to select among the various stored games on the system). As illustrated in FIG. 15, in this example interface, the screen 1500 displays information relating to the player's movement speed during this specific game (i.e., Game 24), movement speed while in possession of the ball during this specific game, the number of "sprints" during the game (e.g., the number of times that the player's movement speed exceeded a predetermined threshold, such as 75% of their top speed), and the player's highest "kick power" during the course of the game (e.g., the highest ball speed logged from the player's kick). Also, if desired, the user interface could be adapted to allow user selection of various different metrics or information to be displayed.

The "Gameline" portion of this example interface screen 1500 includes information relating to the specific game displayed. For example, in the illustrated screen 1500, the Gameline includes information indicating the entire distance that the player moved during the game, the number of minutes played, and the number of "touches" or times that the player had "possession" of the ball. Additionally, in this example, the Gameline includes information regarding the user's speed over the course of the game, as well as the times that the player's team had possession of the ball. In this example, the dark black portions 1502a of the player's movement velocity line 1502 indicate when the player's team did not have possession of the ball and the lighter gray portions 1502b of the player's movement velocity line 1502 indicate when the player's team had possession of the ball. The visible portion of the movement velocity line 1502 can be changed so that any desired portion of the game can be displayed (the 60 to 90 minute time period is displayed in this illustrated example), or an entire game (or the portion in which the player played) can be displayed in a single view, if desired. Other metrics may be displayed in the Gameline portion of the interface 1500, if desired, without departing from this invention, either in place of this movement velocity time line 1502 or in addition to it (such as the times when the player kicked the ball, the player's goals (as shown), the player's successful passes, the team's goals, etc.). Also, if desired, user interfaces according to the invention could be designed to allow user selection of various different metrics in the Gameline portion.

Figure 16:
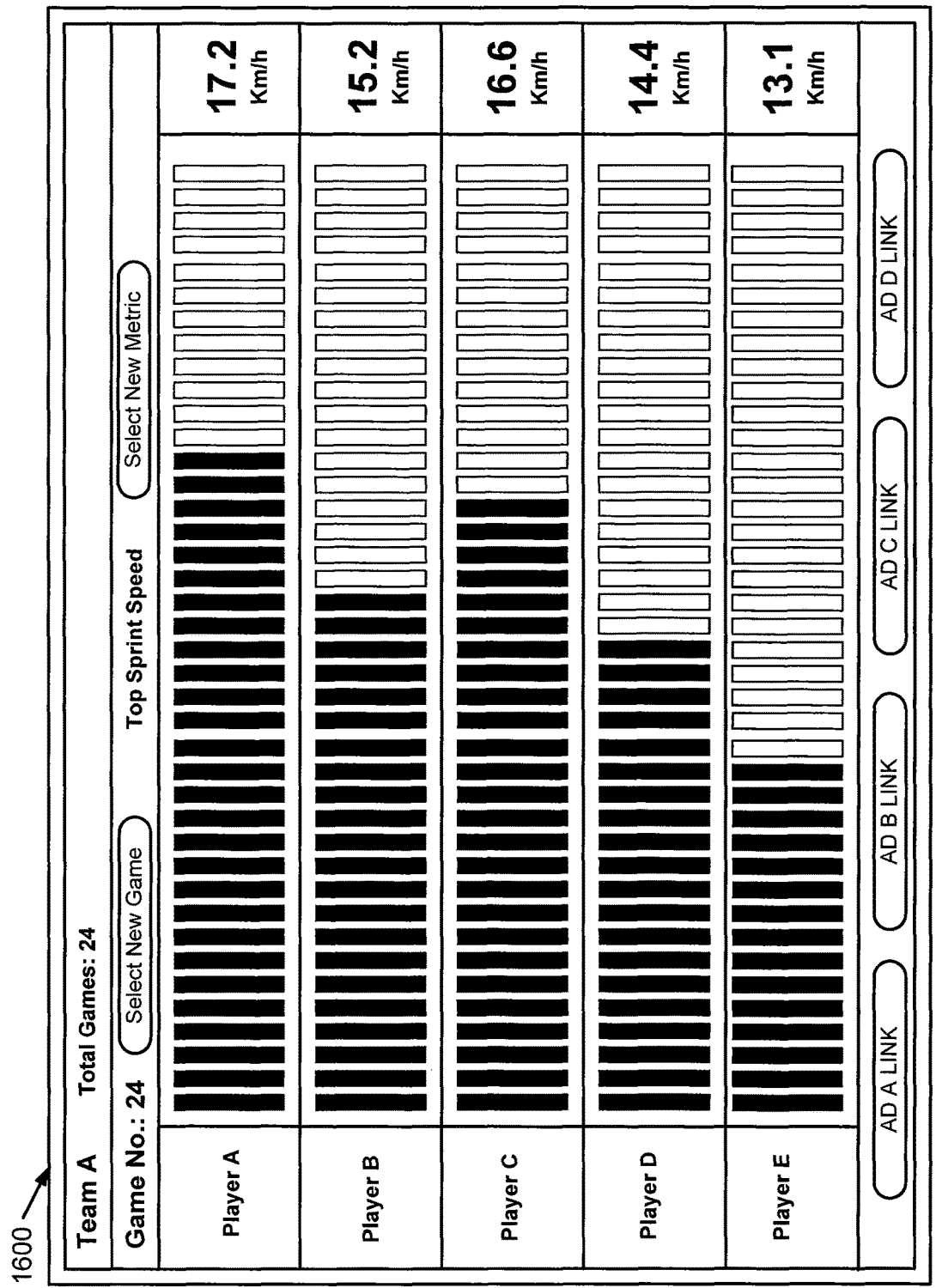

User interfaces in accordance with at least some examples of this invention also may display team information (or even competitor team information), if more than one player is equipped with the sensors and detectors in accordance with this invention. FIG. 16 illustrates an example user interface screen 1600 in which data from five players are displayed in a single screen. In this example, the player movement velocity data (e.g., top sprint speed) for five players that participated in a single game (Game 24) is displayed, e.g., so that the players or coaches can compare performance characteristics. Furthermore, in this example interface screen 1600, data for other games can be selected, or data for other measured metrics may be displayed in this plural player comparative manner (e.g., speed on ball, number of sprints, number of touches, kick power, number of successful passes, number of steals, number of turnovers, etc.). Other team data or other measured metrics also may be made available and displayed in this type of user interface screen without departing from this invention.

Figure 17A:
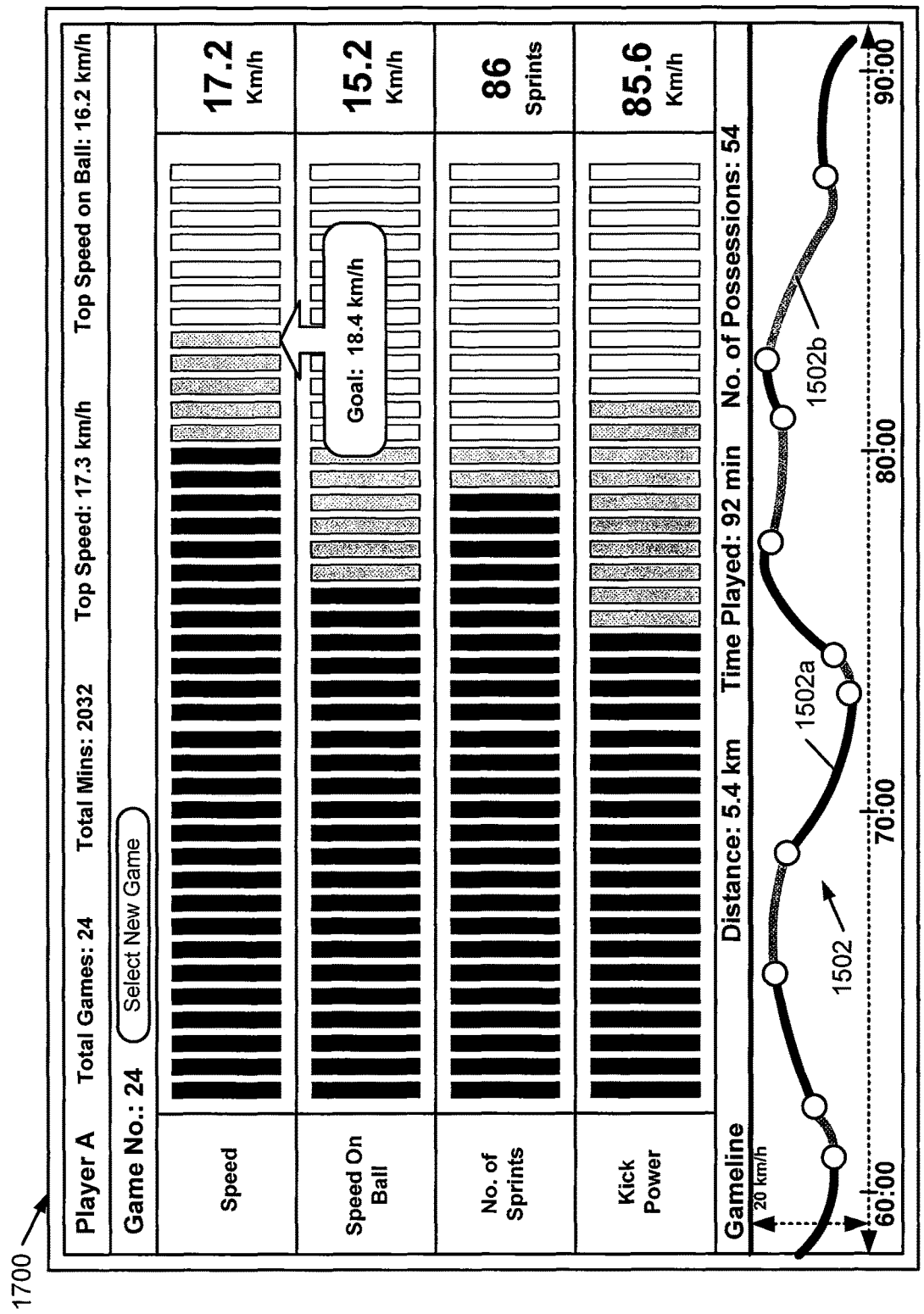
Figure 17B:
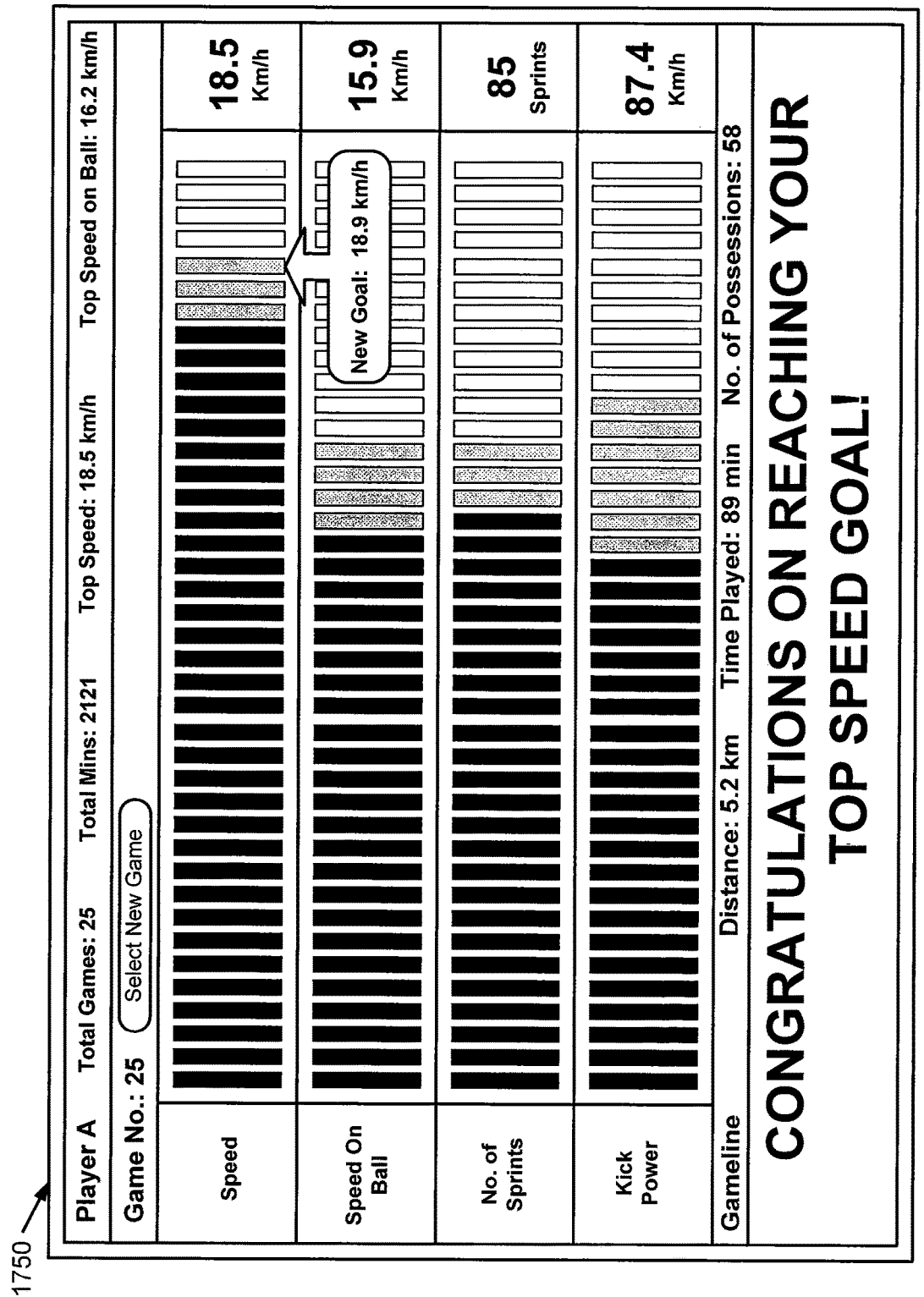

Systems and methods in accordance with at least some examples of this invention may include "goals" or "challenges." While the goals may be set by the individual player for himself or herself, optionally, the goals or challenges may be set by a coach, a teammate, a competitor, etc. FIGS. 17A and 17B illustrate an example. FIG. 17A illustrates a user interface screen similar to that of FIG. 15, but in this example, each data metric further includes "grayed out" blocks that represent a player's "goal" or "challenge" for that metric. For example, in FIG. 17A, the data from Game 24 is displayed with an indication of the player's performance in that game (the blackened in boxes) and an indication of where the player's performance stood with respect to their "goal" or "challenge" levels (the grayed out boxes). The specific metric for the "goal" or "challenge" may be displayed in any desired manner, e.g., by clicking on the last box associated with the goal or challenge, by hovering over a grayed-out box, through a continuous display, etc. Notably, in this illustrated example, the system indicates that the player's overall top "speed" goal or challenge is 18.4 km/h, while in the present game they had only run at a top speed of 17.2 km/h.

In the next game (Game 25), however, as illustrated in the user interface screen 1750 of FIG. 17B, Player A achieved his or her speed goal by running 18.5 km/h. In this instance, systems and methods in accordance with at least some examples of this invention may provide a congratulatory message (e.g., textually, visually, audibly, etc., note the changes in the Gameline portion of FIG. 17B as compared to FIG. 17A). Furthermore, if desired, in an effort to keep the player motivated, a new "goal" or "challenge" can be calculated and displayed for the player. Also, if desired, when presented as a challenge from a third party, systems and methods in accordance with at least some examples of this invention may send a message to the challenger (or offer to let the player compose a message to his or her challenger) to advise that the challenge had been met. Other "rewards," motivational information, or other interaction may be provided, if desired, without departing from this invention.

Figure 18:
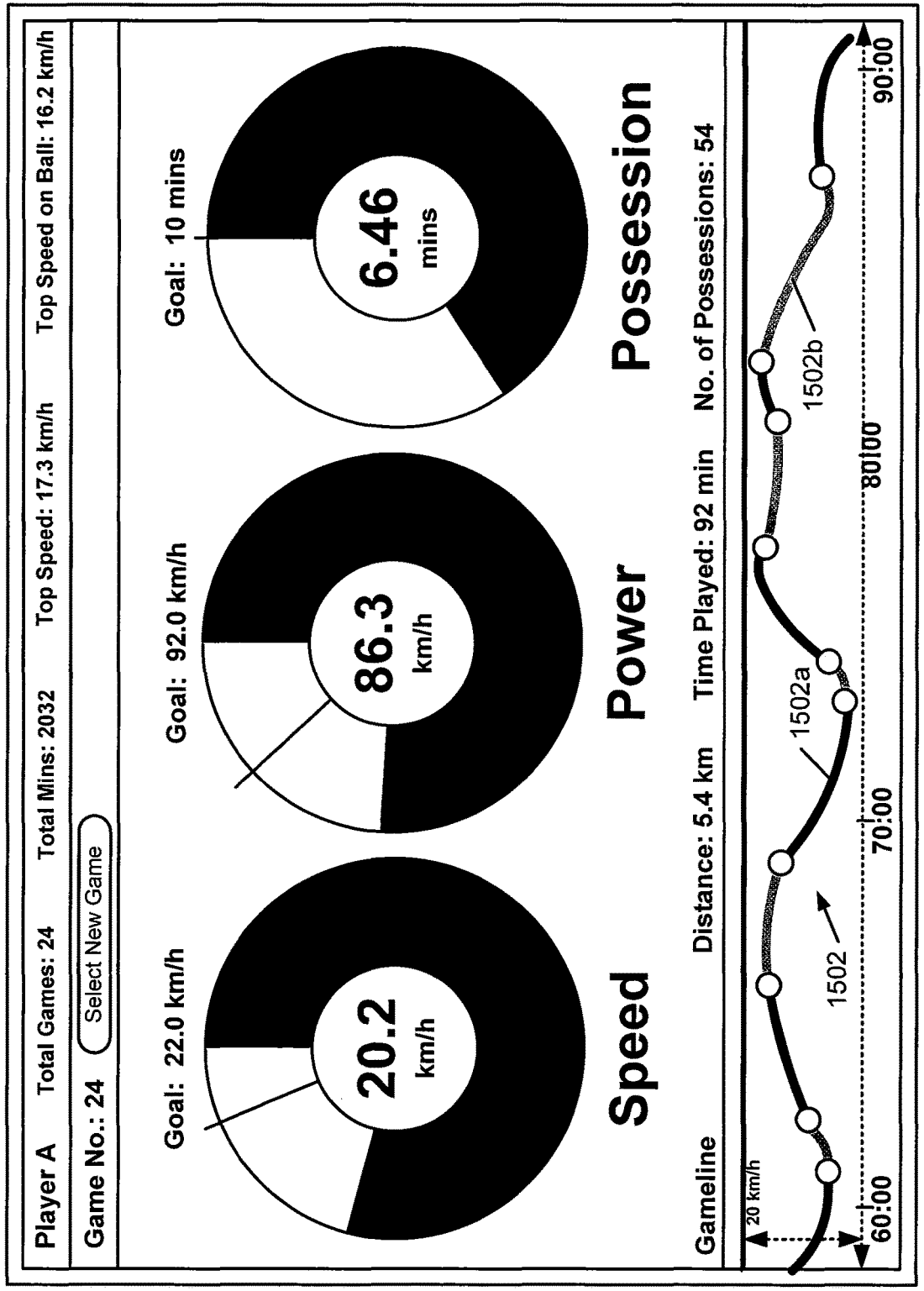

User interfaces for athletic performance monitoring systems and methods in accordance with this invention may take on a wide variety of forms and formats and provide a variety of different types of displays and information without departing from this invention. FIG. 18 illustrates another example user interface screen 1800 in which player speed, kicking power, and individual possession information is displayed on a more circular graph (as compared to the linear graphs of FIGS. 15-17B). FIG. 18 also shows a player possession time metric as opposed to the speed on ball and number of sprint metrics provided in FIGS. 15, 17A, and 17B. Displays of other metrics or combinations of metrics are possible without departing from this invention. Other graphical or other displays of the desired metric information also may be provided without departing from this invention.

G. Throwing v. Kicking Determinations

In at least some example systems and methods according to this invention, it may be desirable to distinguish between situations in which a ball or piece of sporting equipment has been thrown and when it has been kicked. This may be useful in various sports, such as soccer (e.g., to determine when play resumed and how it resumed, as will be described in more detail below) and basketball (e.g., to determine whether possession should be awarded to the other team). A determination of throwing v. kicking also may be useful for determining other metrics, such as possession time in soccer, as the throwing v. kicking determination may be useful in helping to determine when a ball goes out of bounds (e.g., on the side) during a soccer game (e.g., time between a throwing action and a previously determined kicking action may be considered "out of bounds" time in soccer (as a throwing action often is used to restart play from an out of bounds condition), and that amount of time may be deducted from a team's determined ball possession time). Aspects of this metric also may be useful in basketball, for example, to determine when the ball struck the ground (more like a "kicking action" sensor response, as described below) as opposed to being pushed with a hand (such as for a shot or pass).

In accordance with at least some examples of this invention, as illustrated in FIGS. 19A and 19B, output from one or more pressure sensors (e.g., a ball mounted pressure sensor and/or a foot mounted pressure sensor) and/or one or more accelerometers (or other inertial sensing device) (e.g., ball mounted and/or foot mounted) may be used for determining whether a ball has been thrown or kicked. FIG. 19A illustrates the ball sensor responses during a typical throwing action (such as a throw-in in soccer, a shot in basketball, etc.) and FIG. 19B illustrates the ball sensor responses during a typical kicking action (or a dribble off the floor in basketball). As shown in FIG. 19A, the output from both a pressure sensor and an acceleration sensor during a throwing action will tend to be a slow, long signal (or, depending on the throw, there may be little to no pressure signal at all from a simple throwing action). During a kicking action, however, as illustrated in FIG. 19B, a relatively short and strong impulse signal is generated by both the pressure sensor and the accelerometer sensor followed by a low-rate slowdown of the ball (e.g., due to aerodynamics, gravity, etc.). The pressure change inside the ball (or other object) is much slower when thrown as compared to when kicked, but the pressure change may last a longer time during the course of a throw event. Additionally, the accelerometer output will tend to constitute a much longer signal and lower level of acceleration from a throw as compared to a kick. These differences in sensor output between FIGS. 19A and 19B will allow systems and methods in accordance with examples of this invention to distinguish between throwing actions (such as throw-ins in soccer, shots or passes in basketball, etc.) and kicking actions (or other similar actions that will generate a similar pressure and accelerometer output spike, such as ball contact with ground (e.g., a dribble), ball contact with a basketball rim, ball or puck contact with a goalpost or hockey stick (e.g., in football, hockey, soccer, etc.)).

H. "Explosiveness" Determinations

Figure 20:
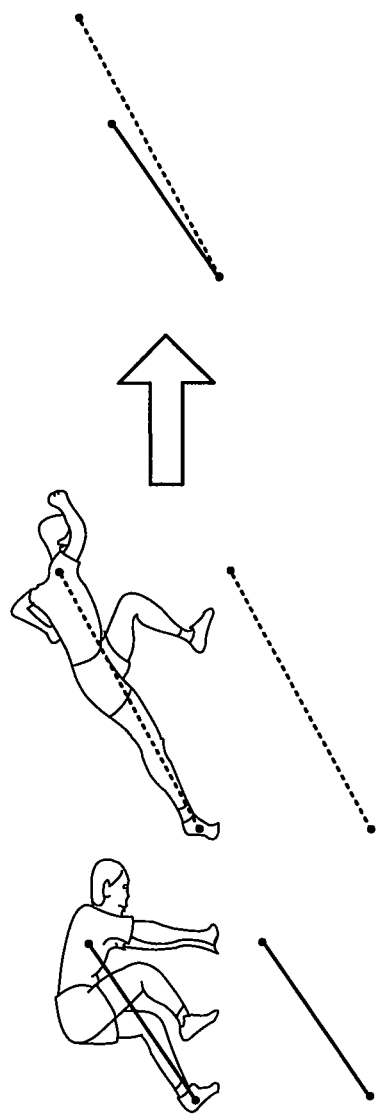
FIG. 20 assists in explanation of detection and/or measurement of an "explosiveness" metric in accordance with examples of this invention.

FIG. 20 illustrates an example of features that may be involved in determination of an "explosiveness" or "power" metric. Some metrics that may be useful in athletic performance monitoring systems and methods according to at least some examples of this invention relate to ways of determining how hard an individual is working over the course of a game or practice session. FIG. 20 illustrates various features involved in determining one example "explosiveness" metric. When athletes are in a crouch position (e.g., as shown in FIG. 20, such as sprinters, football linemen, backs, or other players, etc.), their effectiveness at the start of the activity is often determined by how quickly they spring into action (e.g., get out of the starting blocks, get out in front of rushing defensive players to make a block, etc.). As shown in FIG. 20, determination of the distance between the athlete's feet and his/her upper body or torso, and the rate of change of this distance, can be used to determine an "explosiveness" metric that may be a gauge of the athlete's performance. Note, for example, the differences in orientation and length between the foot based module and the torso based module from the crouch position (the solid line) and the initial "explosion" position (the broken line). Measuring and tracking the distance and/or angle and their rates of change may be used to determine various features or other metrics, like initial explosiveness, explosiveness over the course of a game or training sessions, improvements in explosiveness, effectiveness of training or conditioning, etc.

This measurement system may utilize two sensors (e.g., wireless sensors) or other modules that allow determination of the relative distance between two points (e.g. a foot based point and a torso or body core based point). The two sensors may report their positions to thereby allow their relative positions to be determined, and this information may be stored (e.g., in one of the sensors or modules, on another athlete carried device, such as a mobile phone, watch, PDA, audio/video playback device, MP3 player, etc.), transmitted to another location (such as a remote server, a laptop or other computer, etc.), etc.

Similar explosiveness or power metrics also could be used, for example, tied to a jumping action, such as a jumping action in basketball (or other sports).

Figure 21:
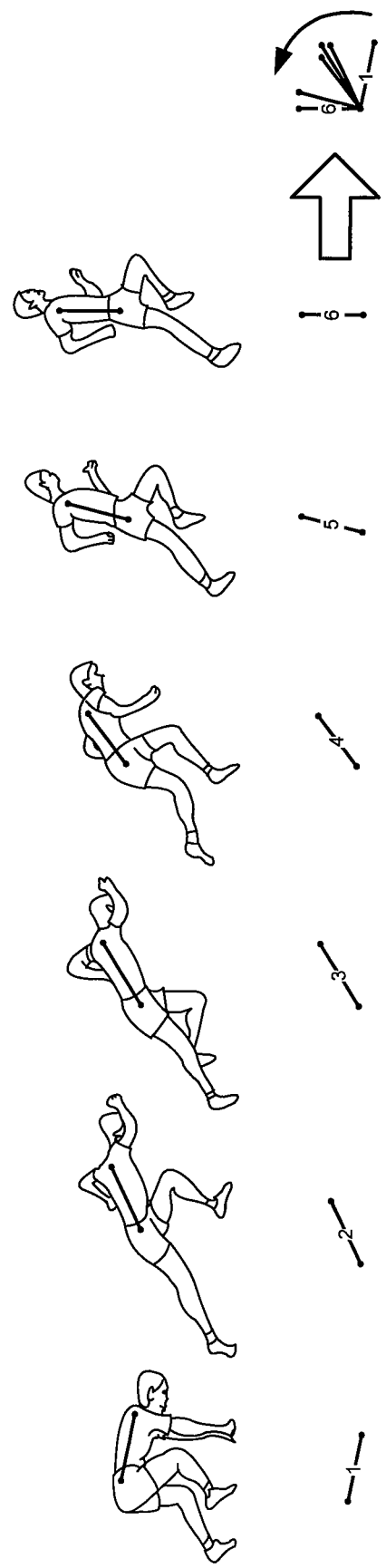
FIG. 21 assists in explanation of detection and/or measurement of an acceleration metric in accordance with examples of this invention.

FIG. 21 illustrates another potential manner of measuring explosiveness or power metrics by determining the player's acceleration. Generally, as illustrated in FIG. 21, when accelerating (as shown toward the left of FIG. 21), an athlete's center of mass and/or torso are generally located ahead of his/her feet. When a steady state pace is achieved (or when slowing down, as shown more toward the right of FIG. 21), the center of mass and/or torso more closely align vertically. In this example metric, the changing angle of the player's torso is determined, and the rate of change of this angle will provide information as to whether the athlete is accelerating, moving at a steady state pace, or decelerating.

As some more specific examples of the system of FIG. 21, the sensing system may include one or more of: an accelerometer, a gyroscope, or other rotation sensing devices. A sensor may be placed on the upper body and used to measure the rate of change of the angle of the upper body with respect to the body center (e.g., waist or pelvic area) and/or the feet. As another example, if desired, the rate of change of the gravity vector may be measured by an upper body mounted accelerometer. Optionally, if desired, this metric may be used in combination with foot or leg movement metrics to provide additional information or more detailed metrics with respect to specific activities. The foot or leg movement metric(s) may be measured using an accelerometer, a piezoelectric sensor, etc., to measure foot movement speed, foot impact force, foot loft time, etc. Combining the rate of torso angle change with other data, such as one or more of: body weight, height, foot location, foot movement, foot speed, or the like, may allow actual player acceleration to be determined.

Additional Potential Features and/or Metrics that May be Measured in Systems and Methods According to this Invention As noted above, while much of the above description has been provided in terms of use in a soccer environment, given the benefit of this disclosure, one skilled in the art could readily extend aspects and features of this invention to other team sports, such as basketball, American football, hockey, rugby, field hockey, lacrosse, baseball, cricket, volleyball, badminton, tennis, and the like. Different metrics may be tracked, stored, and/or displayed for different players or for different positions on the team (e.g., goalie versus center versus defensemen, etc.).

A wide variety of parameters or metrics may be measured and determined without departing from this invention. Including the various metrics described above, additional metrics that may be measured in systems and methods in accordance with at least some examples of this invention may include: vertical leap (e.g., with a body core mounted three axis accelerometer); number of leaps; jump height with the ball; jump height without the ball; team pace or match pace (an aggregate measure of speed, distance, and/or other data from all players on the team); on-field position and/or movement; on-field position and/or movement with respect to the ball's location; average speed intervals (on and off ball); top speed intervals (on and off ball); total distance moved (on and off ball); distance intervals; shot power; shots on goal; assists; blocks; saves; game duration; playing time; typical game statistics; etc. Data relating to any of these or the other metrics above may be combined and/or further processed, if desired, to provide other metrics or indices relating to the athlete's performance, such as a "hustle" or "intensity index," the number of shots without a goal, average number of shots between goals, tackles per game, minutes without giving up a goal, shot blocks, etc.

Another useful metric similar to one described above also may be termed "explosiveness," e.g., data and metrics tracking the player's initial movements from a slowed pace or stopped position. For example, this metric may include acceleration information relating to the first two or three steps. Additionally or alternatively, this metric may include information relating to the force applied to the athlete's foot or feet even before the athlete moves (i.e., as he or she prepares or "loads up" to take off).

Another useful metric may involve consideration of the differences in a player's performance over the course of a single game. If a player has a dramatic drop off later in the game, this information could be useful to the coach (e.g., to provide motivation, to induce substitution, etc.) or to the player (e.g., to induce work on conditioning, etc.).

Systems and methods according to this invention also may allow user input of other information relative to the game, such as temperature, humidity, wind conditions, field conditions (e.g., wet, dry, etc.), etc. Tracking these features may be useful to see how players perform under a variety of conditions and determining which players to field under a given set of conditions.

If desired, aspects of this invention also may include various automatic ON/OFF switching features, e.g., to preserve battery power for the actual game time but to assure that the desired data is captured. As one example, a referee, scorer, or coach could include a device that turns all devices ON and OFF from a central location. As another example, if desired, detection of the referee's whistle frequency could be used to turn the devices on and off.

Systems and methods according to examples of this invention also may allow an individual to compare his or her performance (e.g., any measured metric) to that of a professional athlete or another player (e.g., on a game-per-game level, on a metric level, etc.). Training advice or practice drills also could be downloaded to or provided to the player by systems and methods in accordance with this invention, optionally, based on the measured performance metrics stored in the system. Additionally, if desired, systems and methods according to examples of this invention also may be used to recreate an animation of the game (and the player's performance) on the computer screen after the game has been completed (or even while it is going on).

Aspects of this invention also may be useful for other purposes within the context of a team sport, such as a referee assistant (e.g., did a player have possession, was a player out of bounds, was the ball out of bounds, was the shot made before time expired, etc.). Coaches also could use features of the invention during practices, drills, or even during the overall game to determine which players should play, which players should play together, which players should not play together, as a motivational tool, when to substitute, etc.

Figure 22:
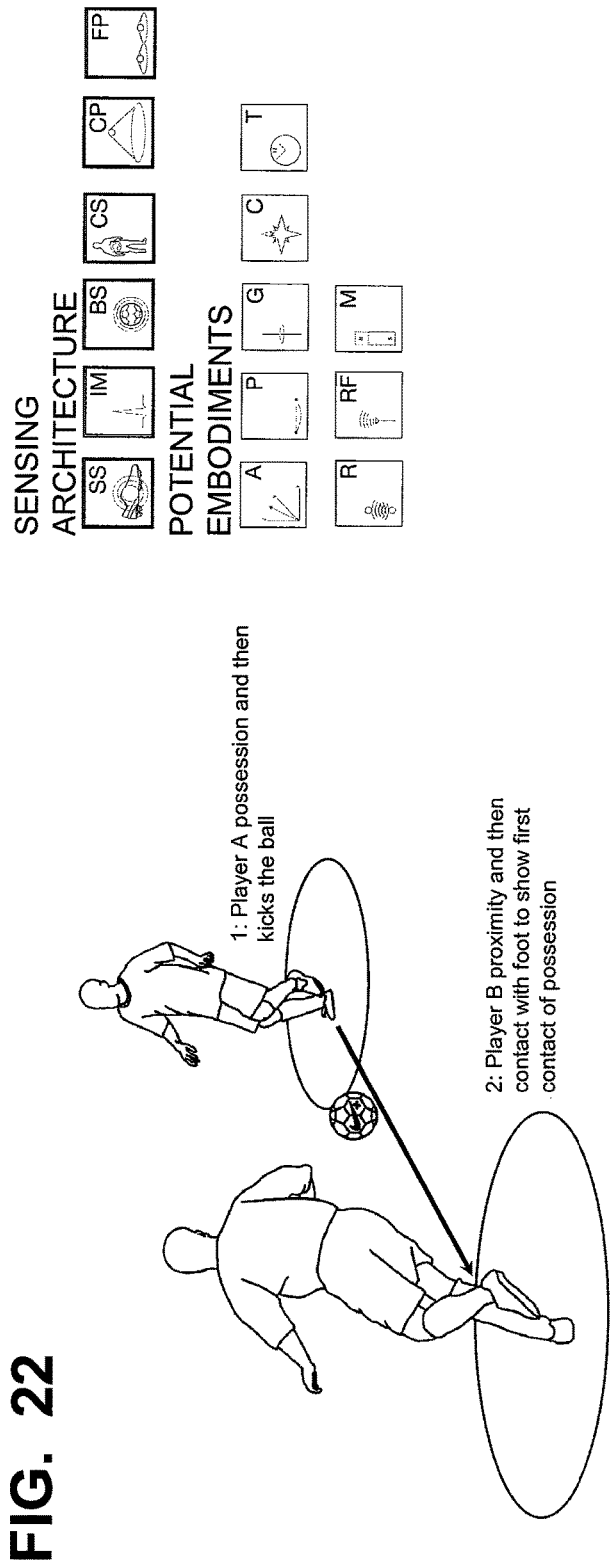
FIGS. 22 through 94 assist in explanation of detection and/or measurement of various athletic performance metrics, features, and/or other features of systems and methods in accordance with examples of this invention.
Figure 94:
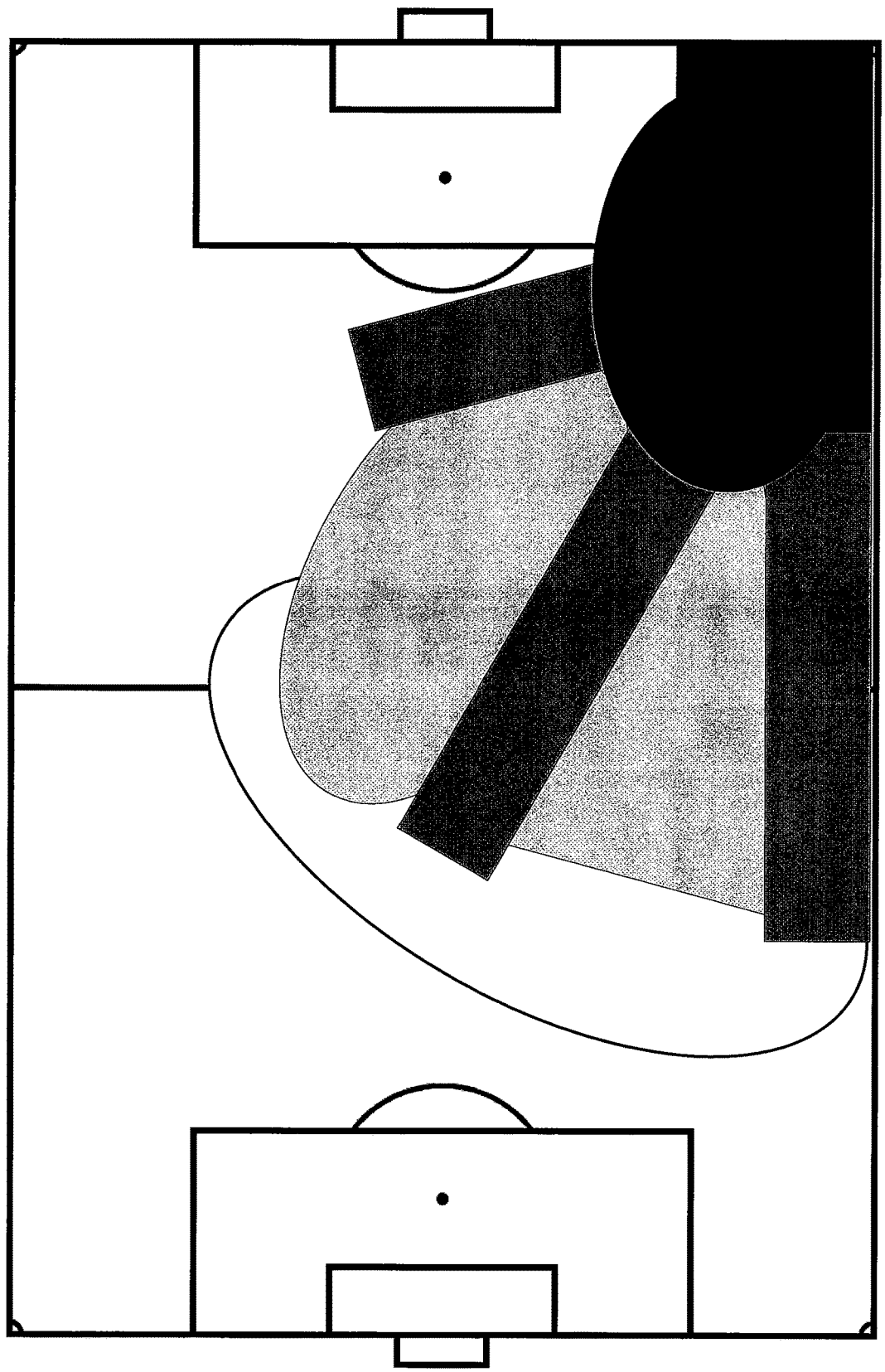

The following description, in conjunction with FIGS. 22 through 94, provides some detailed information relating to measurement of various metrics and various other features of systems and methods according to examples of this invention that may be useful in various environments, including for use in monitoring athletic performance in the context of soccer (e.g., for use in a soccer game, soccer training, soccer practice, etc.) or other team based sports. FIGS. 22 through 94 illustrate various soccer (or other sport) scenarios (e.g., typical game or practice events, types of plays, types of ball control or ball possession transfer, etc.) as well example "sensing architecture" and example sensors and/or combinations of sensors (called "Potential Embodiments" in FIGS. 22-94) that may be useful in collecting the data and making the measurements for determining features, aspects, and metrics based on that scenario. The following abbreviations are included in the various figures, and these abbreviations have the meanings provided below:

Motion Sensing Definitions:
CS—Core mass sensor (sensor(s) on the athlete's body core capturing player motion data)
SS—Shoe (or foot) based sensor (sensor(s) in one or more shoes to capture foot motion data)
BS—Ball Sensor (sensor(s) in the ball to capture ball motion data)

Proximity Sensing Definitions:
CP—Core mass proximity sensor (sensor(s) on the athlete's body creating a proximity sensing field around the player, e.g., as described above)
FP—Foot based proximity sensor (sensor(s) mounted on the shoes or near the foot creating a tight proximity sensing region between the ball and a foot (which may be the same as or similar to the core mass sensors described above))
IM—Impact sensor (a time stamped impact on a foot sensor and a ball sensor indicating foot/ball contact)

Sensor Types:
R—Radar based sensor system
RF—Radio (or radio frequency) based sensor system
GPS—Global positioning satellite based sensor system
M—Magnet based sensor system (e.g., Hall Effect sensors, etc.)
MC—Magnetic coil based sensor system
P—Pressure sensor system (e.g., piezoelectrics, etc.)
A—Accelerometer sensor system
G—Gyroscope based sensor system
T—Time sensor or clock
C—Compass (e.g., electronic compass)

FIGS. 22 through 35 illustrate various potential features for detecting interactions of soccer players with respect to the ball, e.g., during a game, practice session, etc. The features of these "player on ball" determination systems, methods, and metrics will be described in more detail below.

FIG. 22—Receive Possession:

To create useful metrics for the game of soccer, systems and methods according to at least some examples of this invention will have at least some manner of determining when possession of the ball starts (e.g., to determine individual player possession time, team possession time, etc.). Therefore, systems and methods according to examples of this invention include some manner of choosing and determining events that start the possession clock and/or keep the possession clock running. In accordance with this example of the invention, sensors in the shoe and the ball may be used to determine and start a possession event. Proximity sensing alone (e.g., player proximity to the ball, as described above) may not be sufficient to determine accurately when a possession actually starts for all uses, so additional sensing methods may be provided to more accurately determine when a possession time clock can be initiated in accordance with at least some examples of this invention.

As shown in FIG. 22, in this example system and method according to the invention, a sensing system in the ball (pressure sensor, accelerometer, gyro, magnetometer, etc.) detects an impact to the ball, and coincidently a sensor (accelerometer, piezo element, or other inertial sensing system) in the boot of a player matches the impact time exactly. This precise moment may be used in at least some systems and methods according to this invention to determine the start of possession. In other words, as illustrated in FIG. 22, when Player A kicks the ball toward Player B, Player B's proximity to the ball and then contact between Player B's shoe and the ball, optionally along with departure of the ball from the proximity of Player A, will be used to establish possession and start a possession time clock for Player B and/or continue a team possession time clock for one team (if Player A and Player B are on the same team) and/or start a new team possession time clock (if Player A and Player B are on different teams). Various examples of the sensing architecture and sensor systems that may be used for determining this metric are illustrated in FIG. 22.

Figure 23:
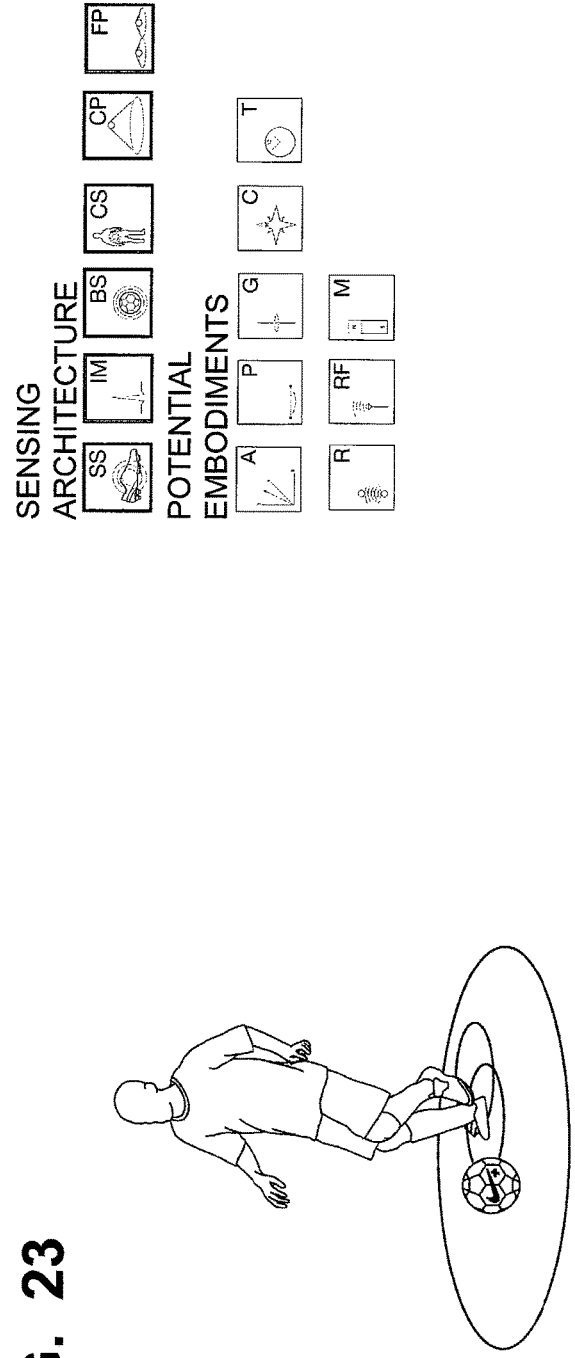

FIG. 23—Player Possession:

In addition to determining when an individual player's possession starts, systems and methods according to at least some examples of this invention further may wish to track how long an individual player maintains possession of the ball. FIG. 23 illustrates various example features of potential systems and methods for determining individual player possession. This example system and method according to the invention uses sensors in the shoe and the ball to start this event (as described above in conjunction with FIG. 22), and then uses proximity detection features to confirm that the player has kept possession after that initial contact and the length of time associated with this possession. For example, when the player kicks the ball out of their proximity (at least under certain conditions as will be described in more detail below) or if the player is tackled and loses possession (as will be described in more detail below), these events may be determined as possession ending events (which can be used to at least temporarily stop that player's possession time clock). Various examples of determining player possession and/or proximity may be used, as described above.

As some more specific examples, as noted above, a sensing system in the ball (e.g., pressure sensor, accelerometer, gyro, magnetometer, etc.) detects an impact to the ball, and coincidently a sensor in the boot of a player (e.g., accelerometer, piezo element, or other inertial sensing system) matches the impact time exactly. This precise moment determines the start of possession. Then, an on body proximity sensor can be used (e.g., as described above, such as a radar, radio frequency, or magnet system) to confirm that the ball remains in the field of proximity and (via the time counting sensor) the amount of time that the ball remains within this field of proximity (optionally, without another player having contact with the ball, which would constitute a change in individual possession (but not necessarily team possession)).

FIG. 24—Speed on Ball:

As described above, one metric that may be particularly useful for determination by systems and methods in accordance with examples of this invention constitutes a player's "speed on ball" metric (e.g., a measure of how fast a player moves while in possession of the ball). FIG. 24 illustrates an example system and method. In this example system and method, a proximity sensing system (such as radar, radio frequency, magnetic sensors, etc.) is used to determine when the ball is in proximity to the player. Impact sensing systems in the boot (accelerometer, piezo element, etc.) are matched to impact sensing systems in the ball (pressure sensor, accelerometer, gyro, etc.) to determine when the foot impacts the ball. Speed on ball is then determined as the speed at which the player moves while in continuous proximity to the ball, with repeated foot impacts to the ball, and/or as the speed at which the player moves while the ball is determined to continuously be in his/her possession.

As another alternative, systems and methods according to at least some examples of this invention may continue the "speed on ball" measurement metric (as well as a player possession metric as described above) even when the ball falls outside the core proximity sensing capabilities under certain circumstances. For example, the speed and ball and/or player possession metrics may continue running their clocks when the ball moves outside the core proximity sensing capabilities as long as: (a) the ball never is detected to be in the proximity of another player and/or (b) the amount of time the ball is outside the player's core proximity sensing range is below a specified time threshold. This would cover situations where a player is running fast and making long dribbles (which may extend outside the core proximity detection range) while still consistently maintaining control of the ball.

FIG. 25—Short, Break, and Long Dribbles:

As described above, output from an impact sensing system inside the ball (e.g., accelerometer, pressure sensor, etc.) may match timing with output from an impact sensing system inside the boot to time-match impacts so that systems and methods according to at least some examples of this invention will be able to determine when the ball is struck by a specific foot. A proximity sensing system also may be employed (e.g., magnetic sensing, RSSI, etc.) to determine when the ball is in proximity to the specific players on the field. A "dribble" action may be determined, e.g., by repeated foot/ball contacts by a single player. Combining a dribble action determination with other metrics, such as player speed/acceleration metrics, can provide other useful information for evaluating athletic performance. More specifically, systems and methods according to at least some examples of this invention can differentiate between different types of dribbles and allow determination of different metrics.

As some more specific examples, the following dribble types may be determined: (a) a "short dribble" can be defined as player dribbling the ball with a low player speed (e.g., below a threshold speed, optionally a threshold speed based on the individual player's top sprinting speed and/or average running speed), (b) a "break dribble" (or "break away" dribbling) can be defined as a player with an accelerating player speed, and (c) a "long dribble" can be defined as a player dribbling beginning with a break dribble followed by a steady player velocity and/or then repeated foot contact by the same player. Systems and methods according to aspects of this invention may further break up player possession time into the various times that the player spent in these various different dribbling activities.

FIG. 26—Knock On and Sprint:

This common play in the game of soccer may be detected by systems and methods according to at least some examples of this invention using a multitude of sensing systems and combining their outputs. An impact sensing system inside the ball (e.g., accelerometer, pressure sensor, etc.) is matched to an impact sensing system inside the boot to time-match impacts to know when the ball is struck by a specific foot, as described above. Additionally, a player speed sensing system (e.g., foot based, core-mounted inertial sensing based, etc.) may be used to determine player speed.

Using a determination of the start of possession as described above, one example sequence of events that could lead to a determination of a "knock on and sprint" event may include the following sequential steps:
a. Ball impact is detected along with a foot impact, determining start of possession;
b. The proximity sensing system determines when an opposing player comes within the possession radius;
c. The ball and shoe sensors then determine a kick by the player having possession;
d. The speed sensing system detects a sprint while the ball is located outside the proximity detection radius from the player;
e. The same player then runs onto the ball, and the proximity sensing system determines player/ball proximity;
f. Then, the start of possession determination methods described above are then used to determine the resumption of the player's possession.

The number of "knock on and sprint" events detected for an individual player during the course of a game (or other time period) may be determined as a metric, e.g., as a measure of the player's effectiveness at avoiding defensemen, as a player's ball control capability, etc.

FIG. 27—Close Control:

One important skill in the game of soccer is the ability of a player to keep the ball within very close proximity to himself or herself while still reaching very high running speeds. Systems and methods according to at least some examples of this invention may be used to determine a player's top speed (or average speed, etc.) when keeping the ball in close proximity. As some more specific examples, an inertial sensing system may be employed to determine player speed and movement distance (e.g., accelerometers, piezo elements, etc.), and an impact sensing system inside the ball (e.g., accelerometer, pressure sensor, etc.) may be matched to an inertial sensing system inside the boot to time-match impacts to enable determination of when the ball is struck by a specific foot. Optionally, sensor systems may be provided to enable determination of the path that the foot has traveled over the course of its movement (e.g., accelerometers, gyros, etc.). A proximity sensing system also is employed (e.g., magnetic sensing, radio frequency, radar, etc.) to enable determinations of when the ball is in proximity to the players on the field. Using such hardware, determination of "close control" may be performed as follows:
a. The proximity detection systems determine when the ball is close in to the player.
b. Speed is determined using an on-body or on shoe speed and/or distance system, such as an accelerometer, piezo element, or similar.
c. At no time during the run can the ball leave a defined proximity from the player.

Such a system may enable determination of the player's top speed, average speed, and/or other speed characteristics while at all times maintaining the ball within a defined proximity or distance from his/her body (i.e., movement speed while maintaining close control over the ball). Such a metric may be useful in identifying players with breakaway speed that will still have a good ability to maintain control and possession of the ball even at high speeds.

FIG. 28—Dribble Foot Distribution:

This example aspect of the invention combines an impact sensing system in each of the user's shoes and an impact detection system in the ball, as has been described above. Time correlated impact events between the ball and each individual shoe may be ascertained to enable determination of which foot struck the ball. This data can be logged over the course of a game (or any desired time period), and the system can store this information and/or wirelessly communicate the data to a remote location. The data can be presented to the player (or coach, etc.), e.g., as a chart, graph, histogram, etc., to inform the player how often they use each foot during dribbling. This metric also can be used at least in part to formulate a report for the athlete that includes suggestions on how to improve. This metric allows determination of the dominant foot used by the athlete, which can lead to further metrics (such as development of weak foot to provide better shots on goal, etc).

FIG. 29—Control of Incoming Ball:

This example aspect of the invention uses a combination of various sensing systems described above to create a skill metric describing how well a player deals with an incoming ball (e.g., from a pass, during a steal, etc.). A formula can be created by the combination of two or more of the following metrics, some of which are described above and some of which are described in more detail below): (a) Kick Style, (b) Speed of the Ball, (c) Proximity, (d) Deceleration of the Ball (as determined by inertial/pressure sensing systems in the ball), and/or (e) Player Speed. As a more specific example, if desired, a ratio of (Speed of the Incoming Ball+Player Speed)/Ball Proximity after first touch may provide a useful metric. If the ball is maintained in close proximity to the player during an incoming kick, this indicates good player control over the ball. Maintaining close proximity to the incoming ball after the player's first touch, particularly when the ball is moving at high speed and/or the player is moving at high speed, is even more difficult. Therefore, a high ratio as described above would provide one potential incoming ball control metric. Other control metrics may be determined, e.g., using the other metrics described above without departing from this invention.

FIG. 30—One Touch Pass:

A "one touch pass" is a frequently used play in soccer that can be very influential in the game, allowing for fast movement of the ball and creation of space between the ball and defensemen. A "one touch pass" determination may be accomplished in a manner similar to a combination of a "pass" determination and a "possession" determination as described above. In the "one touch pass" scenario, the ball comes into the player's proximity rapidly, strikes one of the player's feet one time (e.g., determined using time matched ball and boot impact sensors), travels out of proximity, and (optionally), into possession or proximity of a teammate. While the player making the one touch pass may not (and/or need not) get possession time credit (because his/her possession time is too short), counting the player's involvement in the play and/or counting the player's pass can be very valuable information and a very valuable metric (e.g., for determining various other data or metrics, such as assists, passing efficiency, etc.) in understanding the effectiveness of a particular player.

FIG. 31—Tackle Avoided:

For determination of this event and/or metric, output from an impact sensing system inside the ball is time matched with output from an impact sensing system inside the boot to enable a determination of when the ball is struck by a specific foot. A proximity sensing system also may be employed, as described above, to enable a determination of when the ball is in proximity to the various players on the field. A determination of a "tackle avoided" metric according to this example of the invention uses the above defined dribble metric and a contested time determination (e.g., defined as a time period when the ball is located within close proximity to players on both teams). The following sensor outputs may be utilized to determine whether a tackle has been avoided:
  a. A dribble or possession is recorded by or awarded to a particular player.
  b. The ball proximity sensing system detects a "contested time" event when two or more players, with at least one from each of the teams on the pitch, located within a predetermined proximity to the ball.
  c. A short time later, another dribble or possession determination is recorded by or awarded to the same player as in step a above, but with no other players in proximity to the ball (as detected by the proximity sensing system).

This sequence of events may be used to award a "tackle avoided" event to the player maintaining possession. Tabulation of such events may provide useful ball control metrics for the various players.

Figure 32:
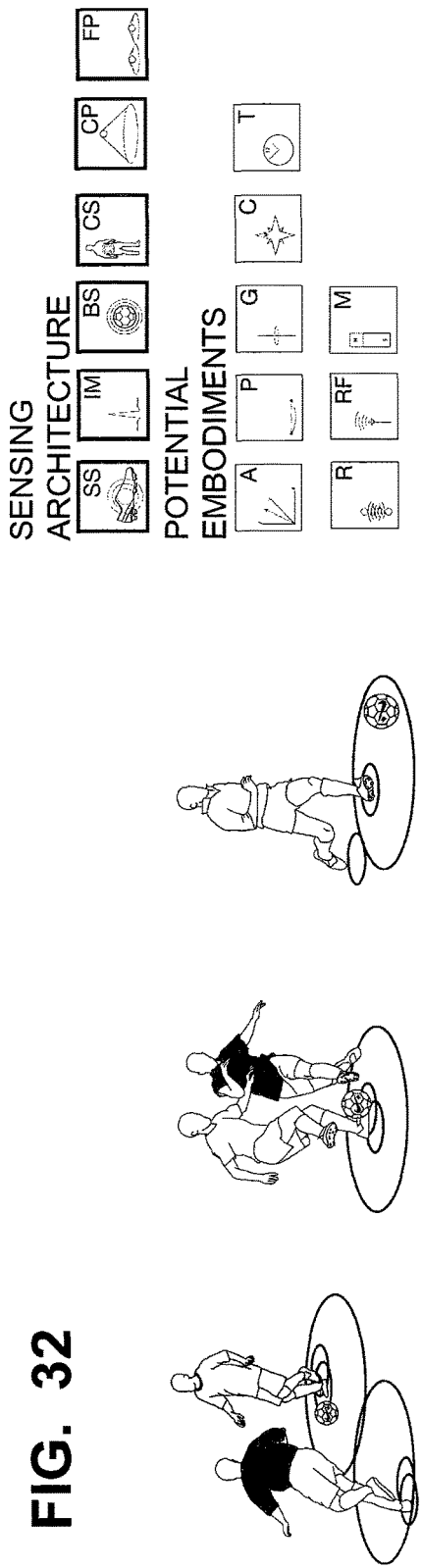

FIG. 32—Tackle Successful:

Determination of successful tackles also is a useful metric that may be tracked by systems and methods according to at least some examples of this invention. Determination of this metric is substantially the same as determination of the "Tackle Avoided" metric described above, except to have a successful tackle determination, an opposition player who was in proximity to the ball, a player that went in for the tackle, leaves in possession of the ball or successfully passes the ball to a teammate (a player on the opposite team from the player initially awarded possession). More specifically, as shown in FIG. 32, while Player A has possession of the ball (e.g., is dribbling), Player B from the opposing team moves in to attempt a tackle; Player A loses possession to Player B during the contested possession time; and Player B leaves with sole possession of the ball or passes the ball to a team member. Tabulation of successful tackle events may provide useful ball control metrics for the various players, e.g., for determining poor ball handlers, superior defensive players, etc.

Figure 33:
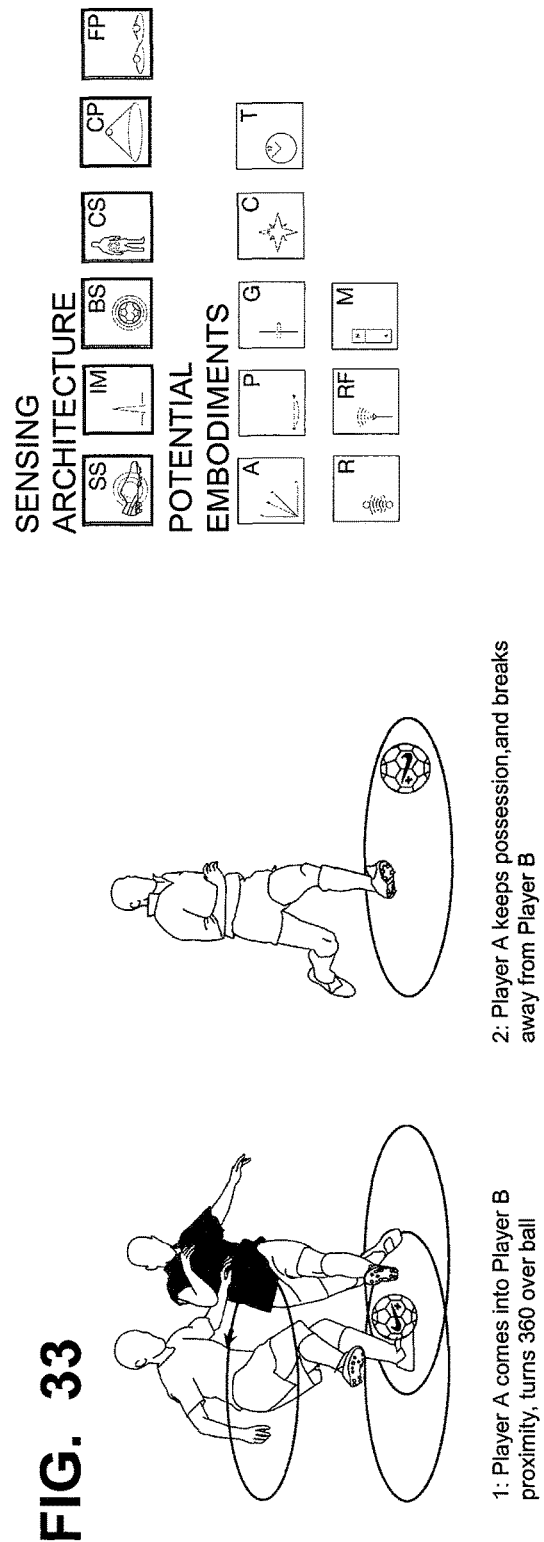

FIG. 33—A "Skin" Event:

Determination of a "skin" event may utilize an impact sensing system inside the ball and impact sensing systems inside the boots to enable time-matching of ball and boot impacts and to enable determination of when the ball is struck by a specific foot. This determination also may utilize a proximity sensing system to enable a determination of when the ball is in proximity to the various players on the field, and, in at least some examples, a core-mounted player rotational sensor (e.g., a compass sensor, a gyro sensor, an accelerometer, etc.) to enable a determination of which direction the player is facing and/or player relative rotational information. Using such a system, a "skin" may be defined by the following sequence of events:
  a. A first player receives a pass by registering proximity of the ball to the player as well as a simultaneous impact event on both the ball and boot.
  b. A second player is detected by the ball proximity sensing system (e.g., beginning a contested time period determination).
  c. The core mounted rotational sensor registers a 360 degree rotation of the first player (or some other significant rotational or other directional change move).
  d. The proximity sensing system from the ball senses only the first player in proximity of the ball (e.g., a break away from the second player plus possession of or proximity to the ball).
  e. A dribble or pass event is then recorded by the first player.

Figure 34:
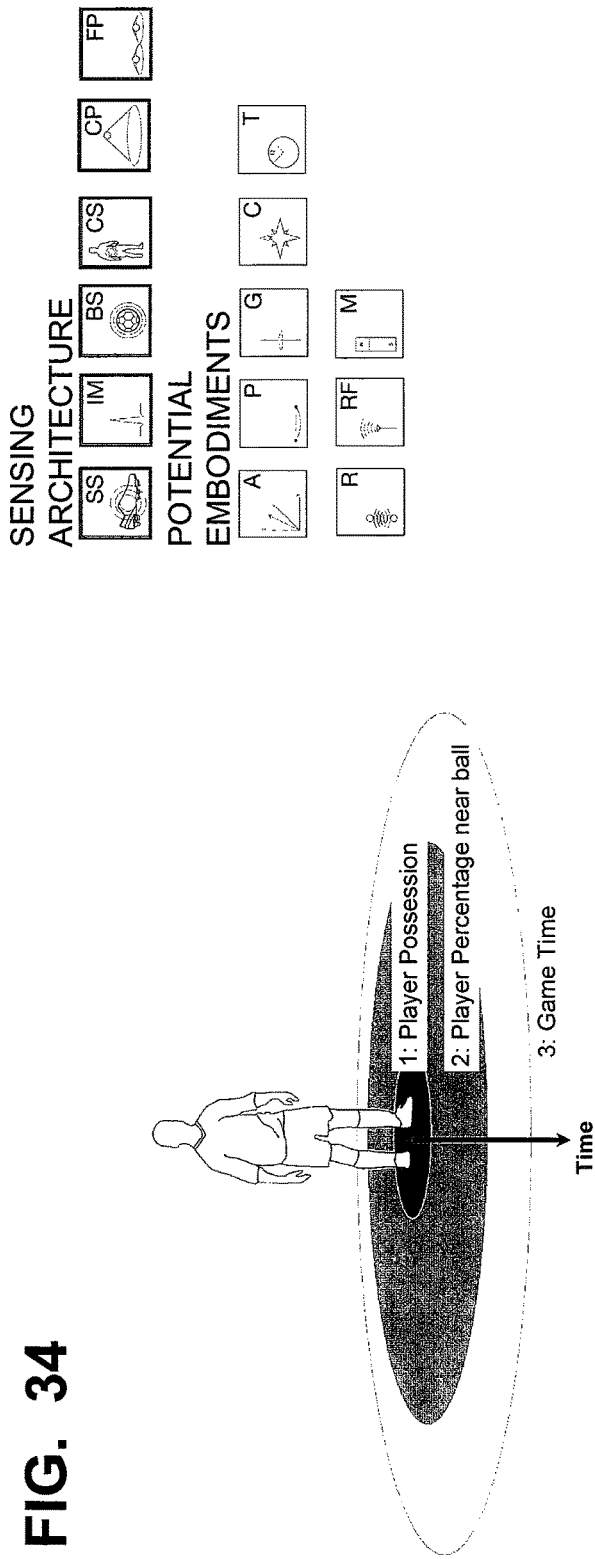

FIG. 34—Possession "Heat Map":

Using the possession and/or player proximity to the ball determination technology described above also can provide useful information for presentation of the data for player or coach review. For example, computer display screens and interfaces in accordance with at least some example of this invention can provide a graphic visualization of the amount of time each player was near the ball and involved in the game. For example, as illustrated in FIG. 34, a first region in immediate vicinity of a visual depiction of the player (e.g., a photo, an avatar, etc.), optionally having a first color or a first color intensity, may indicate the amount of time the player had possession of the ball; a second region surrounding the first region (optionally having a second color or a lighter color intensity from that described above) may indicate the amount of time that the player was in proximity to the ball whether or not in possession (e.g., contested time, defending time, etc.); and, optionally, a third region surrounding the first and second regions that indicates the entire game time or the entire time that the specifically identified player was on the pitch and in the game. Such data presentation can provide a quick visual indicator (optionally coupled with other data on the display, such as total play time, percentages, etc.) for the player or coach as to a specific player's involvement in the game.

Figure 35:
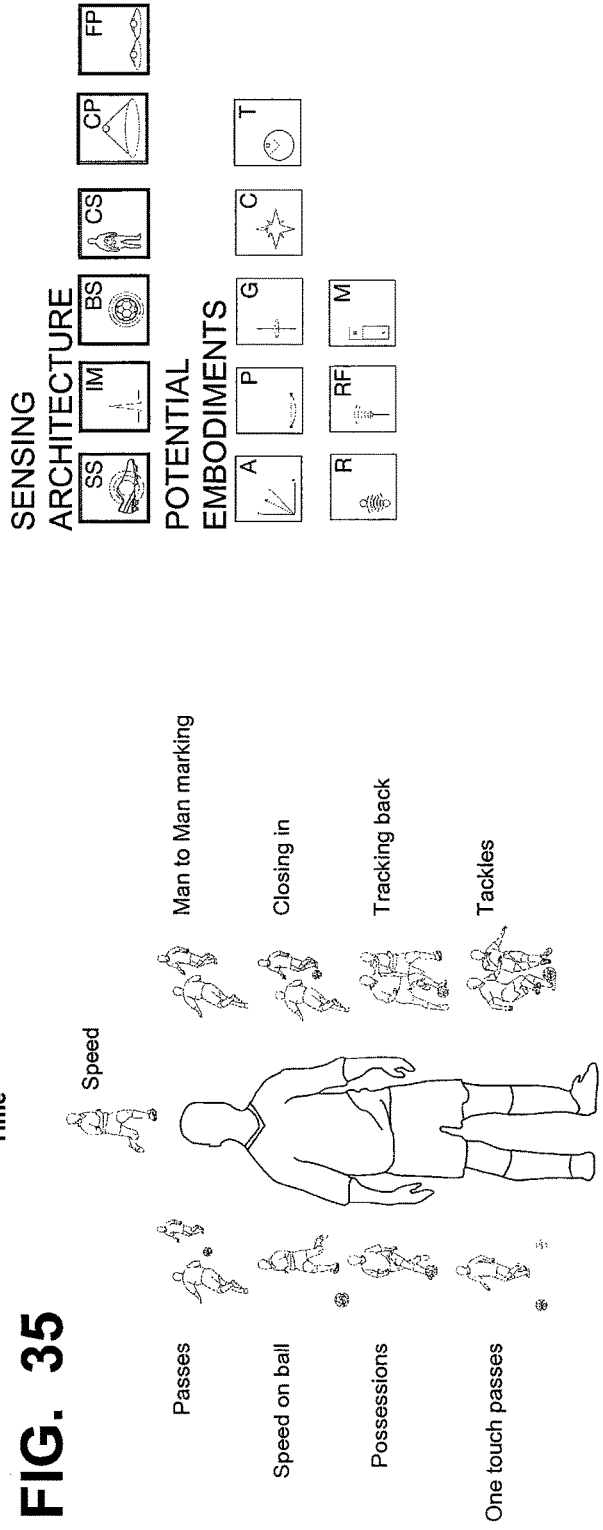

FIG. 35—Intensity:

An intensity metric can be created, for example, using one or more of the sensing systems described above (e.g., player to ball proximity sensing, player to player proximity sensing, player speed, passes, tackles, etc.). As some more specific examples, an intensity metric may include information such as involvement in a play (e.g., ball proximity information (number of times close to the ball, number of times in possession of the ball, etc.), number of passes (including one touch passes), etc.), player proximity information (number of times close to another player, number of successful tackles, etc.), speed of the player on ball, speed of the player off ball, time spent near opposition players that are on ball, man-to-man marking, closing in on the ball, tracking back, etc. This information also can be displayed on a computer display device and/or a user interface therefore, in any desired manner, e.g., as shown in FIG. 35.

FIGS. 36 through 45 illustrate various potential features for detecting and/or measuring various metrics relating to soccer players' kicking actions, e.g., during a game, practice session, etc. The features of these "kick" feature determination systems, methods, and metrics will be described in more detail below.

Figure 36:
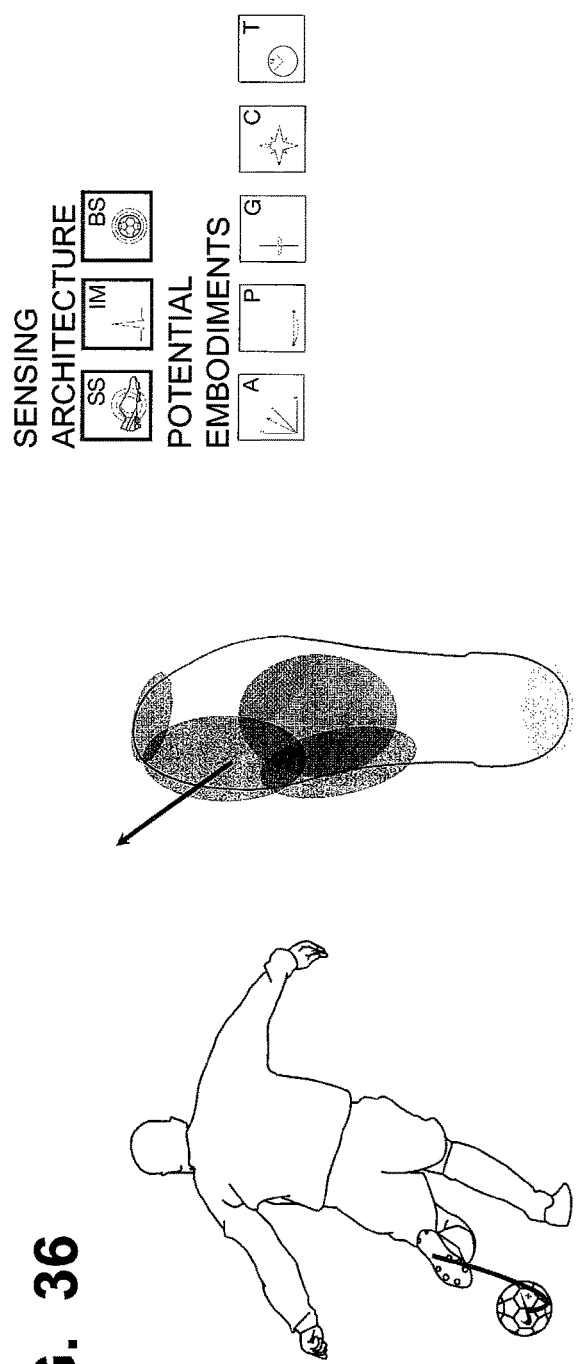

FIG. 36—Kick Zone Determinations:

At least some systems and methods according to examples of this invention will be able to determine the area of the boot and/or foot that impacts the ball during a kick. Such systems and methods may use, for example, an impact vector reporting sensor system (such as a 3-axis accelerometer) in the boot, combined with sensing mechanisms in the ball that can communicate the exact times of impacts. The acceleration vector produced by the impact of the boot with the ball is matched up to the exact time in which the ball is impacted. Because the soccer ball is approximately spherical, the impact vector as reported by the boot will be normal to the surface of the boot that impacted the ball. Therefore a distribution of kick zones on the surface of the boot can be output to the user to help inform skill level and areas of development.

This kick zone distribution information may be displayed on computer displays and/or user interfaces in accordance with at least some examples of this invention, for example, as shown in FIG. 36, where the color intensity or color area corresponds to the number of kicks produced in that area of the shoe (e.g., 1-5 kicks in a zone makes the zone appear red, 6-10 kicks in a zone makes the zone appear blue, etc.). Any number of zones may be provided in the display or a point for each individual kick may be provided in the display without departing from this invention (optionally with the ability for the user to "drill down" to get more data about the individual kick, such as ball speed, travel distance, kick results (e.g., successful pass, goal, turnover, out of bounds, etc.), and the like).

As an alternative, a rotational sensing system may be provided at or near the center of the shoe, and this sensing system can be used to determine the immediate rotation of the foot that occurs when the ball is impacted. This information will allow systems and methods according to this example of the invention to determine if the ball impact occurs ahead or behind the center of rotation axis of the sensor, as well as the side of the foot that impacts the ball.

Figure 37:
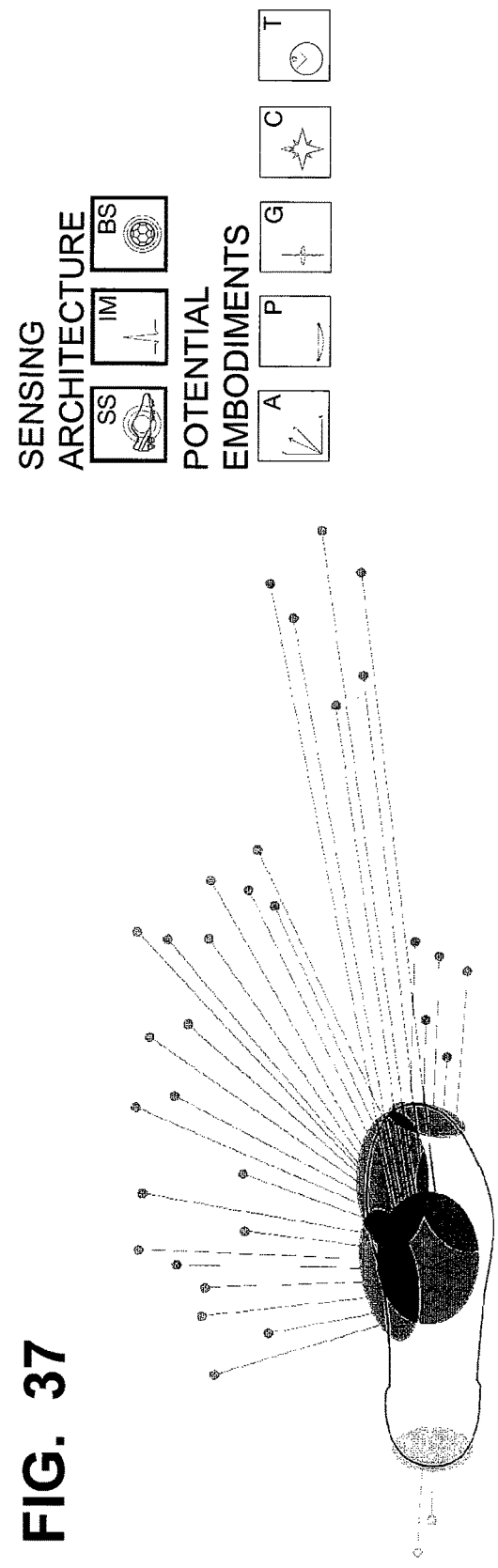

FIG. 37—Ball Flight Path Distribution:

As another potential feature, systems and methods according to at least some examples of this invention will allow for determination of a ball flight path distribution. In this example system and method, the output of a three-dimensional accelerometer in the ball is used in combination with the kick zone determination features described above. As a more specific example, if the acceleration vector from the ball is known (and therefore, the flight direction can be determined), this information combined with the impact location on the boot, allows the flight path of the ball to be determined. This information can then be fed into a system that aggregates the distribution of these flight paths, and the information can be displayed on computer displays and/or user interfaces in accordance with at least some examples of this invention, for example, as shown in FIG. 37, wherein the flight direction off the boot from one or more kicks over the course of a game or other time period can be displayed. The length of the lines shown in the display of FIG. 37 may correlate to the length of the flight path of the ball (optionally with more data available for each individual kick, if desired, e.g., as described above). This information can be used by players and/or their coaches to determine appropriate drills or training sessions to help the player develop specific skills or improve his play and/or versatility. As shown in FIG. 37, the ball flight path information may be combined with the kick zone information in the display.

As some alternatives, a compass, gyro, or other rotational sensor can be added to the system to more accurately determine flight path. Faster rotations of the ball may be considered as producing a more curved flight path due to the aerodynamics of the ball. In such systems and methods, the ball flight path on the display of FIG. 37 may be displayed as a curved path with the degree of the curve displayed correlating to the amount of spin and direction of spin applied to the ball during the kick.

FIG. 38—Longest in-Game Kick:

As another metric, systems and methods in accordance with at least some examples of this invention may determine the longest ball kick by an individual player over the course of a game. As a more specific example, systems and methods according to at least some examples of this invention may use ball speed information (e.g., using known and commercially available technology, such as systems and methods available from CAIROS). Furthermore, this example system and method will collect data using in-ball sensing capabilities (e.g., including, but not limited to: pressure sensors, accelerometers, or gyros) to determine the first impact that occurs after the ball is kicked. Data relating to the kick speed combined with flight time data is then multiplied to get a "longest kick" metric. Additionally, if desired, ball travel directional vector information (e.g., from in-ball sensing systems), such as kick elevational angle as discussed below, can be used to provide an initial ball flight direction vector to provide further directional and distance information. Those skilled in the art can add modifiers to the product of kick speed and flight time (e.g., rotational information) that take into account aerodynamic or other flight effects which may reduce the total flight distance.

FIG. 39—Kick Elevation Angle:

Kick elevation angle may be an important metric in the game of soccer, particularly when it comes to game events, such as free kicks and penalty kicks. For example, on a penalty kick, a ball flight having too high of an elevational angle combined with high speed will never be capable of scoring a goal (e.g., if the ball sails over the level of the net). Systems and methods according to at least some examples of this invention may determine the kick elevation angle by using one of multiple methods of determining the gravity vector (e.g., such as an accelerometer), and then combining it with kick vector data as reported by an inertial sensing system within the soccer ball. The elevation angle of the kick with respect to gravity then may be determined and reported by the ball to a remote system (or stored for later download or use).

Figure 40:
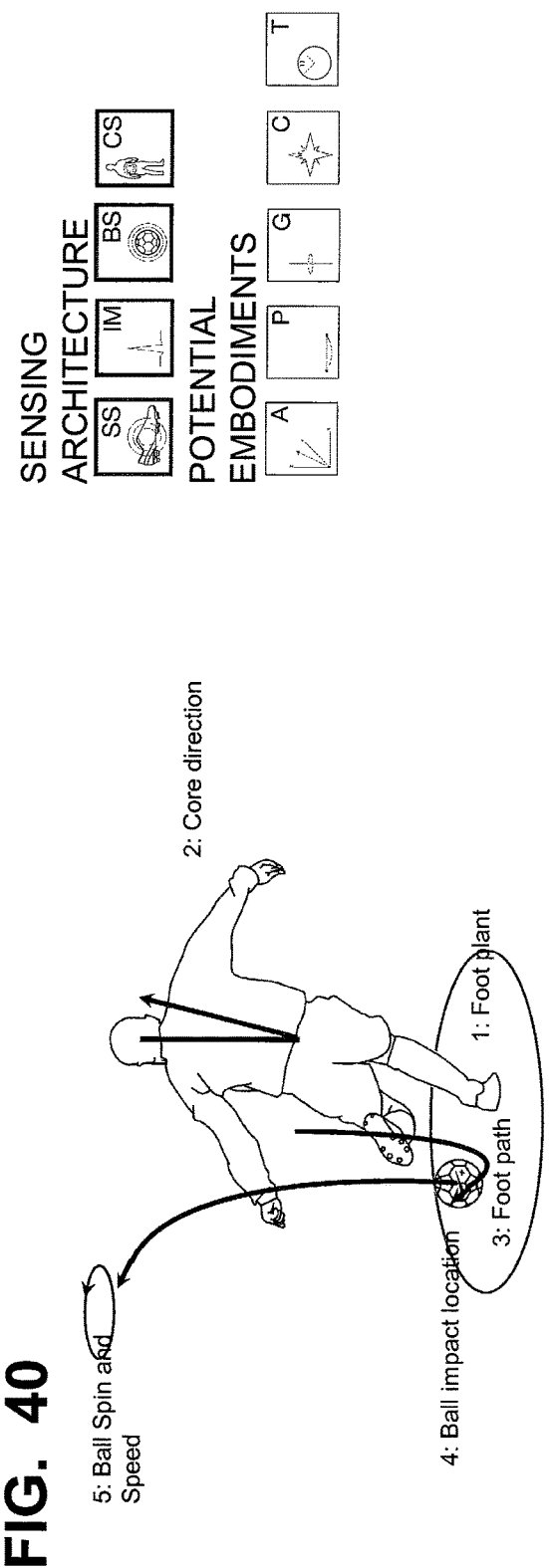
Figure 41:
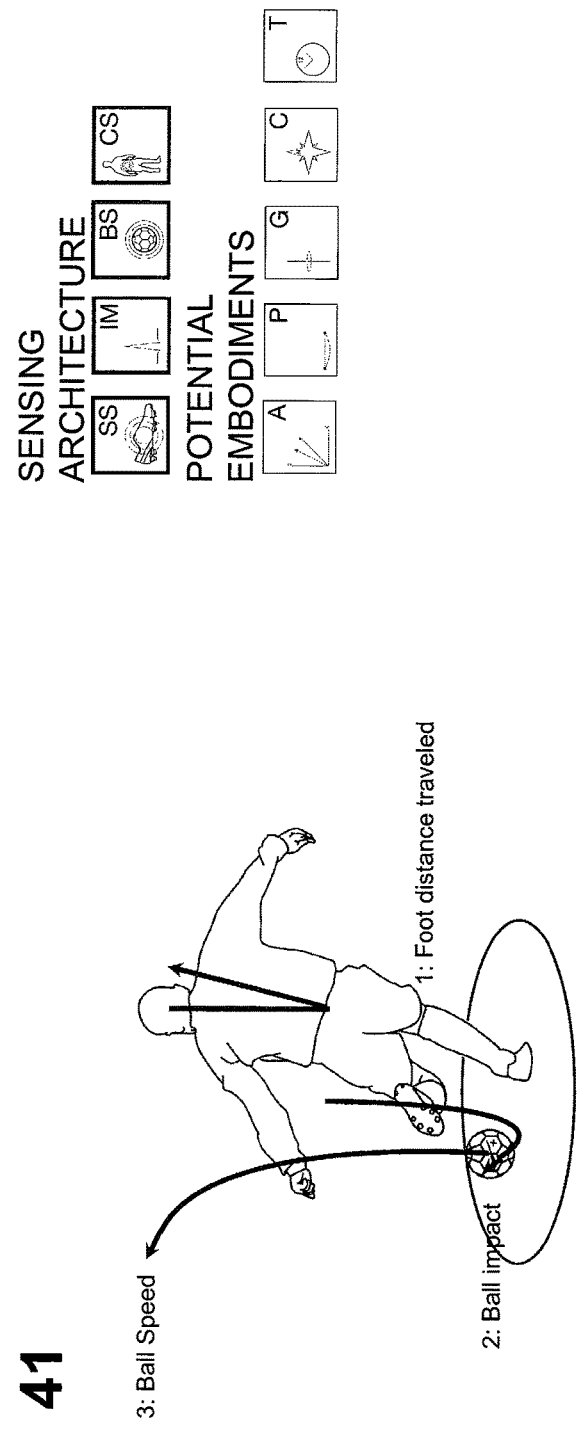

FIG. 40—Kick-Type Distribution:

Systems and methods according to at least some examples of this invention further may determine the various types of kicks and a kick type distribution for individual players (and/or for a team, a specific lineup or combination of players, etc.). Such systems and methods may include use of an impact sensing system inside the ball (e.g., accelerometer, pressure sensor, etc.) which may be matched to an inertial sensing system inside the boot to time-match impacts, which allows determination of when the ball is struck by a specific foot. The boot further may include sensors that allow determination of the path that the foot has traveled over the course of the kick (e.g., gyro, accelerometer, etc.). A proximity sensing system also may be employed (e.g., magnetic sensing, RSSI, etc.) to allow determination of when the ball is in proximity to the players on the field. A core-mounted player rotational sensor also may be employed (e.g., compass sensor, gyro, etc.) to understand which direction the player is facing as well as relative rotational information, and an inertial sensing system on the player can be used to provide additional data. Detection or determination of kick-type distribution information may be accomplished, for example, in the following way:

a. Inertial sensors in the shoe detect the plant foot's impact to the ground and static nature.
b. Core mounted rotational sensor wirelessly communicates the core facing direction (e.g., to a remote location), or this data is stored.
c. Inertial sensors in the kicking foot detect the path/arc that the foot goes through during the kick.
d. The boot impact location is detected, e.g., using the systems and/or methods described above.
e. The ball spin rate and velocity are then recorded and/or broadcast by the ball via wireless communication (or this data is stored).
f. All reported information is compiled to understand the total kick type, and all kicks are then aggregated to create a histogram (or similar graphical or tabular data or information) showing the number of specific kick types (e.g., a left-to-right curving kick, a straight kick, a right-to-left curving kick, the degree of curvature, high trajectory kicks, low trajectory kicks, kick speed, kick distance, etc.).

This data may be used to produce a graphical display illustrating the projected ball trajectory and/or distribution of kick types on a computer display.

As another alternative, if desired, this kick type distribution information may be combined with player-to-ball proximity sensing systems and methods described above to determine when a kicked ball reaches a teammate. This data can be used to produce various pass metrics, such as a pass distribution metric (e.g., number of passes to various teammates, types of passes to teammates, etc.).

FIG. 41—Leg Power:

Systems and methods according to this example aspect of the invention use sensing systems to correlate ball speed and/or other ball flight characteristics to the path traveled by the foot before striking the ball. By determining the amount of "backswing" of the foot, it can be determined how much power the athlete is able to put into the ball given a specific backswing.

As some more specific examples of making this leg power determination, an impact sensing system inside the ball (e.g., accelerometer, pressure sensor, etc.) is matched to an inertial sensing system inside the boot to time-match impacts to enable determination of when the ball is struck by a specific foot, as well as to sense the path that the foot has traveled. A "leg power" metric may be determined in the following way:

a. An inertial sensing system inside the boot detects the distance/amount of travel the foot moves in the backward direction. Optionally, the inertial sensing system can detect when the moment the foot stops during the backswing and begins to move forward and then detects the amount of forward movement the foot travels before striking the ball.
b. At the time of impact, the ball and shoe sensors simultaneously record an impact, and that information is shared via wireless communication (or stored).
c. Pressure and accelerometers inside the ball report the speed of the ball immediately after the kick. Optionally an inertial sensor inside the ball could record speed.
d. Ball speed and foot travel path can then be correlated to determine how far the boot traveled before striking the ball.
e. Leg power is inversely proportional to the amount of distance the foot covered before the ball was struck, and is directly proportional to the speed of the ball immediately after impact. As another option, the peak pressure inside the ball can be used instead of the true ball speed, as the peak pressure will correlate to ball speed. As another option, the magnitude of acceleration of the ball immediately after kick may be used as opposed to the ball speed because these values will correlate to one another as well.

The leg power metric can provide useful data for a player or coach, e.g., to identify stronger players, to identify areas of individuals needing work or training, to compare one leg's capabilities and use against the other leg, etc.

Figure 42:
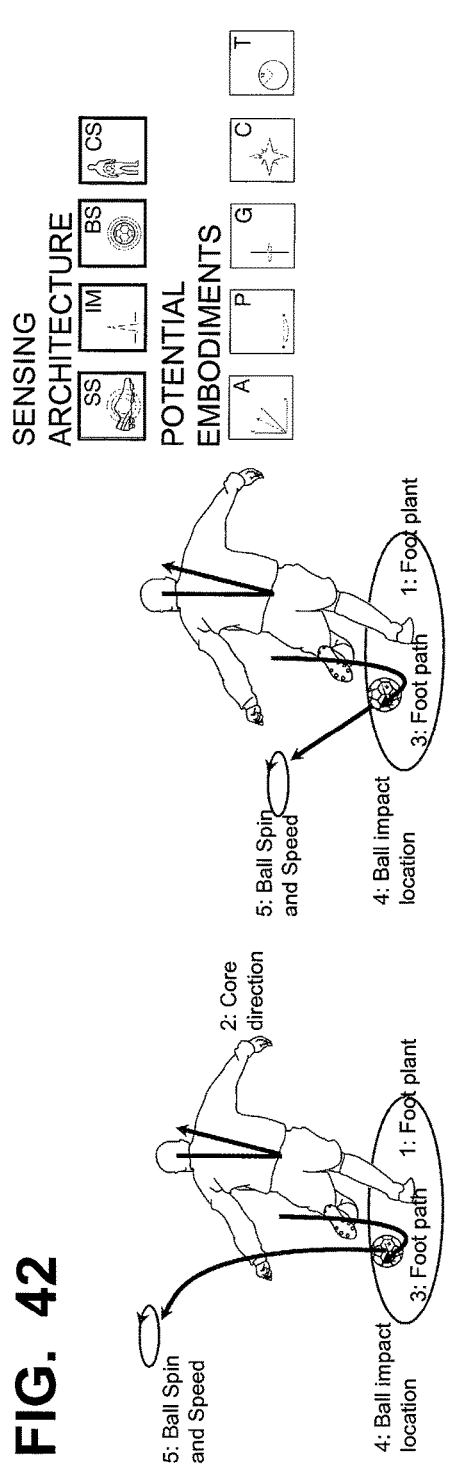

FIG. 42—Kick/Pass Style:

This example aspect of the invention provides a sensing system that can determine the type of kick that was made on a soccer ball. As one more specific example, this example aspect of the invention allows the system to differentiate between a lofted ball flight v. a ball flight that is closer to or along the ground.

Output from an impact sensing system inside the ball (e.g., accelerometer, pressure sensor, etc.) is matched to a rotational sensing system also provided with the ball (e.g., a compass sensor, gyro, etc.), and a lofted kick may be differentiated from an on-the-ground (or closer to the ground) kick, for example, by the following steps:

1. The impact sensing system in the ball senses an impact simultaneously to sensing of an impact by the inertial sensing system in the boot, thereby identifying that the ball has been kicked.
2. Inertial and rotational sensors in the ball then sense whether the ball is in free flight, e.g., defined by the rate at which the ball is slowing down and/or losing altitude. Additionally, rotational sensors sense a consistent rate of rotation (or a relatively consistent rate of rotation) indicating the ball is in the air.
3. If inertial and/or rotational sensors sense a dramatic reduction in speed due to friction or interaction with the ground, or a rapidly changing rate of rotation the ball, these features can indicate that the ball is rolling on the ground.

Different kick types may be advantageous at different times and/or under different circumstances in the game. This metric can allow determination of these different kick types, which also allows determination of the player's effectiveness at using these different kick types (e.g., by determining which kick types or the percentage of specific kick types that resulted in a successful pass to a teammate or that scored a successful goal, etc.).

Figure 43:
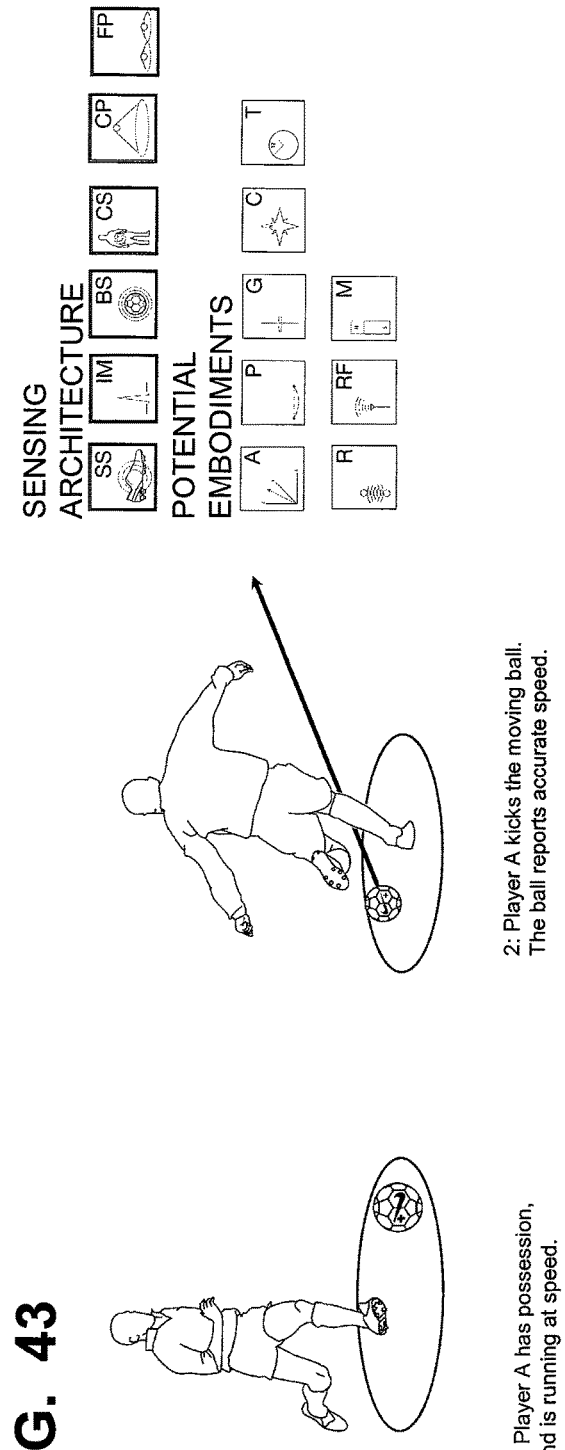

FIG. 43—Kick Power at Speed:

Determination of this metric may use various data and metrics described above in this application. For example, using an on-body or in-shoe sensing system (such as a three-dimensional accelerometer or a piezoelectric sensor element) to determine player speed, as well as proximity/possession technology described above, systems and methods according to at least some examples of this invention further may determine the ability of a player to put significant impact force into kicking the ball while running at speed (a "kick power at speed" metric). The ball sensor(s) and the body-worn sensor(s) communicate their respective status, and this data then may be recorded on either of the two devices (or transmitted to an external device) for future visualization. This metric can be used as a skill metric to determine how much ball control a player has while at their top speed. As some more specific examples, any kick made while travelling at 75% of the player's top recorded running speed or higher (e.g., that particular game's top running speed, or an overall top running speed in all of the player's collected data), optionally traveling at 75% of the player's top recorded "on-ball" running speed or higher, may be a candidate for determining the kick power "at speed" metric so that high kick powers generated at relatively low speeds are not considered for inclusion in this metric.

If desired, this information may be displayed or visualized on a web page or hand-held device (such as a mobile phone) and compared with other metrics gathered by the system in previous and future games.

As an alternative, some ball speed sensing technology only has the ability to determine a relative change in velocity. For example, if the ball is already moving at 10 m/s and it is kicked such that the ball accelerates to 50 m/s, limitations of this technology force it to report only a 40 m/s data value. In such a situation, the "kick power at speed metric" may be determined using an on-body (or on-shoe) speed measuring system to wirelessly communicate with the ball sensor system, which can then modify the reported ball speed value based on the speed of the player, thereby turning the measured value from a relative metric into an absolute ball speed metric, which may have been determined to be "on-ball speed" using technology described above.

Figure 44:
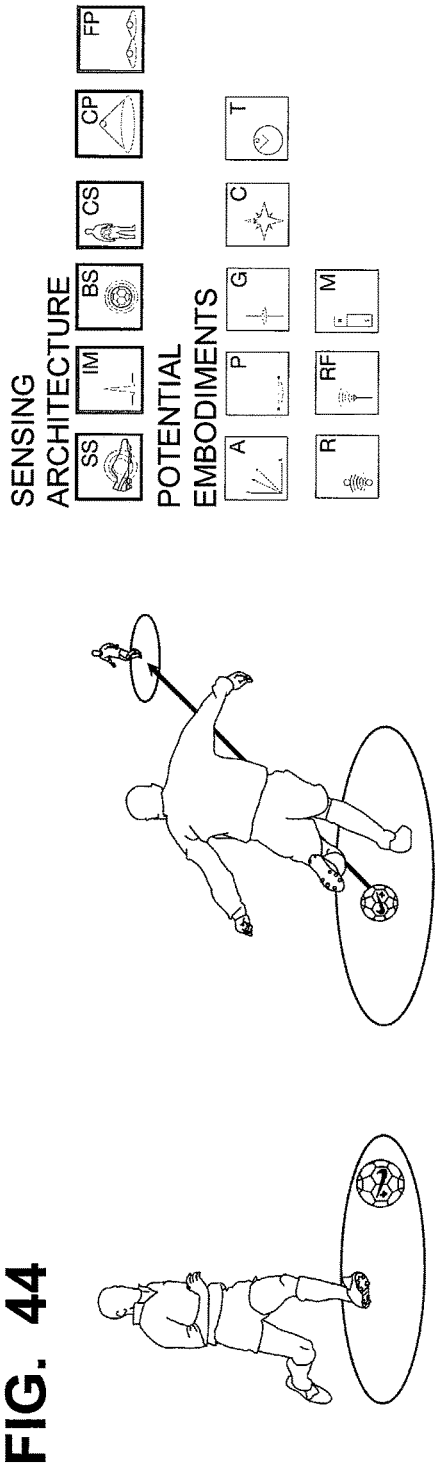
Figure 45:
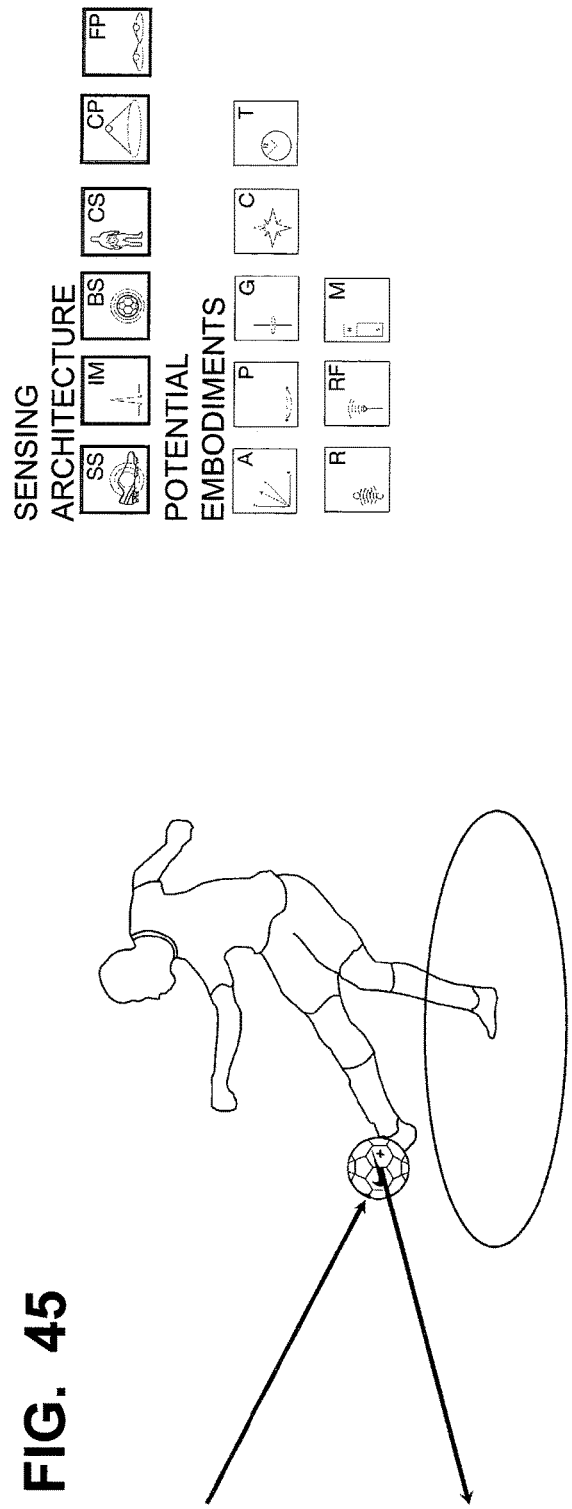

FIG. 44—Pass Accuracy at Speed:

This example aspect of systems and methods according to the invention measures the metric of pass accuracy (e.g., successful passes to teammates) with the additional passing player's speed associated with it. Using an on-body or in-shoe sensing system (such as a three-dimensional accelerometer or a piezoelectric element) to determine player speed, as well as player-to-ball proximity/possession technology described above, systems and methods according to at least some examples of this invention can measure the ability of a player to accurately pass to a teammate while moving at higher running speeds speed. More specific examples of measuring this metric follow.

Via wireless communication methods, the ball sensor and body-worn sensors communicate their respective status (e.g., player making the kick, the player receiving possession after the kick, the speed of the player making the kick, etc.) which is then recorded on either of the two devices (or transmitted to an external device) for future visualization and review. This metric can be used as a skill metric to determine how much ball control a player has while running at or near their top speed (e.g., while travelling at 75% of the player's top recorded running speed or higher (e.g., that particular game's top running speed, or an overall top running speed in all of the player's collected data), optionally while traveling at 75% of the player's top recorded "on-ball" running speed or higher, etc.).

If desired, this information may be displayed or visualized on a web page or hand-held device (such as a mobile phone) and compared with other metrics gathered by the system in previous and future games.

FIG. 45—Volley:

This example aspect of the invention measures information regarding volleys. For determining this information, systems and methods according to at least some examples of this invention use inertial and/or pressure sensing systems within the ball to determine ball speed. Wireless communication capabilities also may be provided within the ball to broadcast the ball speed information, as well as an exact time of impact (alternatively, this data may be simply stored). Additionally, inertial sensing systems may be provided as part of boot of the players, such as an accelerometer, a piezoelectric element, or other device. In such systems and methods, a volley can be determined by detecting coincident impacts to the boot and ball of one player, with then an "in-air" signature signal from the in-ball accelerometer. If the next impact registered by the ball is coincident with an impact to another player's boot, this then signifies a volley where the ball never touched the ground in-between the initial kicker's boot and the receiver's boot. In such a situation, the receiver may be credited with a "volley". Volleys are an important metric because they indicate an ability to keep the ball moving in a rapid manner (which may help avoid defenses, particularly when the volley is coupled with a successful pass to a teammate, a scored goal, or other favorable event, which also can be detected by systems and methods in accordance with at least some examples of this invention).

FIGS. 46 through 50 illustrate various potential features for detecting and/or measuring various metrics relating to actions involved in sending the ball into play after a stoppage of play, such as an out of bounds event, etc. The features of these "set piece" feature determination systems, methods, and metrics will be described in more detail below.

Figure 46:
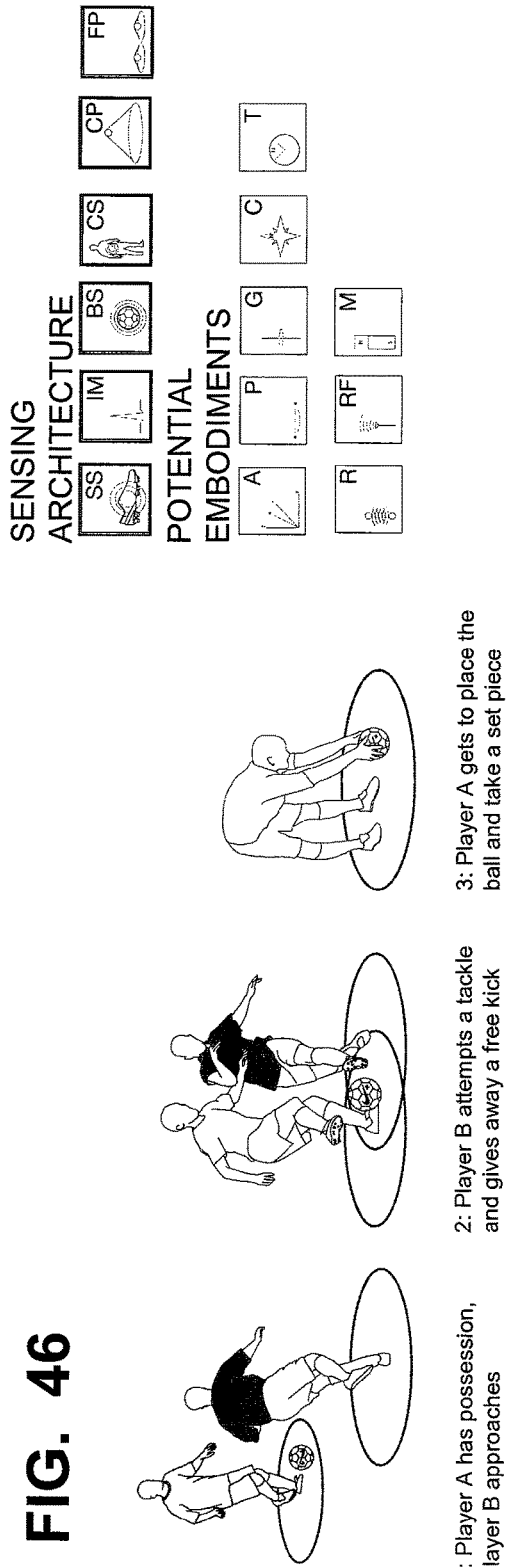

FIG. 46—Free Kick Awarded:

Systems and methods according to at least some examples of this invention may determine when a free kick has been awarded. The free kick can be determined based on the combined technologies explained above for possession and tackle determination, as well as the technology described in more detail below for determining whether a set piece exists. More particularly, a free kick can be determined by the following steps:

a. Possession of the ball is determined and awarded to a first player.
b. A second player comes into the area of the first player in possession of the ball (e.g., as determined by an attempted tackle, contested time, player-to-ball proximity, player-to-player proximity, etc.). This feature also may be determined, for example, based on person-to-person proximity and touching of the two people (e.g., as indicated by impact sensors provided on the players' bodies).
c. The ball detects a "set piece" play, as will be described in more detail below in conjunction with FIG. 48.

The "free kick" awarded metric may be a useful measure of the effectiveness of a defensive player or other information.

Figure 47:
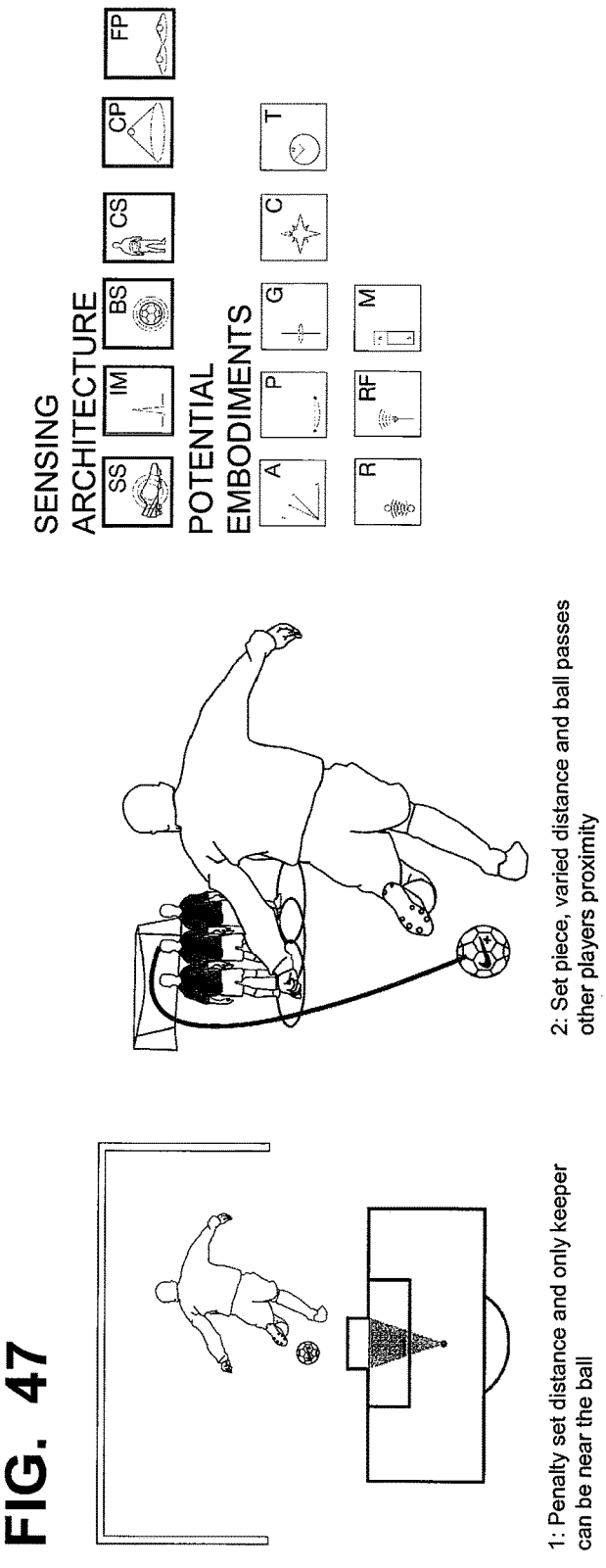

FIG. 47—Free Kick v. Penalty Kick:

Systems and methods for determining approximate flight distance of the ball are described above. Additionally, systems and methods for determining when the ball has been caught by the goalkeeper are described in more detail below. These features will be useful in automatically distinguishing a free kick from a penalty kick by systems and methods in accordance with examples of this invention.

A penalty kick is always kicked from the same spot on the field, where a free kick is not. Using an accelerometer and/or a combination of pressure sensor and an accelerometer, ball speed can be calculated. This example aspect of the invention uses time information from the kick to first impact within proximity of the keeper, combined with set piece knowledge (as described in more detail below) to determine if the kick was a penalty kick using ball distance. For example, if after a set piece determination the ball is kicked and comes into proximity of the goal keeper (or in contact with the goal keeper) within a certain time frame (e.g., depending on the ball speed), then it may be determined that the kick was a penalty kick. If no goal keeper proximity is detected after a set piece determination, or if no goal keeper proximity is detected within a predetermined time (e.g., depending on the ball speed), then it may be determined that a free kick occurred.

As an additional feature or an alternative feature, using a possession or proximity sensing system as described above, the two types of kicks may be differentiated. For example, a penalty kick, by definition, will not have other players (either offensive or defensive) within a very specific distance from the ball (as determine by the penalty box size). During the flight of the ball, a proximity sensing system (as described above) can determine whether the ball passed near any other players on its way to the goal. A free kick will always have defending players between the ball and the goal, and therefore, a shot on goal typically will register at least a brief proximity to a defensive player (at minimum) before reaching the keeper. As yet another example, player-to-player proximity detection may indicate two or more players on a team in tight proximity to each other (e.g., when in a wall position, as shown in FIG. 47), which also may be used as an indication that a free kick has occurred.

Figure 48:
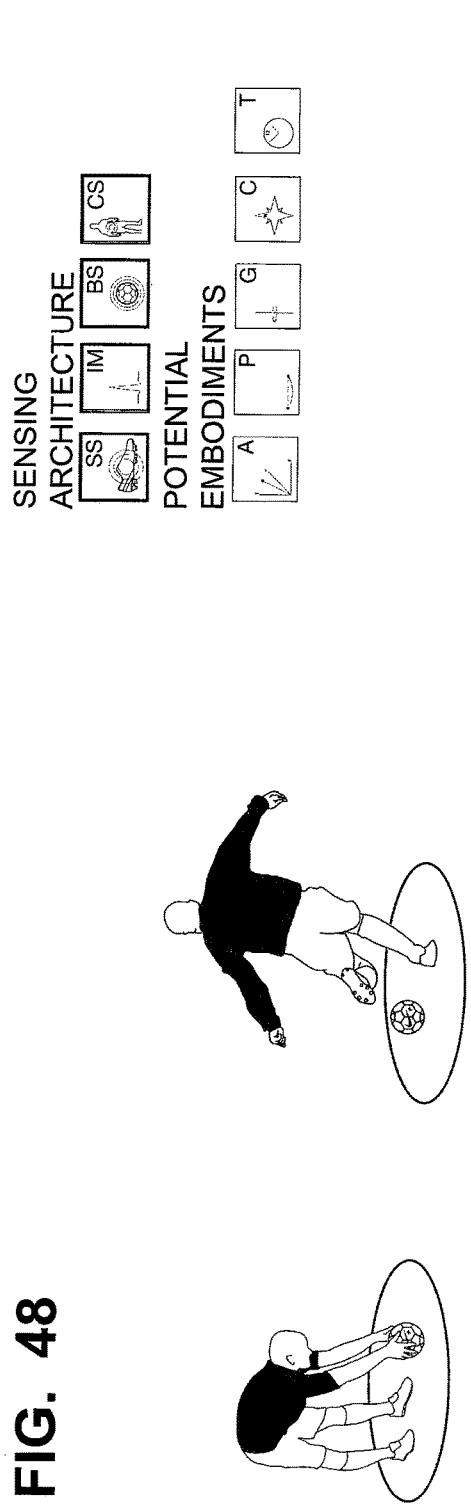

FIG. 48—Set Piece Shot:

"Set piece," as used in this context in this specification, refers to the soccer ball being placed on the ground for an ensuing penalty kick or free kick. It is an important metric for the player to know and distinguish "set piece kicks," as these tend to be the more difficult shots on goal during the game of soccer.

Using an accelerometer or other ball mounted inertial sensing system, it can be determined when a ball is not in motion (or when its motion is slow or minimal). Some more specific examples include, but are not limited to: a three-dimensional accelerometer in the ball, a three-dimension accelerometer combined with a gyroscope, an accelerometer in the ball combined with a compass sensor, ball movement speed and/or lack of rotation matching a player in proximity's speed, etc. One or more of these sensor outputs may be utilized to show the ball has been carried and placed, followed by the ball not moving, and then followed immediately by a kick (matching of boot impact to ball movement/pressure spike). While this kick could be a corner kick, a penalty kick, or a free kick, the type of kick may be determined, at least in some instances, by what happens next, e.g., by who's proximity it passes, by the next contact person, the timing between the kick and the next proximity, etc., e.g., as described above.

Figure 49:
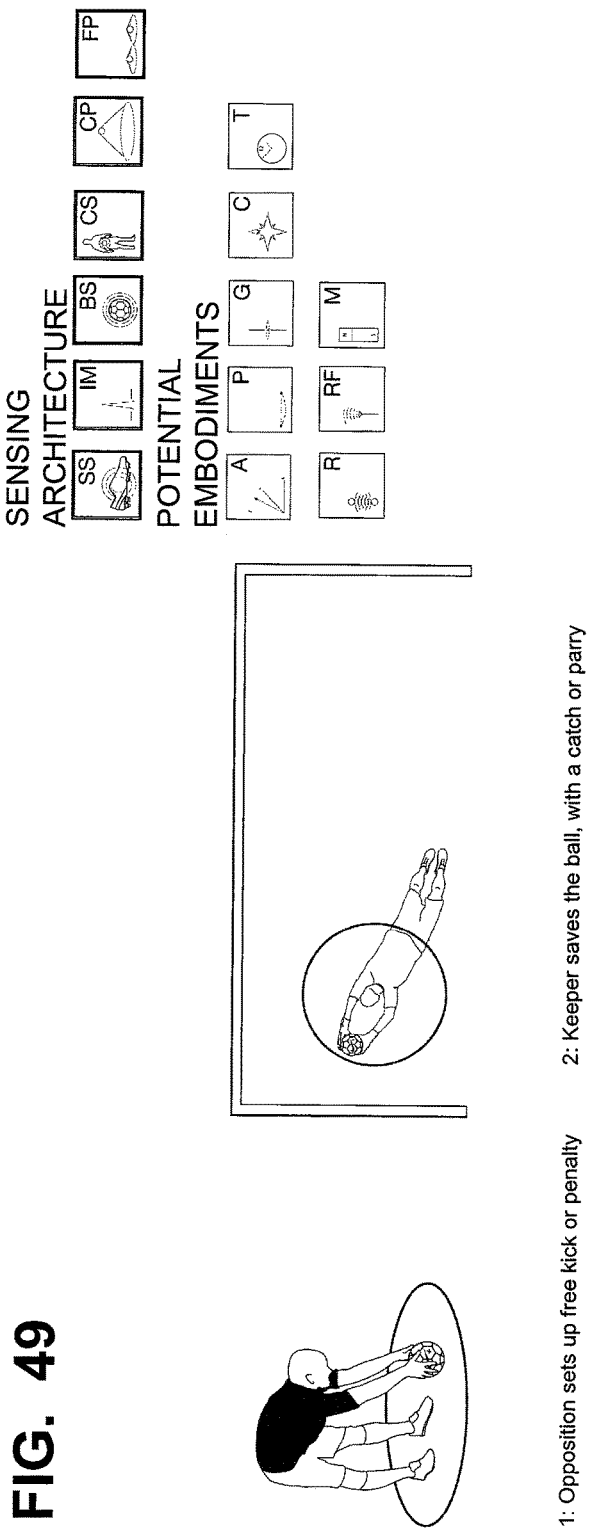

FIG. 49—Set Piece Save:

This example aspect of systems and methods according to this invention determine when a kick after a set piece event (e.g., determined as described above) has resulted in a goal keeper save. As noted above, the term "set piece" refers to the ball being placed on the ground for an ensuing penalty kick or free kick, and it may be determined as described above.

As a more specific example, a set piece event may be determined by systems and methods according to this example aspect of the invention in the manner described above in conjunction with FIG. 48. Once a set piece event has been determined, and when the set piece event has included proximity to the goal keeper, a throw, pass, or drop kick initiated by the goal keeper may be detected (e.g., as described above and/or in more detail below) and used as an indication that the goal keeper successfully saved the kick resulting from the set piece event (e.g., by a goalkeeper catch or parry event). Various features of goal keeper save determinations will be described in more detail below.

FIG. 50—Set Piece Kick—On Goal or Not:

Example systems and methods for determining a set piece event are described above. This example aspect of systems and methods according to the invention uses the previously defined set piece sensing method and adds proximity/possession sensing systems and methods (such as magnetic sensing, radar, etc.), e.g., like those described above, to determine whether a set piece kick was "on-goal" or not. As a more specific example, when a set piece event has been determined, immediately followed by a kick, which is then followed by ball to keeper proximity, if the next event is a kick or a drop kick by the goal keeper, then a set piece save event may be determined.

FIGS. 51 through 55 illustrate various potential features for detecting and/or measuring various metrics relating to player motion, e.g., during a game, practice session, training session, etc. The features of these systems, methods, and metrics will be described in more detail below.

FIG. 51—Direction of Movement Based on Body Angle:

Systems and methods according to at least some examples of this invention will provide information regarding the direction of player movement, which may be based, at least in part, on the player's body angle during the motion. This determination may be made, in at least some example systems and methods according to this invention, using an "on body" accelerometer to sense the upper body's angle and translate this information into a direction metric. For example, when accelerating or moving in any direction (e.g., forward, backward, to the side, etc.), the upper body tends to lean in the direction of acceleration. For example, when accelerating in the forward direction, the body leans forward. This angle and lean helps move the body forward, and the legs follow. Generally, the greater the acceleration, the greater the lean angle. This same feature also works for back steps and side steps.

Accordingly, by measuring the lean of the body, information regarding the player's movement direction (and optionally the intensity of this motion) can be determined. This metric may be useful for determining a player's ability (e.g., if an offensive player spends too much time backpedalling or sidestepping, etc.) and/or ascertaining areas for training and game improvement.

FIG. 52—Player "Turn In":

This example aspect of the invention uses a sensing system on the player that determines player speed, such as an inertial sensing system, contact-time based pedometer system, etc., and a player mounted rotational sensor, such as a gyroscope, compass sensor, etc., to determine the amount of body rotation. Player "turn-in" can be defined as the amount of speed lost by the player during quick direction changes. This metric may be valuable in the game of soccer as a measure of a player's "quickness" or "agility." The acquisition of the "turn-in" metric may simply require the measurement of the speed sensing system before and after a measured rotation from the rotational sensing system. As one more specific example, the performance metric may be calculated by subtracting the player speed before the change in direction from the speed post rotation. Information relating to this metric can then be displayed or visualized on a web page or hand-held device (such as a mobile phone) and compared with other metrics gathered by the system in previous and future games. Moreover, information relating to this metric may be used to develop training programs to improve player quickness/agility.

FIG. 53—Player "Turn In" On Ball:

This example aspect of the invention is similar to the "turn-in" determination as described above, but additionally includes the metric that the player is in possession of and/or in proximity to (and optionally maintains possession of and/or in proximity to) the ball. In other words, for any measured turn-in events, as described above, another metric can be developed for turn-in events that occur for the player while the player is in possession of or in proximity to the ball. This metric may be valuable with respect to the game of soccer as a measure of a player's "quickness" or "agility" while handling the ball or while closely defending the ball. Information relating to this metric can then be displayed or visualized on a web page or hand-held device (such as a mobile phone) and compared with other metrics gathered by the system in previous and future games. Moreover, information relating to this metric may be used to develop training programs to improve player quickness/agility while handling the ball.

Figure 54:
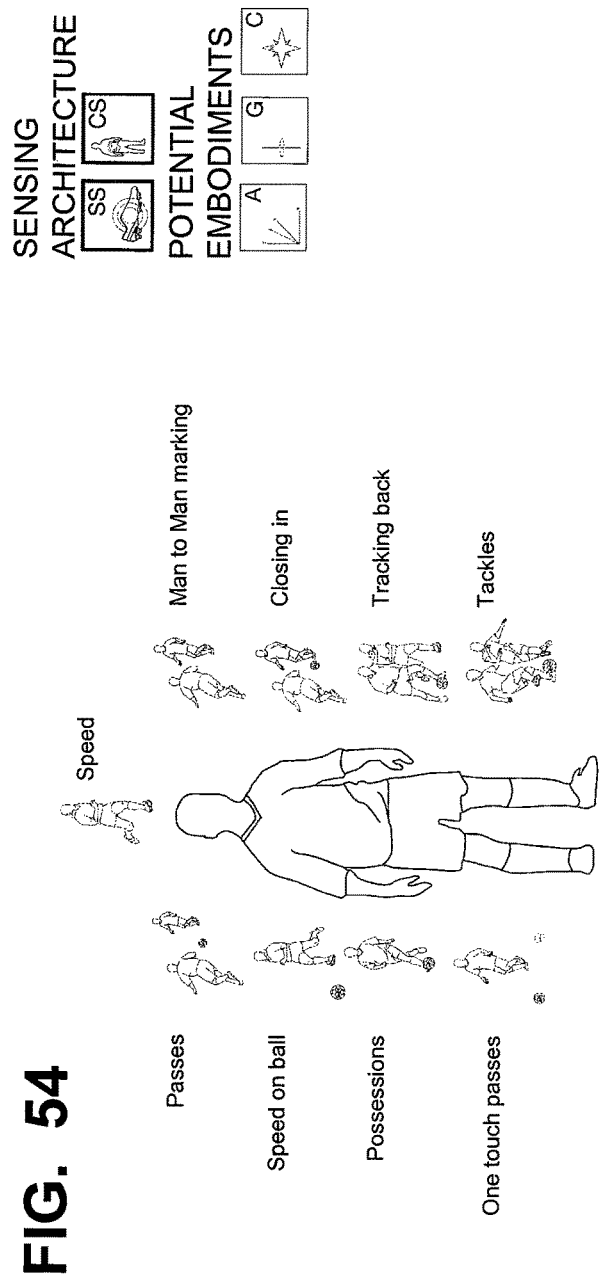

FIG. 54—In Shoe Sensor Based Contextual Reporting:

Athletic performance monitoring systems and methods according to at least some examples of this invention include an in-shoe sensing system for measuring speed and/or distance information (e.g., a pedometer type speed and/or distance sensor). This sensor also may provide contextual information about the specific part of sport the athlete is in, e.g., what types of activities he or she is performing, and this contextual information may be used by other portions of the athletic performance monitoring systems and methods (e.g., on body sensors, etc.) to change the kinematic models and/or algorithms used to determine the player's running speed and/or travel distance.

Output from the shoe based sensors (e.g., accelerometer, force sensors, etc.) may include a "signature" appearance that correlates to the type of activity being performed by the athlete. For example, the in-shoe based accelerometer output (e.g., the signal shape) may differ depending on whether the athlete is moving forward, moving rearward, side stepping, tackling, passing the ball, walking, dribbling, sprinting, slow running, skipping, jumping, sliding, sliding laterally, etc. By automatically determining the type of action with which the athlete is involved (using the shoe based sensor output), more specialized algorithms for determining player performance may be called up to enable a more accurate determination of the parameters involved in the player's performance. Different algorithms also may apply under other differing circumstances, for example, different speed and/or distance determining algorithms may apply depending on whether the player is on ball or off ball.

As one more specific example, because different in-shoe sensor waveforms may be involved in running forward or backward (e.g., different loft times, different pressure profiles, etc.), systems and methods according to examples of this invention may automatically determine whether an athlete is moving forward or rearward based on the characteristics of the sensor output. Because step size also may differ when moving forward as compared to moving backward, different algorithms for ascertaining speed and distance information may be called upon for providing speed and distance data, depending on whether the motion is forward or backward. Accordingly, this aspect of the invention allows for a more accurate determination of speed and/or distance based the determined manner in which the athlete is moving.

Moreover, metrics involving the type of movement or other actions performed by the athlete may be useful for the player or coach, e.g., to indicate whether an offensive player spends too much time backpedalling or sidestepping, to measure player's efforts and intensity, etc.

Figure 55:
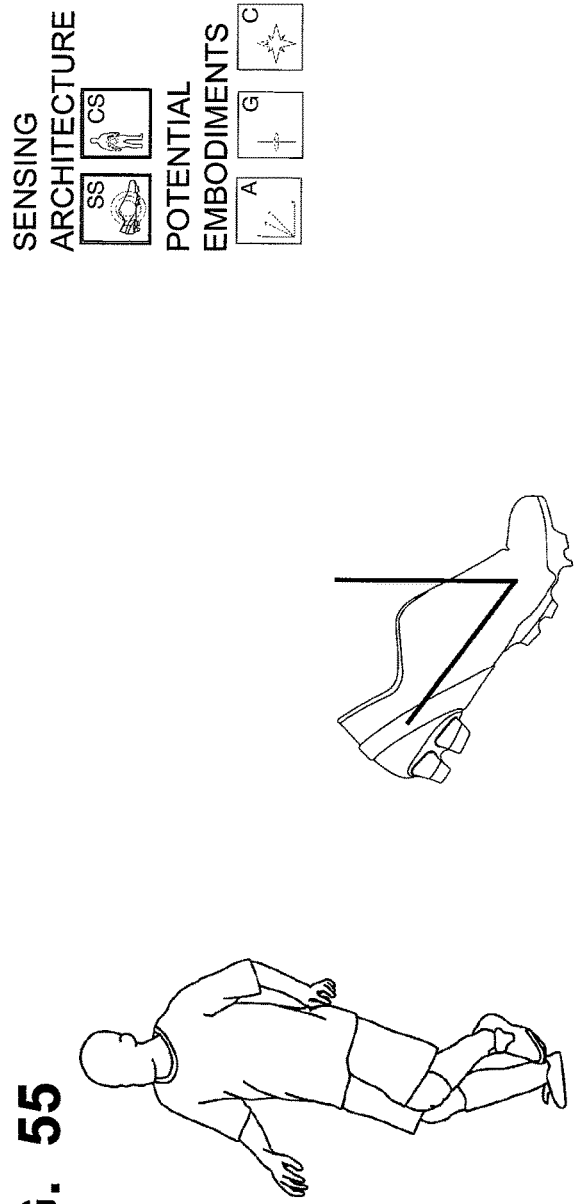

FIG. 55—Time Spent on Toes:

In sports and athletic performances, it is often important for the athlete to stay on his/her toes. Being on one's toes generally enables quicker reactions and/or indicates that the athlete is performing with more intensity (e.g., while sprinting, an athlete spends more time on his/her toes than when jogging or walking). Systems and methods in accordance with at least some examples of this invention may include an in-shoe sensing system that determines the foot angle so as to enable a determination of the amount of time the athlete spends on his or her toes. One more specific example of hardware for making this measurement may include an accelerometer that compares the gravity vector to the orientation of the sensor within the shoe. As another example, the shoe may include a rotational sensing system, such as a gyroscope. The shoe also may contain a measuring system like that described in more detail below in conjunction with FIG. 91. The determined information may be transmitted wirelessly to another system for processing and/or stored. The finally determined metric may include, for example, the total amount time on one's toes, the percentage of time spent on the toes, the percentage of actual movement (or running) time spent on the toes, etc.

FIGS. 56 through 65 illustrate various potential features for detecting and/or measuring various metrics relating to playing the game of soccer, which may be used and evaluated during a game, practice session, training session, etc. The features of these systems, methods, and metrics will be described in more detail below.

FIG. 56—Player Posturing:

"Player posturing" is the determination of the ball movement direction as it relates to the player's core facing direction. Using this information, one can determine if a player is in a defensive posture, in an aggressive or attacking posture, etc. The hardware used for determining this metric, in at least some example systems and methods according to this invention, include: a directional sensing system inside the ball (such as a compass sensor, accelerometer/gyro combination, etc.) to give ball movement direction; and a body-mounted sensor of similar architecture (compass sensor, accelerometer/gyro, etc.) to give player facing direction. The following example steps may be used to determine a "player posturing" metric:

1. Using inertial sensors in the ball, the direction the ball is moving (rolling or in flight) is determined.
2. Using a core-mounted sensor (such as gyro, compass, etc.), the direction the body core is facing is determined.
3. Combine these two pieces of information allows a determination of the relative ball motion to core facing direction, to help understand contextually what is happening between the player and the ball.

Additionally or alternatively, core worn sensors between opposing players can be used separately (or added to the above) to determine the player to player relationships, and therefore enrich the data-set to build more confidence on the posturing. For example, the direction of motion (and/or the facing direction) of the player in possession of the ball can be compared to the direction of motion (and/or the facing direction) of the defensive player to provide additional information relating to this "player posturing" metric.

FIG. 57—Man to Man—Opposing Position:

The determination of what opposing player a particular player had been marking can be a useful piece of information when determining a player's performance metrics. Systems and methods according to at least some examples of this invention will use proximity determination methods as described above, but this technology will be used on each individual player to provide player-to-player proximity data and information.

As one alternate, if desired, peer-to-peer networking technology may be used to determine and track proximity between players (as well as between other elements within systems and methods according to at least some examples of this invention). When two players are close enough to establish a peer-to-peer communication channel (e.g., between devices that they are carrying, such as shoe mounted sensors, body core mounted sensors, etc.), this could be established as a proximity event. By tracking and timing such proximity events, systems and methods in accordance with these examples of the invention will know which nodes of the network (e.g., which other players) a given player was in communication range with during the majority of the game. As players get further away from each other, they may get out of range (and thereby break the peer-to-peer communication channel). Other ways of determining player-to-player distance may be used without departing from this invention. If desired, a "heat map" or other graphic display may be provided to indicate the opposing team players with which any given player most stayed near during the course of the game, and this will allow a determination of the player being defended or marked during the game.

As another alternative, some RF modules have RSSI ("radio signal strength indicators"). RSSI technology can be used on each player to determine which player was closest to another player for the majority of the game.

The Opposing Player metric may be useful, for example, to determine a defensive player's relative performance with respect to the player or players that he was defending (e.g., goal scoring effectiveness, successful passing, successful interceptions, etc.).

Figure 58:
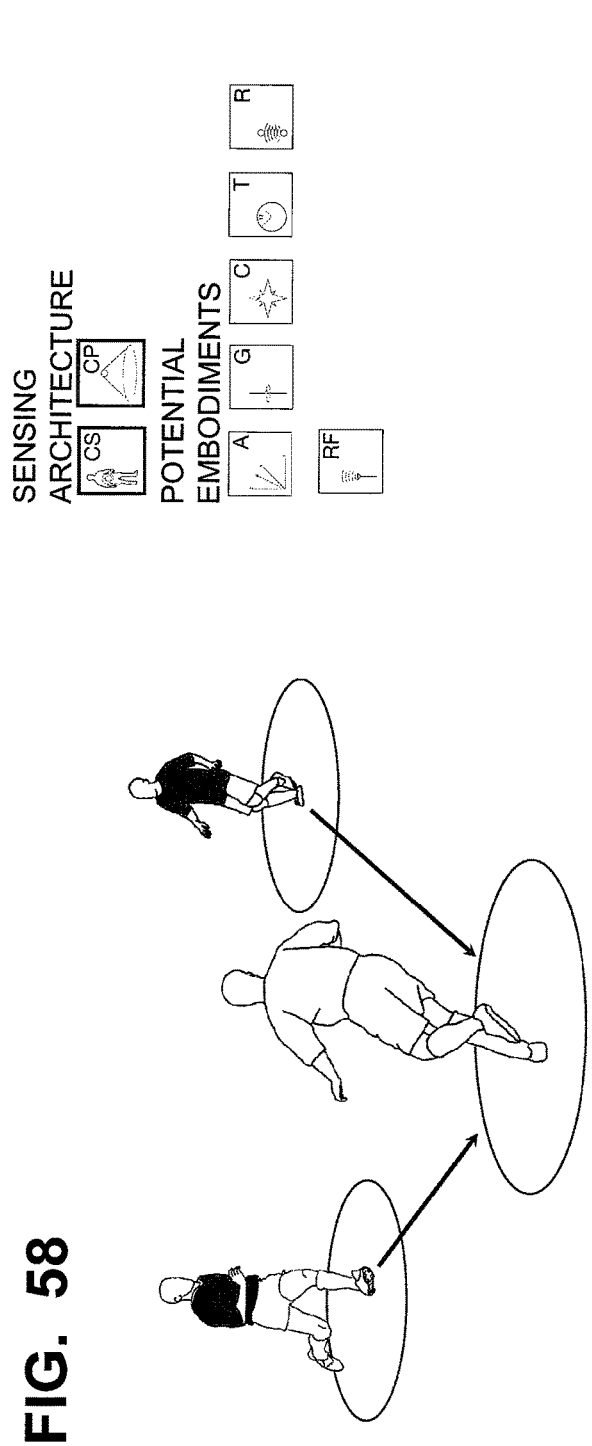

FIG. 58—Drawing Opposition:

The Man to Man Opposing Position detection capability described above can be combined with other metrics to provide additional interesting data and information relating to soccer (or other sports). For example, combining the Man to Man Opposing Position detecting capability with player-to-player proximity detection and player speed determination (e.g., in boot inertial sensors, as described above) may be combined to provide a metric relating to the ability of a player to draw the opposition. Using an inertial based sensing system, sprints or bursts of speed can be measured and combined with the player-to-player proximity to determine if a player is drawing opposition. Example systems and methods according to this aspect of the invention follow.

First, proximity sensing systems and methods as described above can determine when two players are near each other. If one player sprints away and the proximity detection system shows no players near him and shortly thereafter an opposition player is detected by a proximity sensor again, this suggests that the initial player (the one that initially sprinted away) has pulled the opposition players with him. Ball possession determinations also may be used in such systems and methods (e.g., to determine the player's ability to pull opposition even without the ball).

Additionally, if desired, skill metrics can be created based on the amount of time a player spends within proximity of the opposing player. If a player is meant to be in an offensive position (striker), the more time spent away from an opposing player the better. On the other hand, a defensive player could be considered better the more time he/she spends in proximity to the opposition.

Figure 59:
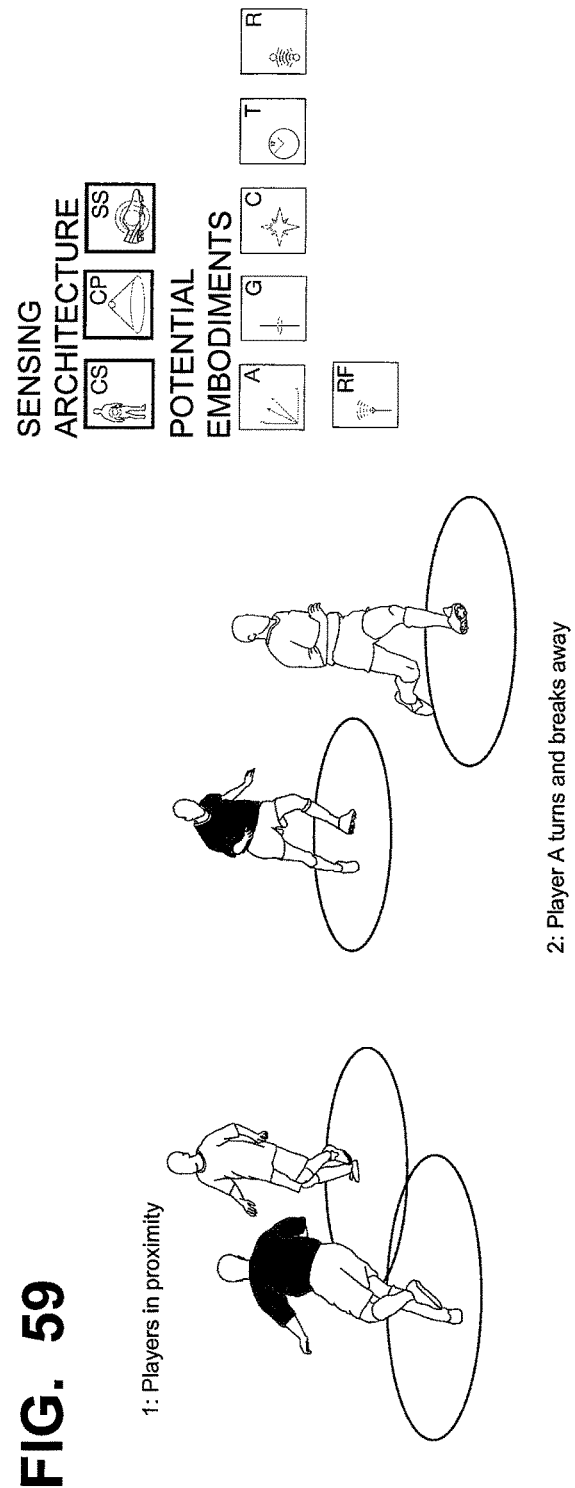

FIG. 59—Breakaway Speed:

The Man to Man Opposing Position detection capabilities as described above open the door to yet determination of additional information and metrics. As another more specific example, an inertial sensing system can be placed on the cores or boots of the athletes and a comparison can be made between the relative accelerations of each player at the same time. Such a system may be used to determine a "breakaway speed" metric.

An example system and method according to this invention for determining breakaway speed comprises a speed detection system and combines this information with a wireless communication system to determine coincident accelerations of two players. The relative speeds of the two players can be determined (optionally coupled with directional information), and this information then can be used to produce a performance metric, e.g., determining whether the player was faster than the player defending him/her (e.g., were you faster than the player that was marking you, etc.).

FIG. 60—Successful Pass:

Completion of a successful pass is incredibly important in the game of soccer (and other sports). The following describes an example system and method for determining when a successful pass event has occurred (e.g., a "successful pass" means a pass from one teammate to another).

In this example system and method, output from an impact sensing system inside the ball (accelerometer, pressure sensor, etc.) is time matched to output from an impact sensing system inside the boot to enable determination of when the ball is struck by a specific foot. A ball proximity sensing system is also employed (magnetic sensing, RSSI, etc.) to enable determination of when the ball is in proximity to a player. A successful pass is determined by systems and methods according to this example of the invention in the following steps:

a. Ball possession by a specific player is determined, e.g., as described above.
  b. Kick impacts are registered both on the in-shoe sensor and the in-ball sensor.
  c. The ball leaves the proximity of the player that kicked it.
  d. The ball enters the proximity of a teammate, as determined by the proximity sensing system.
  e. Impacts are measured simultaneously by the teammate's boot and the ball, and a successful pass is recorded.

Determination of the number of successful passes and the number of unsuccessful passes are useful metrics for evaluating the performance of the player.

FIG. 61—Give and Go:

The "give-and-go" is another common play in the game of soccer. The following describes one example sensing system, method, and logic that may be used to interpret the various sensor signals for determining when a "give-and-go" event has occurred.

Output from an impact sensing system inside the ball (accelerometer, pressure sensor, etc.) is time matched to output from an impact sensing system inside the foot to enable determination of when the ball is struck by a specific foot. A ball proximity sensing system is also employed (magnetic sensing, RSSI, etc.) to enable determination of when the ball is in proximity to the player. A give-and-go event may be determined in the following manner:

a. First, ball possession by Player A is determined, e.g., as described above.
  b. A kick by Player A is registered on Player A's in-shoe sensor and the in-ball sensor.
  c. The ball leaves the proximity of Player A.
  d. The ball enters the proximity of a teammate, Player B, as determined by the ball proximity sensing system.
  e. Impacts are measured simultaneously by Player B's boot and the ball (i.e., a successful pass is recorded).
  f. The ball leaves the proximity of Player B (e.g., by a kick by Player B).
  g. The ball enters the proximity of Player A and contacts Player A's boot (another successful pass).

Optionally, a successful give-and-go event may require successful passes from Teammate A to Teammate B and back to Teammate A within a predetermined time frame (e.g., in less than 5 seconds). The determination of this event also may require the ball to pass in proximity to, but not into the possession of, a player on the opposing team (e.g., a "Through Ball/Pass" event, as described below). Successful "give-and-go" events help provide a measure of how well groups of players work together and move the ball on the pitch.

FIG. 62—Through Ball/Pass:

Another interesting metric that may be measured by systems and methods in accordance with at least some examples of this invention relates to determination of a "through ball" or "through pass" event. A "through ball" or "through pass" as used herein in this context means that the ball is successfully passed from one teammate to another and, during the course of the pass, the ball passes in proximity to an opposition player. In some examples of such systems and methods, output from an impact sensing system inside the ball (accelerometer, pressure sensor, etc.) is time-matched to output from an impact sensing system inside the boot to enable determination of when the ball is struck by a specific foot. A proximity sensing system is also employed (magnetic sensing, RSSI, etc.) to enable determination of when the ball is in proximity to the players on the field. Then, a "through ball" or "through pass" event is determined by the following steps:

a. A player on team "A" is determined to have possession of the ball.
b. Impacts are registered on both the shoe sensor and the ball sensor simultaneously, registering a kick by a player on team A.
c. The ball leaves the proximity of the player that kicked it.
d. The ball is determined as having passed through the proximity of one or more players on the opposing team.
e. The ball enters the proximity of a teammate to the original kicking player (team "A"), optionally, a player that has been running forward onto the ball.
f. The ball sensor and the kick receiving teammate's shoe sensor simultaneously register an impact and optionally continued proximity to the teammate (beginning a ball possession event by the receiving player).

Optionally, if desired, the ball must pass in proximity to one or more players on the opposing team without the opposing team contacting and/or possessing the ball. This metric may be useful for evaluating the performance of players and their passing skills in a more closely defended environment.

FIG. 63—Pass Distribution:

Pass distribution information also may be an interesting and/or important metric for soccer players to consider and evaluate. As some more specific examples, a determination of a direction of a pass (e.g., advancing the ball, retreating, etc.) may be useful in evaluating player performance.

Output from an impact sensing system inside the ball (accelerometer, pressure sensor, etc.) may be time matched to output from an impact sensing system inside the boot to enable determination of when the ball is struck by a specific foot. Additionally, a rotational sensing mechanism (such as a magnetic sensor, gyro, etc.) inside the ball may be used to enable determination of an absolute direction of movement of the ball. A pass distribution metric may be determined through the following steps:

a. Direction of play is determined, e.g., as described herein.
b. Possession is determined, e.g., using techniques like those described above.
c. Simultaneous impacts to the boot and ball are recorded and communicated wirelessly (or stored) to indicate the ball has been kicked by a specific player.
d. Inertial sensors inside the ball are then used to determine the relative direction of flight of the ball.
e. Rotational sensors then record the absolute orientation of the ball as a result of the kick.
f. The two pieces of information from steps d and e can be used to determine the relative direction of ball flight to the direction of play determined in step a. This information can be then compared and evaluated to determine if the kick was advancing on the opponent or retreating, sent to the player's right or left, etc.
g. The final step is a possession determination awarded to a teammate, in order to call it a complete and successful pass.

The steps above constitute a determination of a successful pass between teammates. If, in step number g, the ball is detected to be in possession of the opposition team, this is also useful information. The direction of all passes made by a player throughout a game can be aggregated to determine pass success/failure rate when trying to advance/retreat the ball, as well as the amount of time the player moves the ball forward or retreats over the course of a game.

Finally, if desired, a core mounted directional sensor (e.g., compass, etc.) can be used to determine what movement/facing direction changes occur as a result of a player receiving the pass. Therefore, it is possible to use this technology to help give performance metrics, such as how often the teammate had to come to the ball, wait for the ball, or if the pass was laid out perfectly in front of the player.

Figure 64:
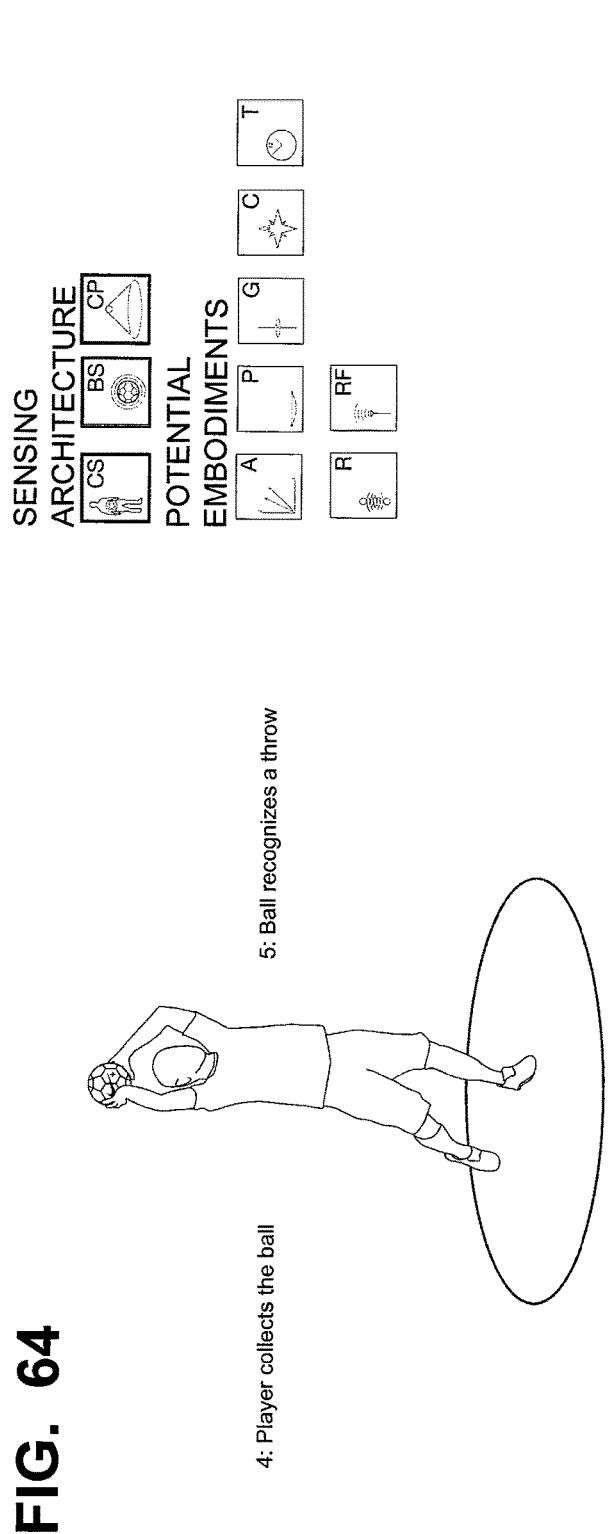

FIG. 64—Out of Bounds:

In order for an athletic performance monitoring system and method to understand the play of a soccer game, the system and method should not take into account possession, kicks, and other activities that occur when the ball is out of play. The following is an example of a system and method that may be used to determine when a ball has gone out of bounds.

Output produced by an impact sensing system inside the ball (e.g., accelerometer, pressure sensor, etc.) is time-matched to output produced by an inertial sensing system inside the boot to enable a determination of when the ball is struck by a specific foot, and optionally, to enable determination of the path that the foot has traveled. A proximity sensing system also may be employed (e.g., magnetic sensing, RSSI, etc.) to enable a determination of when the ball is in proximity to particular players on the field. One example process that may be used to determine when the ball has gone out of bounds is as follows:

1. An individual player possession is determined using technology/procedures as described above.
2. Optional: the ball detects a kick by the simultaneous impulse on the inertial sensing systems within the boot and the pressure/acceleration sensing systems in the ball.
3. Optional: the ball is detected to be within the radius of proximity of an opposing player.
4. Inertial sensors in the ball detect when the ball has been picked up (e.g., identifying the low frequency signals as compared to foot/ground impacts; identifying no motion, slow motion, or low spin motions for extended play; identifying speed of motion consistent with player's speed in proximity to the ball (i.e., the player holding the ball); etc.).
5. The ball either detects a throw-in or a set piece play using previously described methods.

Once this type of "out of bounds" situation is detected, systems and methods according to at least some examples of this invention can adjust the various determined metrics, such as possession time (e.g., by deducting from the determined possession time for an individual player or team the length of time between the throw-in or set point event and the previous kick (which induced the out of bounds event), etc.). Other metrics also may be adjusted based on "out of bounds" determinations without departing from this invention.

Figure 65:
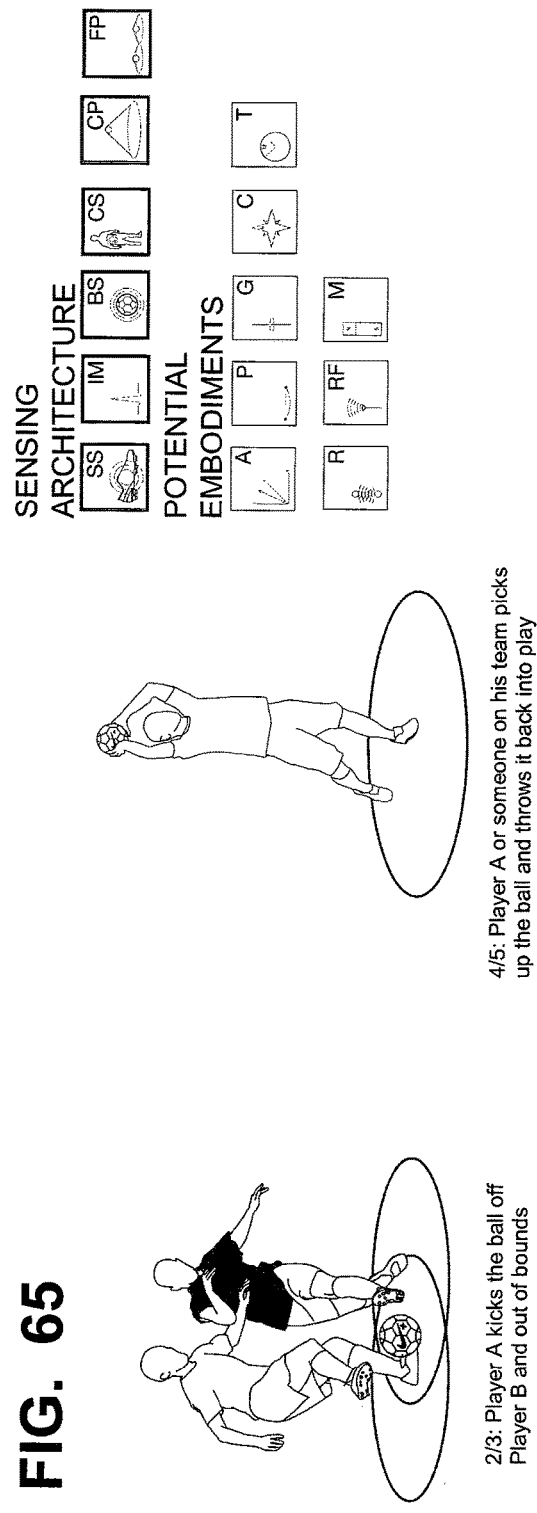

FIG. 65—Intentional Out of Bounds:

In a specific subset of normal "out of bounds" situations, as described above, sensing systems and methods in accordance with at least some examples of this invention may differentiate situations when a ball has been intentionally kicked against another player to send the ball out of bounds, resulting in maintaining possession. The same equipment may be used as described above in conjunction with FIG. 64, but additionally, ball proximity to another player and/or ball impact with another player also may be detected and relevant to the "intentional out of bounds" situation. The following example process may be used for detecting an intentional out of bounds situation:

1. An individual player possession is determined using technology/procedures as described above.
2. The ball detects a kick by the simultaneous impulse on the inertial sensing systems within the boot and the pressure/acceleration sensing systems in the ball.
3. The ball then detects another impact that does not coincide with a boot impact for any other player on the pitch (optionally, the ball also may be detected to be within the radius of proximity of an opposing player).
4. Inertial sensors in the ball detect when the ball has been picked up (e.g., as described above).
5. The ball either detects a throw-in or a set piece play using previously described methods.

Information relating to the ability of a player to induce an intentional out of bounds situation on the opposing team can be useful in ascertaining the skill of the player causing the intentional out of bounds situation (e.g., ball handling skills, defense avoidance skills, etc.), as well as the skill level of the defensive player against whom the ball was kicked to produce this situation.

FIGS. 66 through 75 illustrate various potential features for detecting and/or measuring various metrics relating to goals and/or activities of the goalkeeper in the game of soccer, which may be used and evaluated during a game, practice session, training session, etc. The features of these example systems, methods, and metrics will be described in more detail below.

FIG. 66—Keeper Recognition:

While systems and methods according to at least some examples of this invention may request input or special equipment for the goal keeper, if desired, at least some systems and methods according to examples of this invention may be capable of automatically identifying which player is the goal keeper based on detected activities that occur over the course of a game.

Example hardware for use in recognizing the goal keeper may include: (a) an inertial sensing system on the player (e.g., either on the core or in the boot) to provide player speed and distance information; and (b) a wireless communication system to allow the sensing systems on the individual players to broadcast their signals/processed data (or storage capabilities for this data). Then, as one example, the automatic determination of the keeper may be accomplished in the following way:

a. Speed and distance information is collected and considered for each player on the pitch.
b. The keeper, due to his/her position, will do the majority of his/her movement within an 18 yard box located near the goal.
c. After (or during) the game, the data from the sensing system can be evaluated to understand which player on the pitch moved the least, and stayed predominantly within an 18 yard box.

Different performance metrics (e.g., the performance metrics described in more detail below) may be determined for the player identified as the goal keeper.

As another alternative, if desired, the goalkeeper may be equipped with gloves that have the capability of determining contact with and/or proximity to the ball (e.g., impact sensors, accelerometers, ball-to-glove proximity sensing systems, etc.). Data collected by such gloves also may be used in various ways for determining various metrics, such as the metrics described in more detail below. As yet another example, systems and methods according to examples of this invention may allow the various players to enter data identifying their positions.

FIG. 67—Save/Goal Protection:

Systems and methods according to at least some examples of this invention may include features to enable determination of goal keeper saves and protection of the goal. This aspect of the invention may be accomplished using various sensors to determine when a keeper saves a shot on goal. For example, systems and methods according to at least some examples of this invention may utilize an inertial sensor on the body core of the keeper, a ball proximity sensing system, and an inertial sensing system within the ball, e.g., of the various types described above. A determination of an impact to the ball with significant magnitude (e.g., above a threshold level, such as would be present in a typical shot on goal, or a header off of a corner kick, for example), immediately followed by (or simultaneous with) ball proximity to the keeper, followed by a picked up ball, and then a drop kick or throw, may be used an indication that the goal keeper has saved a shot on goal (and successfully protected the goal). Additionally or alternatively, if desired, the goalkeeper may be equipped with gloves that have the capability of determining contact with and/or proximity to the ball (e.g., impact sensors, accelerometers, ball-to-glove proximity sensing systems, etc.), and such contact may be an indication of goal keeper interaction with the ball. As another alternative, sensor data taken from the goal keeper's body-worn accelerometer could be compared to sensor data from the accelerometer data in the ball. As the keeper runs or moves with the ball, the two sensors will indicate a very similar net path taken. This data can be used to determine possession of the ball by the goal keeper.

FIG. 68—Keeper Parry:

This example aspect of the invention relates to systems and methods capable of determining a "keeper parry" scenario, i.e., a situation where the keeper gets his hands (or other body part) on a shot on goal, which deflects the ball out of bounds (e.g., outside the goal, over the goal, etc.). As a more specific example, using inertial and pressure sensing systems inside a soccer ball, the ball will generally show a softer impact signature on the accelerometer and/or the pressure sensors when it contacts a player's hands, as compared to a goal-post impact, kick, or ground impact. This unique sensor signature and determination of a non-shoe/ground/goalpost impact, combined with detection of proximity to the keeper, followed by a set piece event (as described above, e.g., a corner kick), is a unique sequence of events that only happens when a keeper parry event occurs. Additionally or alternatively, if desired, the goalkeeper may be equipped with gloves that have the capability of determining contact with and/or proximity to the ball (e.g., impact sensors, accelerometers, ball-to-glove proximity sensing systems, etc.), and fleeting contact or proximity of the glove to the ball may be considered an indication of a keeper parry situation (optionally, combined with some of the other features of this scenario described above).

FIG. 69—Hard Shot Keeper Parry or Catch:

This example aspect of the invention involves determination of a keeper parry event or keeper catch of the ball that has been kicked hard. Defending against a hard shot will typically require improved goaltending skills, and the ability to differentiate saves in this situation may provide an additional interesting metric for coaches or players to consider. Systems and methods according to at least some examples of this aspect of the invention may use inertial and/or pressure sensing systems within the ball to determine ball speed as well as wireless communication capabilities included with the ball that are capable of broadcasting ball speed information and impact time information. Furthermore, systems and methods according to at least some examples of this invention further may include proximity and/or possession determination technology (such as magnetic, RF, or other) that allows a determination of when the ball is within proximity to (or in the possession of) specific players, and in this scenario, in proximity to or in the possession of the keeper.

The combination of the keeper's ability to catch or parry the ball (e.g., using sensing technology described above) vs. the ball speed can then be mapped into a player skill metric (e.g., percentage saves of shots on goals over a predetermined kick speed, etc.). For example, for faster ball speeds, the keeper's ability to parry or catch the ball can be considered more skillful.

As another alternative, keeper reaction time can be determined, for example, by comparing the time of kick with the time of impact by the keeper's hands. The time difference between the two events can inform how much time the keeper had to react to the shot on goal.

Information relating to this metric can then be displayed or visualized on a web page or hand-held device (such as a mobile phone) and compared with other metrics gathered by the system in previous and future games. Moreover, information relating to this metric may be used to develop training programs to improve player quickness, agility, and/or reaction time (if necessary).

FIG. 70—Keeper Advance (Tackle):

This example aspect of the invention uses a set of sensor systems on the keeper and in the ball to determine when the keeper performs a successful tackle, taking the ball away from the opposition. As some more specific examples, systems and methods according to this aspect of the invention may determine when an opponent has possession of the ball, followed by a contested time period between the keeper and the opposing player (e.g., both the keeper and the opposing player in close proximity to the ball), followed by a dive event performed by the keeper (e.g., determined by an on-body inertial sensing system carried by the keeper), followed by a picked up ball (e.g., which may be determined based on sensors in the keeper's gloves, accelerometer and/or gyro sensors in the ball, etc.). These events, happening in this sequence, are unique to a keeper tackle event. Tracking keeper tackle events provides an interesting and useful metric for evaluating keeper performance.

FIG. 71—Keeper Dive/Player Dive/Player Jump:

An inertial sensing system, such as a three-axis accelerometer, when mounted on the body of a player during a soccer match or other activity (especially at the body core), will spend the majority of the time in a fairly flat plane of motion (e.g., a certain height off the ground determined by sensor mounting location). When the keeper (or other player) dives to the ground, the sensor will make a sharp deviation downward to the ground, followed by the player standing up and resuming motion within the original plane of motion. These two events can be used to determine when the player has made a diving action and/or when he/she is standing up. This same technology may be used, for example, to determine when a player has jumped a significant height in the air.

FIG. 72—Drop Kick:

A "drop kick" event (a common event performed by a goal keeper in the game of soccer) also may be detected by systems and methods in accordance with at least some examples of this invention. Commercially available accelerometer technologies today can determine when the accelerometer (and hence the device with which it is engaged) is in a free-fall condition. Systems and methods according to this example of the invention use an accelerometer placed in a ball, in combination with an impact-sensing system in a shoe. These sensors can be used to determine the following event sequences, which correspond to and may be identified as drop kick events:

a. For a direct drop kick (in which the ball does not touch the ground first): the ball is picked-up, dropped (i.e., detected as being in free-fall), followed by a kick-impact (ball and shoe impacts at the same time).

b. For a bounced drop kick (in which the ball touches the ground briefly before being kicked): the ball is picked-up, dropped (i.e., detected as being in free-fall), makes a small impact due to contact with the ground, followed by a kick-impact (ball and shoe impacts at the same time) when the ball is traveling away from the ground. Alternatively, the ball may experience the kick-impact at the same time the ball contacts ground.

If desired, a maximum threshold time period may be initiated once the ball contacts the ground during which the kick event must be recorded in order for a successful bounced drop kick event to be counted.

FIG. 73—Shot on Goal that Goes Out of Bounds:

Systems and methods according to at least some examples of this invention may utilize a system of sensing elements in the ball (and optionally sensors in the boot) to determine when a ball goes out of bounds beyond the goal line (resulting in a goal kick), e.g., due to a wide kick or a high kick. The detectable events that enable determination of a "Shot on Goal that Goes Out of Bounds" are as follows:

a. Coincident impacts to the ball and boot are recorded to determine that a kick event has occurred.

b. The ball is then picked-up (which may be determined, for example, by detection of a very slow rotational pace and/or low frequency accelerations using inertial sensing/rotational sensing methods—the sensor output from a carry event will appear different from the sensor output from a kick event, e.g., in ball rotation, acceleration, etc.).

c. A set piece event then occurs (and optionally, a kick from the set-piece event may be detected).

This metric may be useful, for example, to determine offensive player skill and effectiveness, identifying missed opportunities during a game, defense effectiveness, etc.

As another example, if desired, the goal posts could include electronic modules thereon that allow proximity detection between the goal posts and the ball.

FIG. 74—Shot on Goal:

An important part of the game of soccer is the shot on goal. Systems and methods according to at least some examples of this invention include ball mounted sensors and/or player mounted sensors that will allow for detection of when a shot on goal has occurred. In one example system and method, output from an impact sensing system inside the ball (e.g., accelerometer, pressure sensor, etc.) is time matched to output from an impact sensing system inside the boot to enable determination of when the ball is struck by a specific foot. A proximity sensing system also may be employed (e.g., magnetic sensing, RSSI, etc.) to enable determination of when the ball is in proximity to specific players on the field. A core-mounted player rotational sensor also may be employed (e.g., compass sensor, gyro, etc.) to enable determination of which direction the player is facing as well as relative rotational information. Additionally, an inertial sensing system on the player can be used to provide additional signals and information. The events that occur to determine a shot on goal according to this example of the invention are as follows:

a. Possession by a member of the attacking team is determined, e.g., using techniques described above.
b. Signals from the pressure sensor or inertial sensor within the ball occur simultaneously to signals from the impact sensing technology within the boot.
c. Wireless communication between the boot and ball match the time exactly, recording the event as a kicked ball.
d. Proximity sensing systems record the ball entering the proximity radius of the defending team's goal keeper.
e. Inertial and rotational sensors within the ball record low-frequency signals that are characteristic of the ball being held by a person. Alternatively, inertial sensors on the player correlate closely to the path of travel recorded by the inertial sensors within the ball, suggesting the ball is being carried.
f. The ball is thrown, the ball is drop kicked, or a set-piece play is executed.

The "shot on goal" determination may be useful for a variety of metrics that may help determine the effectiveness of a goal keeper, the effectiveness of one or more offensive players, the effectiveness of one or more defensive players, team or line up effectiveness, etc.

FIG. 75—Goal Scored:

Systems and methods according to at least some examples of this invention also may be able to automatically determine when a goal has been scored. This may be accomplished, for example, by considering, at least in part, the behavior of the ball when it strikes the net and comes to a rest during a goal. As a more specific example, the following events may be used to determine that a goal has been scored:

a. Ball possession by a member of the attacking team is determined, e.g., using one or more of the techniques described above.
b. Signals from the pressure sensor or inertial sensor within the ball occur simultaneously to the signals from the impact sensing technology within the boot.
c. Wireless communication between the boot and ball match the time exactly, recording the event as a kicked ball.
d. Optionally, proximity sensing systems record the ball entering the proximity radius of the defending team's keeper.
e. An internal accelerometer in the ball recognizes that the ball has hit the net by producing signals indicative of a slow stop due to the ball being caught in the net (and optionally a gravity drop to the ground). This signal or series of signals will appear different from a more abrupt stop or direction change resulting from a catch or kick and/or the slow stop produced as the ball rolls to a stop.
f. Inertial and rotational sensors within the ball record low-frequency signals that are characteristic of the ball being held or carried. As an alternative, inertial sensors on a player correlate closely to the path of travel recorded by the inertial sensors within the ball, suggesting the ball is being carried.
g. The ball is carried back to the center circle and is place like a set piece for a restart to the game by the team that did not score. (Optionally, other events, like those described below, may be used as an indicator of play resumption).

The "goal scored" metric may be combined with other metrics, like possession information prior to the goal (e.g., to determine which player made the goal, assist information, etc.), goal keeper effectiveness, individual player effectiveness (both offense and defense), line-up effectiveness (both offense and defense), etc.

FIGS. 76 through 83 illustrate various potential features and/or functionality of systems and methods according to some example aspects of this invention relating to the various teams, team metrics, game features, and the like. The features of these example systems, methods, metrics, and functionality will be described in more detail below.

FIG. 76—Automatic Pick of Team Captains:

On "pick up" soccer matches, there is often the need to choose a captain of each team who will then each choose their players one at a time. If desired, systems and methods according to at least some examples of this invention may be programmed and adapted to automatically pick captains from an assembled group of players, e.g., based on one or more metrics relating to the player of the assembled group of players.

As some more specific examples, systems and methods according to at least some examples of this invention may utilize the data and contextual information amassed by the assembled players over multiple games played. This example system involves nodes on each player that comprise the sensing systems described above, as well as a means of communicating wirelessly. One or more metrics for the assembled players can then be communicated to a common location (e.g., a cellular telephone, a palmtop computer, a laptop computer, a sideline computer, one of the player's body mounted devices, etc.) where the data can be collected and compared. Once the devices have communicated relative skill levels of the assembled players (e.g., by transmitting any of the various metric information as described above), the two best players (or any other metric such as the two worst players, the two best passers, the two best (or worst) goalkeepers, etc.) can be chosen to be the captains. If desired, systems and methods according to at least some examples of this invention may determine the best two overall players and the best two goal keepers and then divide these four players between the teams so that the best goal keeper is on the team of the second best player and so that the second best goal keeper is on the team of the best player. Any desired way of dividing up the players and/or choosing the captains may be used without departing from this invention.

As another alternative, rather than simply picking captains or goal keepers, systems and methods according to at least some examples of this invention can assemble, compile, and review the data to determine the fairest distribution of the assembled players among the teams using the metrics that have been amassed over multiple games played using the sensing systems and methods according to this invention.

As yet some additional options, if desired, systems and methods according to at least some examples of this invention that automatically choose the entire teams based on the assembled players may perform additional functions as well. For example, any way of advising the players of the team on which they should play on may be provided without departing from this invention. As some more specific examples, systems and methods according to the invention could send a team indicator message to the cell phone or other electronic device of each player (e.g., "You are on Team 1" or "You are on Team 2"). As another option, if desired, the computing system that automatically chooses the teams can wirelessly communicate with an electronic module provided on a garment or jersey, which can then change color, present textual information, or produce other features to show the team assignment decisions that were made.

FIG. 77—Determination of Game Start:

Systems and methods according to this invention may determine when a game actually starts (which can be the signal to start accepting data from the various sensors, e.g., mounted on the ball, players, goalposts, other equipment, etc.). Any desired way of ascertaining the start of the game may be used without departing from this invention. As one example, one player or other individual (such as a referee, a coach, etc.) may be tasked with manually providing an indication to a computing system as to when the game has started. As another example, the "game start" event can be determined by detection of a set piece event (as described above) within a short time frame after all players (or a majority of the players) in the game activate their on-body sensing systems using a peer-to-peer network, followed by a very short pass within team members.

Other ways of automatically determining the start of the game may be provided without departing from this invention. For example, in some example systems and methods according to the invention, all players on the field that are using the sensing systems and have on-body inertial sensing systems in accordance with this invention will be in communication with one another over a peer-to-peer network. The beginning of the game is one of the very few situations where the players are all standing reasonably still and two players on the same team are in close proximity to the ball. Detection of this type of activity or situation, followed by sudden and simultaneous movement by almost all of the players, may be used as an indication that the game has started.

As another example, in some systems and methods according to examples of this invention, all (or many) players may have an on-body sensing system that determines the orientation of the core of the body. Each sensing system may be connected via a wireless communication method that defines a peer-to-peer network. In such a system, all the modules can broadcast the direction on the field in which each person is facing. Combining this facing direction information (all team members facing the same direction, which is opposite to the direction that the opposing team faces) with detection of a set piece event, and optionally adding the proximity information described above where two players of the same team are standing within close proximity to the ball, can be used as an indication that the start of the game is about to occur (or has occurred once the initial kick is sensed).

As yet another alternative, the start of the game may be determined by substantially simultaneous movement by each player from a generally standing still position, due to the kickoff (optionally, correlated to a set piece event and/or an initial kick detection event, as described above).

Figure 78:
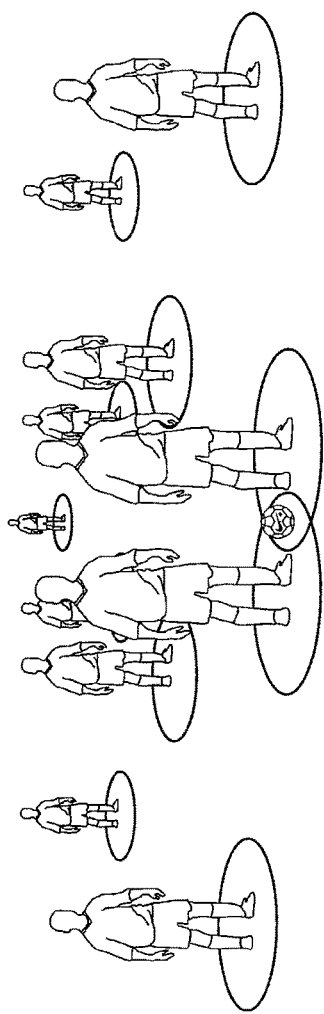

FIG. 78—Direction of Play:

For various metrics relating to the play of soccer (e.g., to determine the course of play, to determine whether a team tended to be attacking or defending, to determine various skill metrics, etc.), the direction of play for each player and/or each team may be a useful piece of information for sensing systems and methods according to at least some examples of this invention (e.g., so the systems and methods know which goal each team and player is defending and which goal each team and player will approach to score). Systems and methods according to at least some examples of this invention may determine the direction of play automatically, e.g., based on the movements of the various players over time. Determination of the direction of play according to at least some examples of this invention may utilize a body-mounted sensor with direction sensing capabilities (e.g., a compass sensor, accelerometer/gyro, etc.) to determine the direction that a player is facing at any given time. For such systems, direction of play may be determined by the following steps:

a. Multiple players on the pitch have sensing systems that include wireless communication means for sharing directional information.

b. Sensor signals are read on each individual player and are broadcast wirelessly to all sensor nodes (e.g., on each player).

c. The nodes are all integrated over the course of play to determine which players spend most of their time facing a particular direction.

d. Teammates will all share a similar bias toward facing the opposition goal.

This technology may be used to automatically determine which players are teammates. Additionally, as noted above, it may be useful for determining various metrics relating to the game, both on a team level and on an individual level. For example, offensive players that spend too much time facing their own goal may not be as effective as offensive players that spend less time facing their own goal. This data may also be used to determine which team seemed to play a more "attacking" game v. which team seemed to play be more defensive.

Figure 79:
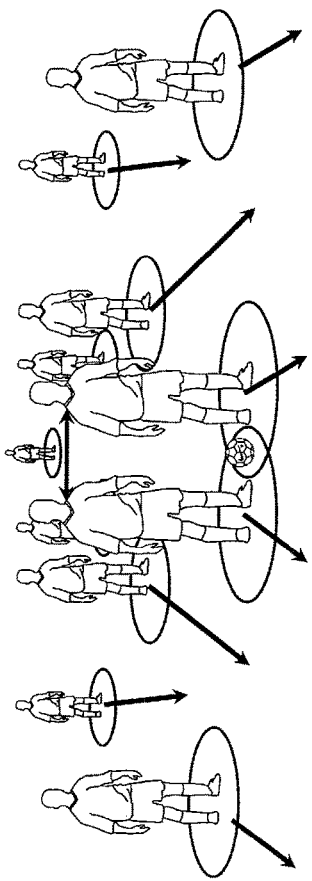

FIG. 79—Direction of Play Alternates:

FIG. 79 helps illustrate various alternative features for automatically determining direction of play (or information that may be used in automatically determining direction of play and/or automatically ascertaining teammates) that may be used in systems and methods according to at least some examples of this invention. For example, knowledge of the "start of game" metric, as described above, can be used to instantaneously look at the output of the core sensors to understand direction of play of individuals and/or teams and/or automatically determine the teammates. More specifically, in general, at the start of the game, members of each team will face the opponent's goal. Therefore, the individual facing direction information at the beginning of the match for each individual may be stored, and this information can be used, at least in part, to determine the direction of play for each individual and/or the members of each team.

As another alternative, ball possession information (and the sensors that collect individual player possession information) may be used in combination with the direction facing sensors described above to enable determination of which direction the players are facing when on-ball, and the majority of dribbling performed by that player will be presumed to be driving toward the opposition goal.

As another alternative, pass sensing technology (e.g., as described above) can be used to determine a general pass direction bias, optionally combined with the length/direction of passes, to enable a determination which direction a particular team or individual is most often trying to move the ball. This directional information may be presumed to be oriented toward moving the ball toward the opposition goal.

Another potential alternative for automatically determining the individual and/or team direction of play (and optionally the identity of teammates) may take place during "set piece" plays. More specifically, during set piece plays, the majority of each team's player's will be facing toward the opposition goal. Directional sensors can combine with determination of a set piece condition (e.g., as reported by the ball via a wireless network, e.g., using technology described above), which can then be used to trigger a communication of all players' facing directions by the core-worn sensing systems.

As yet another potential option, during long dribbles, the body core worn sensor on the individual player will tend to report movement toward the opposition goal. This can be either an inertial sensor system (accelerometer, etc.) or a rotational sensor (gyro, compass, etc.), as both may be capable of reporting a movement/facing direction biased toward the opposition goal.

The various automatic direction and/or teammate recognition technology, as described above in conjunction with FIGS. 78 and 79, may be used individually or in any desired combination to provide data relating to and useful in the final determination of an individual and/or player direction of play and/or recognition of teammates.

FIG. 80—Teammate Recognition Using Pass Distribution During a Game:

This aspect of systems and methods according to at least some examples of this invention uses the pass distribution technology previously described (see FIG. 63). By aggregating the pass distribution data over time (e.g., via wireless communication between sensor modules), systems and methods according to at least some examples of this invention may determine the people that are most frequently passed to by a particular player, and thus the systems and methods may conclude that these frequent pass recipients are teammates of the passing player. During the course of a game there may be multiple pass interceptions, but presumably, the dominant number of passes that occur will be to a player's teammates. Over time, a pattern will emerge that will allow the system to dynamically figure out who is on the same team, and who is not. Player-to-player and player-to-ball proximity information also may be used in this aspect of the invention, e.g., this data may better allow a determination of whether the passing player tends to try to pass to an individual or whether the passing player tends to send passes so as to avoid an individual.

Alternative technology may be provided that allows players to manually enter the team on which they play (e.g., by input to their body worn sensors, by selection from a menu, etc.).

FIG. 81—Determination of Team Based on Object Orientation:

Various examples of ways of determining which players are on which team (or at least data relating to this determination) are described above. Additionally or alternatively, systems and methods according to at least some examples of this invention may use the orientation of the receiver system (or any component of the system) to determine or as an indicator of which team a particular player is on. Because the game of soccer always involves only two teams, this determination or indicator system may be binary.

Various binary indicators may be provided without departing from this invention. As one example, using an accelerometer or other inertial sensing system, the gravity vector may be used to determine the orientation of the object. As another example, a pocket or clip that is intended to house at least some part of the sensing system may have a magnet embedded in it, and this magnet may be sensed by a Hall-effect sensor, reed switch, or similar to determine object orientation. As some example, the location of the magnet could be in a plastic housing, or even embedded into an apparel pocket. As another alternative, a passive element, such as a ball bearing or similar object, may be pulled downward by gravity, making an electrical contact with two electrodes inside the object. The side of the housing or other object toward which the ball bearing is pulled by gravity can be used as an indicator of the orientation (and therefore team) of the object. The players could wear the various sensors or the housings therefor in one orientation on one team and in the opposite orientation on the other team.

FIG. 82—Determination of Team Using Ball Proximity/Passing:

Aspects of this invention, as described above, may include proximity sensing systems in the ball, as well as inertial/impact sensing systems in both the ball and the boot. As another feature, systems and methods according to at least some examples of this invention may use the ability of the ball to know when it is in tight proximity or know when a simultaneous impact event occurs between the boot and the ball, which may be communicated wirelessly, signaling the ball's presence at the feet of a particular player. This example feature according to the invention uses a simple algorithm that allows the system to learn the teams. For example, prior to the start of the game (or at some other desired time), the ball may be simply passed around to each member of a team, signaling their status as teammates. This example system and method can then use the "passed around" players as one team, and any other players the ball comes in proximity to can be assumed to be on the opposing team.

Alternatively, if desired, a controlled behavior (such as squeezing the ball, picking the ball up, throwing the ball, etc.) can be used to signal the "transition" from passing around between the players on team #1 to passing the ball around between the players of team #2, and in this manner the ball can positively identify the various members of each team, e.g., before the game begins.

FIG. 83—Use of Pass Frequency to Determine Teammates:

This aspect of the invention uses the technology described above to determine when a successful pass has been made, but it but removes the knowledge of knowing teammates at the start of the game. If desired, systems and methods according to examples of this invention can automatically determine the teammates using pass frequency information. In this example system and method according to the invention, the system wirelessly communicates whenever the ball has traveled from one player to another, regardless of team. Throughout the game, patterns will emerge between certain players, and the pass frequency between players on the same team should be much higher. Statistical predictors can then figure out which 11 players (or other number of players) are most likely on the same team by evaluating the frequency of passing among them (many passes between two individuals most likely identifies them as teammates—two players cannot be that bad to always kick intercepted passes to the same person). Player-to-player and player-to-ball proximity information also may be useful in this determination.

Pass frequency features can be used in other manners in systems and methods according to examples of this invention, if desired. For example, an individual player's "preferences," such as which players are passed to more often by a particular player, can be identified and visualized online for improvement suggestions. As a more specific example, if a mid-fielder is always passing to the left side, he/she may become more predictable to the opponent. A coach noting or informed of this preference or tendency can develop drills for this player to help improve his/her skills and confidence in passing to the right side of the field.

Additionally or alternatively, if the speed of the player during the passing is added to the above pass frequency information, the system and method can be improved. Pass accuracy may change based on player speed. So added weight in the algorithm can be placed on passes that occur when players are moving at relatively low speeds (as compared to higher speeds). This may be most evident, for example, when the players pass the ball around the backfield, trying to create space within the field to open up a player for a pass near the opponent's goal.

FIG. 84—Post Game Concepts

Various post game features may be made available by systems and methods according to examples of this invention, e.g., such as displaying data and various metrics regarding player performance as described above. If desired, systems and methods according to at least some examples of this invention may allow players to gather and play some "quick games" using display devices immediately after the game. For example, the various players could gather after the game (e.g., on one team, both teams, portions of either team, etc.) and the data collected for these players may be combined (e.g., via wireless communication technology, peer-to-peer connections, etc.) to enable the players to compare and contrast their performances over the course of a game, workout, or practice session. Examples of the data that may be determined and displayed after the game in a quick gathering of players (e.g., on one or more player's cell phones, handheld computing devices, etc.) include, but is not limited to identification of: Who had the longest successful pass? Who reached the fastest speed on/off ball? Who was the best passer (e.g., most passes, fewest interceptions, highest successful pass percentage, etc.)? Who was the workhorse (e.g., who ran farthest, who had most possession time, etc.)? Who had the fastest kick? Who had the most tackles? These metrics, quick games, and competitions can be displayed on an LCD or similar display immediately following the game (or at any other desired time), e.g., giving the system a richer experience with immediate feedback after the game has been played (or even during the game). The data displayed may include only data among the players gathered at the end of the game for this type of session, or it may include data collected from all of the players by systems and methods according to this invention.

FIGS. 85 through 93 illustrate various potential features and/or functionality of systems and methods according to some example aspects of this invention relating to the various miscellaneous metrics, game features, and the like, including various uses of magnetics and magnetic properties. The features of these example systems, methods, metrics, and functionality will be described in more detail below.

FIG. 85—Electromagnetic Coils in Ball:

This example aspect of the invention uses coils with pulsed current loads placed inside the ball to create a magnetic field that can be detected by sensors outside the ball. Adding a pulsed magnetic field can allow sensing mechanisms in accordance with some examples of systems and methods of the invention to filter for a very distinct signature, giving greater range/proximity detection (e.g., it allows body mounted detector systems to look for specific signal patterns representative of the ball and/or provides better ability to filter out "noise"). As another potential option, if desired, coils with different pulsation rates can be placed throughout the ball to allow sensors (e.g., body mounted sensors, shoe mounted sensors, etc.) to detect specific places on the ball, as well as the direction of rotation, based on the sequence of the magnetic pulse rates detected. This data may be useful, for example, to determine features of kick length, pass length, and/or other performance metrics.

FIG. 86—Juggling:

This example aspect of the invention uses the previously described integration of magnetic coils and sensors in the ball combined with sensing elements in the boot to detect very close proximity to the ball. Additionally, inertial or pressure sensors may be provided within the ball to detect an impact. When an impact is detected by the ball, the magnetic sensors also can be polled to understand if there was a simultaneous impact or close proximity to the boot, and such a system can wirelessly communicate (or store) the number of times in a row the ball was "juggled" by a player.

Alternatively, impact sensing elements in the shoe (e.g., accelerometer, piezo element, etc.) may be combined with inertial or pressure sensing elements in the ball. The simultaneous impact to the ball and shoe denote a kick, and wireless communication between the two systems may be used to determine how many times in a sequence the ball was kept in the air without impacting another surface, giving the player the number of times the ball was juggled. Additionally or alternatively, if desired, time between impacts, impacts with player's knees, and/or other features may be factored in and considered in determining whether a juggling event has continued.

FIG. 87—Ball Creates Magnetic Field Proportional to Pressure:

Systems and methods according to this example of the invention include an electrical, electro-mechanical, or mechanical system inside a soccer ball that creates a magnetic field that is proportional to the pressure inside the ball. The magnetic field generated then can be sensed by external sensors, such as sensors on the boot and/or body core mounted sensors. Examples of implementation and use of this example aspect of the invention include, but are not limited to, ball proximity detection (when kicked), detection of internal pressure using external sensing, kick speed, kick force, kick distance, etc.

FIG. 88—Integration of Magnets into Apparel for Ball Detection:

Another potential feature of systems and methods according to at least some examples of this invention relates to the use of magnets (either permanent or electro-magnets) and their integration into apparel for a soccer player. The magnets are placed in locations which allow a magnetic sensor within the ball to detect their field, and as such detect what part of the body had just interacted with a ball. As a more specific example, the chest is used in the game of soccer to trap or stop a highly-lofted ball. Upon close proximity to the garment, the ball may detect the magnet in the clothing and knows which part of the body is closest (e.g., the magnet could be provided in shirt to demonstrate and detect chest/shoulder control, in the shorts to demonstrate thigh or knee control, in a headband or hat to demonstrate head control, etc.). Alternatively, if desired, the magnet could be included in the ball and the sensor mounted on various articles of clothing and the data could be transmitted or stored in the article of clothing.

As another alternative, if desired, inertial and/or pressure sensing systems provided inside the ball may activate/trigger the magnetic detection sensors when an impact is recorded, allowing the power system to save battery power and gain efficiency.

FIG. 89—Shoe Power Plate:

This aspect of the invention uses a fluidic material that hardens when exposed to a magnetic field. Fluid pockets are created within the shoe and/or protective gear (such as a shin guard, etc.), and the fluid included in the pockets remains viscous and soft until a magnetic coil residing underneath or on top of the pocket energizes. This action makes the material very hard, which can protect the foot, provide a harder kicking surface (to produce greater shot power), etc. Magnetic "smart" fluids, also called "magnetorheological fluids" are known and used in the vehicle suspension arts and as "liquid body armor" (e.g., for bulletproof vests).

Alternatively, if desired, the fluidic pockets need not have a magnetic coil underneath them, but rather the ball may be adapted to contain magnets that, when in close enough proximity to the fluid, change the state of the fluid, making the boot hard. As another alternative, if desired, a combination of the sensing systems, e.g., as described above, can offer contextual information to a processing system provided in the shoe, which in turn can activate magnetic field generators (e.g., also in the shoe), which can actively change the hardness and flexibility of the shoe based on real-time information about the game. Alternatively, the shoe can use skill-based metrics gained from previous contests to understand what kind of player the athlete is, and how a shoe may better serve the specific needs of the player.

FIG. 90—Shin Protection Plate:

Aspects of the "shoe power plate" technology described above in conjunction with FIG. 89 may be used in other environments as well. For example, this same type of magnetic "smart" fluid or magnetorheological fluid may be provided in a pocket of a sock or other clothing to function as protective gear (such as a shin guard, etc.). If desired, an opponent's shoes may be equipped with a magnet or magnetic force generating system which would trigger/activate the magnetorheological fluid when the shoe closely approached the protective gear. In this manner, the sock or other item may conform well to the wearer's body (so that it is comfortable and stays in place) during normal use and only becomes hardened when a magnet equipped boot (or the ball) approaches.

FIG. 91—Magnetic Coil to Sense Shoe Properties During Running:

This aspect of the invention involves placing a coil of wire inside a shoe, as well as a permanent magnet that passes through the coil, generating a current flow through the coil. This current flow then may be used to sense the "contact time" of when the shoe is on the ground. More specifically, when running, the shoe will flex, which through a mechanical mechanism moves a magnet within the coils generating the field. When a runner is running, the shoe will flex until a "toe off" event, and then while in the air the shoe will return to steady state (e.g., a flat sole). Then, after a "heel strike" event occurs, the shoe will begin to flex again, moving the magnet within the coil. These two signals, from the heel strike and the toe off events, can be used to determine when the shoe is on the ground and when it is in the air. This information can be used, e.g., with conventional pedometer type speed and distance determination algorithms, as data useful in determining player speed metrics, which can be integrated to get a player distance moved metric.

FIG. 92—Magnetic Sensors Coming on Pitch Turns on Body Sensor:

This example aspect of the invention uses a magnetic sensor in the boot or on the player's body (e.g., sensors already provided for player-to-ball or player-to-player proximity detection or for any of the previously described purposes) to act as a switch to prepare the system for the start of the game. For example, magnetic mats (or cones or other structures) may be provided at the side of the pitch, and as the players approach and enter the field, they will pass over/through this the system. This action may be used to turn on the system and get it into a "ready" state for the start of the game. The system can then be started when a game start event is detected (e.g., as described above), or when a player manually activates the system at the start of the game. The magnetic field also could be directionally varied (e.g., change in strength over the course of its length) so that systems and methods according to this aspect of the invention can ascertain whether the player is entering or exiting the field.

FIG. 93—Magnet in Ball Pulls Up Magnetic Sensor Switch in Shoe:

This aspect of the invention may be used, for example, as an alternate system in determining player-to-ball proximity and/or player possession as described above. Systems and methods according to this example of the invention use a magnetic switch in shoe that moves to signal proximity when the magnets in the ball come close. As an example, as illustrated in FIG. 93, a reed type switch may be provided in the shoe that makes contact with an electrical contact provided in the shoe when a magnetic source provided in the ball induces the reed portion of the switch to move upward or downward. When the magnet in the ball is out of range of the switch, the reed returns to its neutral, un-contacting position. Thus, data collected resulting from contacts between the reed switch and the contact in the shoe can be used to determine and count interactions between the ball and shoe (and thereby provide information regarding proximity to the shoe and/or ball contact with the shoe (e.g., possession, passes, juggling, etc.)).

FIG. 94: Field Location "Heat Map":

If desired, systems and methods according to at least some examples of this invention may produce a field location "heat map" that indicates where on the field the player spent time and, optionally, an indicator of the amount of time spent on that portion of the field. FIG. 94 illustrates an example field "heat map" that may be generated using systems and methods according to at least some examples of this invention. As shown in FIG. 94, the representation of the soccer field (which may be provided on any desired type of display device, e.g., as described above) may include various zones or regions that indicate where the player spent his or her time during the course of the game. The colors of the various zones may provide an indicator of the amount of time spent within that zone. This type of information may be useful, for example, by a coach and the player, to determine how well the player stays in position and/or when/if the player spends time outside of the desired or optimal positions. This information also may be useful as an aid for determining whether a player or team is in more of an attacking or defending posture. If desired, the "heat map" may be capable of displaying player positioning during an entire game or practice session, during any desired portion of a game or practice session, and/or even comparing player performance from one game to the next (e.g., by overlaying one heat map on another).

Any desired type of player location determining systems and methods may be used without departing from this invention, such as GPS. As another alternative, the initial player location of the field may be entered, e.g., by the player starting at a fixed location for his/her position, and then systems and methods according to aspects of this invention may track the player's location from this initial starting location, e.g., using one or more of: an accelerometer, a gyroscope, a compass, etc. As yet another alternative, player location may be determined automatically over the course of a game, e.g., by noting the player's tendency to avoid going over end lines and side lines, the player's general positions and movement on the field may be determined based on approximate determined locations for the end lines and/or the side lines. As yet another example, the general heat map may be generated without reference to a location on the field, and after the fact the user could anchor the heat map location with respect to a representation on the field, e.g., based on knowing an approximate location where they started or ended the game, based on their position, etc.

Also, if desired, the heat map may include information regarding ball possession. As a more specific example, if desired, a special heat map may be developed and presented to identify locations on the field where the player had possession of the ball. This heat map may include different colors to indicate the number ball possessions at the indicated location, the time of possession at the indicated locations, etc.

Other Information:

As noted above, systems and methods according to at least some examples of this invention will be capable of determining when a ball is sent out of bounds. Data to assist in evaluating and determining this feature may include, for example, data indicating that the ball has decelerated, data indicating that the ball is not rotating (e.g., being carried), or data indicating that the ball is moving slowly (e.g., being carried), etc. Optionally, this deceleration, non-rotation, and/or slow motion activity may be required to last for a predetermined time period (e.g., at least 2 seconds, at least 3 seconds, etc.). Once it is determined that the ball is out of bounds, systems and methods according to examples of this invention may work backwards to subtract accumulated possession time (e.g., individual or team) from the time stamp of the previously ascertained and recorded kick (i.e., the last "in bounds" kick).

Also, as noted above, systems and methods according to at least some examples of this invention may know or be capable of determining when two or more players are located within close proximity to the ball. During this time, neither player may be considered as being in clear "possession" of the ball. This time also may be categorized by systems and methods according to examples of this invention as "contested time." A determination of "contested time" may trigger a stop in accumulation of team and/or individual possession time (optionally, depending on whether the opposing player contacts the ball during the contested time or whether the initial party determined to be in possession of the ball maintains the ball free from contact of or proximity to the other player during the contested time). A new "possession time" may begin (for either team or any present individual) after the "contested time" period ends. Optionally, if desired, an individual's and team's possession time could continue during a contested time period, e.g., at least until the opposing player contacts the ball, or until the opposing team clearly gains possession of the ball. Contested time also could accrue when two players reach a loose ball at or near the same time (i.e., when no one had clear prior possession, such as when the ball moves from one contested time situation to another).

While many example systems, methods, features, metrics, and aspects of this invention have been described in conjunction with the game of soccer, aspects of this invention also may be extended for use in a variety of other sports, such as football, basketball, lacrosse, tennis, baseball, rugby, hockey, field hockey, cricket, and golf.

III. CONCLUSION

The present invention is described above and in the accompanying drawings with reference to a variety of example structures, features, elements, and combinations of structures, features, and elements. The purpose served by the disclosure, however, is to provide examples of the various features and concepts related to the invention, not to limit the scope of the invention. One skilled in the relevant art will recognize that numerous variations and modifications may be made to the embodiments described above without departing from the scope of the present invention, as defined by the appended claims. For example, the various features and concepts described above in conjunction with FIGS. 1-94 may be used individually and/or in any combination or subcombination without departing from this invention.

We claim:

1. A system, comprising:
a sensor system that monitors an athletic performance of a first player, the sensor system including at least a first sensor mounted to a set of shin guards, wherein the sensor system is programmed and adapted to:
send, based on a first type of activity performed by the first player, contextual performance information to an on-body receiver, the contextual performance information comprising at least a proximity of the first player to a game ball;
the on-body receiver, wherein the on-body receiver is programmed and adapted to:
receive data collected by the sensor system, wherein the on-body receiver includes one or more body-mounted activity sensors; and
determine, based on the contextual performance information comprising at least the proximity of the first player to the game ball, one or more data processing algorithms for determining a plurality of performance metrics for the first player;
a data storage system that stores data collected by the sensor system; and
an output device programmed and adapted to output perceptible athletic performance information based on data collected by the sensor system and the on-body receiver.

2. The system of claim 1, wherein the on-body receiver is programmed and adapted to:
determine whether athletic activity data obtained from the on-body receiver is available, and
when the athletic activity data is available:
generate, based on athletic activity data obtained from the on-body receiver being available, a first set of athletic performance metrics; and when the athletic activity data is not available:
receive a first set of athletic activity data obtained from the sensor system; and
generate a second set of athletic performance metrics based on the first set of athletic activity data.

3. The system of claim 2, further comprising a processor system configured to:
adjust an accuracy of one or more athletic performance metrics in the first set of athletic performance metrics based on the first set of athletic activity data.

4. The system of claim 2, further comprising a processor system configured to:
calibrate the one or more body-mounted activity sensors based on athletic activity data collected by the sensor system.

5. The system of claim 1, wherein the sensor system is further programmed and adapted to:
initiate, based on determining that the first player is within a threshold proximity to the game ball, a first data processing algorithm for determining a first performance metric.

6. The system of claim 5, wherein the sensor system is further programmed and adapted to:
initiate, based on determining that the first player is not within the threshold proximity to the game ball, a second data processing algorithm for determining the first performance metric.

7. The system of claim 5, wherein the first performance metric comprises one of: a speed of the first player or a distance traveled by the first player.

8. The system of claim 1, wherein the output device is programmed and adapted to provide real-time activity feedback to the first player during the athletic performance.

9. The system of claim 1, wherein the on-body receiver further comprises a wrist worn device.

10. The system of claim 1, wherein the sensor system is further programmed and adapted to:
determine a first direction of movement for the first player; and
initiate a first data processing algorithm based on the first direction of movement.

11. The system of claim 1, wherein the sensor system is further programmed and adapted to:
detect a second direction of movement for the first player; and
initiate a second data processing algorithm based on the detected second direction of movement.

12. The system of claim 1, wherein the output device is further programmed and adapted to:
display in a first interface a graphic visualization of an amount of time the first player was within a threshold proximity to the game ball.

13. The system of claim 1, wherein the output device is further programmed and adapted to:
display in a first interface one or more locations of a game field wherein the first player was in possession of the game ball.

14. The system of claim 1, wherein the on-body receiver is further programmed and adapted to:
receive, from a remote device, control data to adjust one or more functions of the on-body receiver.

15. The system of claim 1, wherein the sensor system is further programmed and adapted to:
determine a plurality of foot paths corresponding to a plurality of kick motions performed by the first player;
determine foot impact location data associated with each kick motion performed by the first player; and
output, to a computing device, a kick type distribution for the first player based at least on the determined plurality of foot paths and the determined foot impact location data.

16. The system of claim 1, wherein the sensor system is further programmed and adapted to:
receive, from a remote device, control data to adjust a function of one or more sensors of the sensor system.

* * * * *